US010074807B2

(12) United States Patent
Buesing et al.

(10) Patent No.: US 10,074,807 B2
(45) **Date of Patent: *Sep. 11, 2018**

(54) COMPOUNDS FOR ELECTRONIC DEVICES

(71) Applicant: Merck Patent GmbH, Darmstadt (DE)

(72) Inventors: Arne Buesing, Frankfurt am Main (DE); Holger Heil, Frankfurt am Main (DE); Philipp Stoessel, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 246 days.

This patent is subject to a terminal disclaimer.

(21) Appl. No.: 14/691,708

(22) Filed: Apr. 21, 2015

(65) Prior Publication Data

US 2015/0228905 A1 Aug. 13, 2015

Related U.S. Application Data

(62) Division of application No. 13/001,818, filed as application No. PCT/EP2009/003602 on May 20, 2009.

(30) Foreign Application Priority Data

Jul. 29, 2008 (DE) ........................ 10 2008 035 413

(51) Int. Cl.

| | |
|---|---|
| ***H01L 51/50*** | (2006.01) |
| ***H01L 51/00*** | (2006.01) |
| ***C07C 13/62*** | (2006.01) |
| ***C09K 11/06*** | (2006.01) |
| ***C09K 11/02*** | (2006.01) |
| *H01L 51/52* | (2006.01) |

(52) U.S. Cl.

CPC .......... *H01L 51/0056* (2013.01); *C07C 13/62* (2013.01); *C09K 11/025* (2013.01); *C09K 11/06* (2013.01); *H01L 51/006* (2013.01); *H01L 51/0058* (2013.01); *H01L 51/0067* (2013.01); *H01L 51/0072* (2013.01); *H01L 51/0073* (2013.01); *H01L 51/0074* (2013.01); *C07C 2603/16* (2017.05); *C09K 2211/1007* (2013.01); *C09K 2211/1011* (2013.01); *C09K 2211/1018* (2013.01); *H01L 51/5012* (2013.01); *H01L 51/5048* (2013.01); *H01L 51/5064* (2013.01); *H01L 51/5072* (2013.01); *H01L 51/5088* (2013.01); *H01L 51/5206* (2013.01); *H01L 51/5221* (2013.01); *H01L 2251/301* (2013.01); *H01L 2251/308* (2013.01); *Y02E 10/549* (2013.01); *Y02P 70/521* (2015.11)

(58) Field of Classification Search

None

See application file for complete search history.

(56) References Cited

U.S. PATENT DOCUMENTS

2009/0062570 A1* 3/2009 Cheng .................... C07C 13/58 568/633
2009/0184313 A1* 7/2009 Buesing ................ C07C 13/24 257/40

FOREIGN PATENT DOCUMENTS

| | | | |
|---|---|---|---|
| CA | 2608765 | A1 | 11/2006 |
| JP | H05-301876 | B2 | 11/1993 |
| JP | 2007/052091 | A | 3/2007 |
| JP | 2007-108310 | A | 4/2007 |
| JP | 2008-127294 | A | 6/2008 |
| JP | 2008-153047 | A | 7/2008 |
| JP | 2009/009965 | A | 1/2009 |
| JP | 2009/059840 | A | 3/2009 |
| JP | 2009-302466 | A | 12/2009 |
| WO | WO-04/041901 | A1 | 5/2004 |
| WO | WO-07/140847 | A1 | 12/2007 |

OTHER PUBLICATIONS

Setayesh, S., et al., "Polyfluorenes with polyphenylene dendron side chains: toward non-aggregating, light-emitting polymers," J. Am. Chem. 2001, vol. 123, pp. 946-953.

Niu, Q., et al., *Enhancing the Performance of Polymer Light-Emitting Diodes by Integrating Self-Assembled Organic Nanowires* (2008), Adv. Mater., 20, pp. 964-969.

* cited by examiner

*Primary Examiner* — Gregory D Clark

(57) ABSTRACT

The present invention relates to compounds of the formula (1), to the use thereof in electronic devices, and to electronic devices, particularly organic electroluminescence devices, comprising said compounds according to the invention, particularly as blue emitting material in an emitting layer.

formula (1)

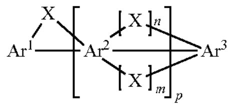

4 Claims, No Drawings

COMPOUNDS FOR ELECTRONIC DEVICES

RELATED APPLICATIONS

This application is a divisional application of U.S. patent application Ser. No. 13/001,818, filed Dec. 29, 2010, which is a national stage application (under 35 U.S.C. § 371) of PCT/EP2009/003602, filed May 20, 2009, which claims benefit of German Application No. 10 2008 035 413.9, filed Jul. 29, 2008.

The present invention describes novel organic compounds and the use thereof in electronic devices.

The general structure of organic electroluminescent devices is described, for example, in U.S. Pat. No. 4,539,507, U.S. Pat. No. 5,151,629, EP 0676461 and WO 98/27136. However, these devices still exhibit problems for which there is a need for improvement:

1. There is still a need for improvement in the efficiency, especially in the case of fluorescent OLEDs. This applies in particular to dark-blue-emitting OLEDs.
2. A further improvement in the operating lifetime is still desirable, in particular in the case of blue emission.
3. The operating voltage is quite high, especially in the case of fluorescent OLEDs. There is therefore still a need for improvement here in order to improve the power efficiency. This is of major importance, in particular, for mobile applications.
4. Many blue-emitting materials in accordance with the prior art are incompatible with frequently used electron-injection and -transport materials, such as, for example, hydroxyquinolinate/metal complexes (for example Alq, Beq), benzimidazole derivatives, phenanthroline derivatives (for example BCP) or anthracene derivatives, which are mixed with donors, such as alkali or alkaline-earth metals (for example Li, Na, K, Rb or Cs), with inorganic salts thereof (for example LiF or $Cs_2CO_3$) or with organic salts thereof (for example lithium, sodium, potassium, rubidium or caesium quinolinate) and thus produce an excess of electrons in the device. This incompatibility only results in inadequate device lifetimes. The problems frequently occur, in particular, if the blue-emitting material used is a diarylamino derivative of a condensed aromatic compound. However, emitters of this type are the most frequent and hitherto the best blue emitters. Further improvements are therefore desirable here.

The closest prior art for blue-fluorescent emitters are dibenzoindenofluorene derivatives in accordance with WO 07/140847 and monobenzoindenofluorene derivatives in accordance with WO 08/006449. In order to obtain efficient blue emitters from these basic structures, the introduction of one or two diarylamino groups is necessary. Good blue-emitting OLEDs have already been achieved with these compounds. However, further improvements are also desirable here with respect to the efficiency. Whereas these diarylamino-substituted compounds also exhibit very good lifetimes in combination with an undoped electron-transport layer, the lifetime is still inadequate if these compounds are used in combination with a doped electron-transport layer, as described above. Further improvements are therefore also necessary with respect to the lifetime, in particular in combination with doped electron-transport layers which result in an excess of electrons in the device.

Surprisingly, it has been found that compounds in which three aryl or heteroaryl groups are bridged by two indeno bridges or corresponding heterobridges exhibit particularly good properties as blue emitters if, in particular, the sum of the π electrons of the three aromatic or heteroaromatic groups is a least 28. It is not necessary to introduce diarylamino substituents into these compounds since the unsubstituted compounds already exhibit highly efficient dark-blue emission. Furthermore, the compounds result in very good lifetimes in organic electroluminescent devices. The present invention therefore relates to these compounds and to the use thereof in organic electroluminescent devices.

The invention therefore relates to compounds of the formula (1)

formula (1)

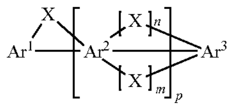

where the following applies to the symbols and indices used:

$Ar^1$, $Ar^2$, $Ar^3$ are on each occurrence, identically or differently, an aryl or heteroaryl group having 5 to 30 aromatic ring atoms, which may be substituted by one or more radicals $R^1$, with the proviso that $Ar^2$ does not stand for anthracene, naphthacene or pentacene;

X is on each occurrence, identically or differently, a group selected from $BR^2$, $C(R^2)_2$, $Si(R^2)_2$, C=O, $C=NR^2$, $C=C(R^2)_2$, O, S, S=O, $SO_2$, $NR^2$, $PR^2$, $P(=O)R^2$ and $P(=S)R^2$;

$R^1$, $R^2$ are on each occurrence, identically or differently, H, D, F, Cl, Br, I, $N(Ar^4)_2$, $C(=O)Ar^4$, $P(=O)(Ar^4)_2$, $S(=O)Ar^4$, $S(=O)_2Ar^4$, $CR^2=CR^2Ar^4$, CHO, $CR^3=C(R^3)_2$, CN, $NO_2$, $Si(R^3)_3$, $B(OR^3)_2$, $B(R^3)_2$, $B(N(R^3)_2)_2$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^3$, where in each case one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)R^3$, SO, $SO_2$, $NR^3$, O, S or $CONR^3$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^3$, or a combination of these systems; two or more substituents $R^1$ or $R^2$ here may also form a mono- or polycyclic, aliphatic or aromatic ring system with one another;

$R^3$ is on each occurrence, identically or differently, H, D or an aliphatic or aromatic hydrocarbon radical having 1 to 20 C atoms;

$Ar^4$ is on each occurrence, identically or differently, an aromatic or heteroaromatic ring system having 5-30 aromatic ring atoms, which may be substituted by one or more non-aromatic radicals $R^1$; two radicals Ar on the same nitrogen or phosphorus atom may also be linked to one another here by a single bond or a bridge X;

m, n are 0 or 1, with the proviso that m+n=1;

p is 1, 2, 3, 4, 5 or 6;

$Ar^1$, $Ar^2$ and X here together form a five-membered ring or a six-membered ring, and $Ar^2$, $Ar^3$ and X together form a five-membered ring or a six-membered ring, with the proviso that either all symbols X in the compound of the formula (1) are bound in a five-membered ring or all symbols X in the compound of the formula (1) are bound in a six-membered ring;

characterised in that the sum of all π electrons in groups $Ar^1$, $Ar^2$ and $Ar^3$ is at least 28 if p=1 and is at least 34 if p=2 and is at least 40 if p=3 and is at least 46 if p=4 and is at least 52 if p=5 and is at least 58 if p=6;

the following compounds are excluded from the invention:

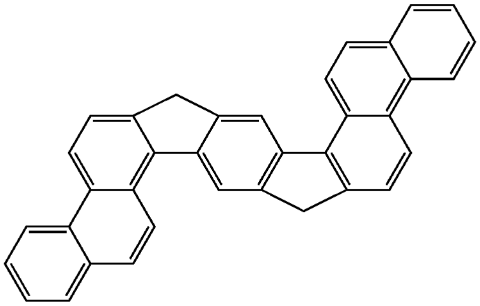

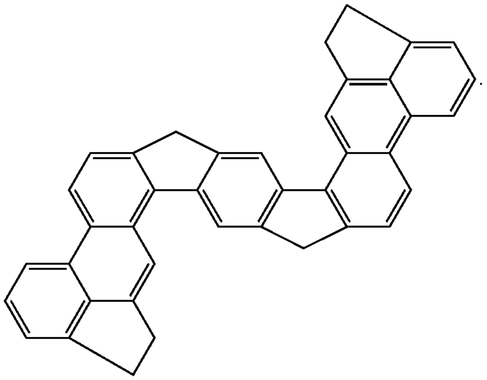

n=0 or m=0 here means that the corresponding group X is not present and that instead hydrogen or a substituent $R^1$ is bonded to the corresponding positions of $Ar^2$ and $Ar^3$.

The determination of the sum of all π electrons in groups $Ar^1$, $Ar^2$ and $Ar^3$ is obvious to the person skilled in the art. Thus, each double bond in an aryl group (where the double bonds are delocalised) stands for two π electrons, meaning that, for example, benzene has 6 π electrons, naphthalene has 10 π electrons, anthracene and phenanthrene have 14 π electrons, pyrene has 16 π electrons, naphthacene, benzanthracene and chrysene have 18 π electrons, and perylene has 20 π electrons. In an aryl group, the number of π electrons corresponds to the number of C atoms in the aromatic ring system. In heteroaromatic compounds, each double bond (the double bonds here are again delocalised) also contributes two it electrons, where these delocalised double bonds can be formed either between two carbon atoms, between carbon and nitrogen or between two nitrogen atoms. Furthermore, in five-membered heteroaryl groups, the heteroatom, which is formally not bonded in a double bond (i.e. for example, the nitrogen in pyrrole, the oxygen in furan or the sulfur in thiophene) likewise contributes two π electrons to the overall π-electron system via the free electron pair. Pyridine, pyrazine, pyrimidine and pyridazine therefore each have 6 π electrons, quinoline and isoquinoline have 10 π electrons, phenanthroline has 14 π electrons, pyrrole, imidazole, pyrazole, thiophene, thiazole and furan each have 6 π electrons, indole, benzimidazole, benzothiophene and benzofuran each have 10 π electrons, and carbazole, dibenzothiophene and dibenzofuran each have 14 π electrons.

It is shown below with reference to the example of phenyl and naphthalene as groups $Ar^1$ and $Ar^2$ what is meant by the formation of a five-membered ring or six-membered ring from the groups $Ar^1$, $Ar^2$ and X:

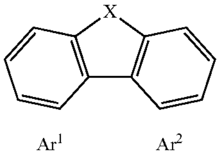

formation of a five-membered ring

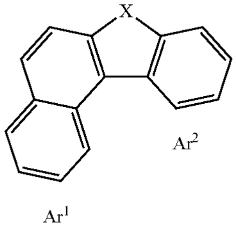

formation of a five-membered ring

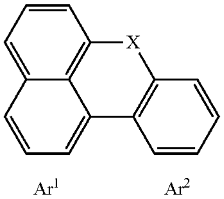

formation of a six-membered ring

With a simple, uncondensed aryl or heteroaryl group, for example with phenyl, it is always only possible to form a five-membered ring. With a condensed aryl or heteroaryl group, for example with naphthalene, the formation of a five-membered ring or six-membered ring is possible, depending on the linking. The same linking principle can be applied correspondingly to other condensed aryl groups or to condensed or uncondensed heteroaryl groups. In a five-membered ring, one edge of the aryl or heteroaryl group $Ar^1$ or $Ar^2$ or $Ar^3$ thus in each case forms a five-membered ring with X. In a six-membered ring, two edges of a condensed aryl or heteroaryl group $Ar^1$ or $Ar^2$ or $Ar^3$ form a six-membered ring together with one edge of a further aryl or heteroaryl group $Ar^1$ or $Ar^2$ or $Ar^3$ and together with X.

In a preferred embodiment of the invention, $Ar^1$, $Ar^2$ and X form a five-membered ring and $Ar^2$, $Ar^3$ and X form a five-membered ring. If the index p=2 or 3, two groups $Ar^2$ preferably also form a five-membered ring together with X.

For the purposes of this invention, an aryl group or heteroaryl group is taken to mean an aromatic group or heteroaromatic group respectively having a common aromatic electron system, where an aryl group contains 6 to 30 C atoms and a heteroaryl group contains 2 to 30 C atoms and a total of at least 5 aromatic ring atoms. The heteroatoms are preferably selected from N, O and/or S. For the purposes of this invention, this can be a single homo- or heterocyclic ring, for example benzene, pyridine, thiophene, etc., or it can be a condensed aryl or heteroaryl group in which at least two aromatic or heteroaromatic rings, for example benzene rings, are fused to one another, i.e. are condensed onto one another by anellation, i.e. have at least one common edge and thus also a common aromatic system. This aryl or heteroaryl group may be substituted or unsubstituted; any substituents present may likewise form further ring systems. Thus, for example, systems such as naphthalene, anthracene, phenanthrene, pyrene, etc., are to be regarded as aryl groups for the purposes of this invention and quinoline, acridine, benzothiophene, carbazole, etc., are to be regarded as heteroaryl groups for the purposes of this invention, while, for example, biphenyl, fluorene, spirobifluorene, etc., are not aryl groups since separate aromatic electron systems are present here.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, a C, N or O atom. Thus, for example, systems such as 9,9'-spirobifluorene, 9,9-diarylfluorene, triarylamine, diaryl ether, etc., are also to be regarded as aromatic ring systems for the purposes of this invention.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl, 2,2,2-trifluoroethyl, ethenyl, propenyl, butenyl, pentenyl, cyclopentenyl, hexenyl, heptynyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{24}$-aryl or -heteroaryl group, which can be monovalent or divalent depending on the use, may in each case also be substituted by the above-mentioned radicals $R^1$ and may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, benzofluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole. In addition to the above-mentioned aryl and heteroaryl groups, aromatic and heteroaromatic ring systems are, for the purposes of this invention, taken to mean, in particular, biphenylene, terphenylene, fluorene, benzofluorene, dibenzofluorene, spirobifluorene, dihydrophenanthrene, tetrahydropyrene, cis- or trans-indenofluorene, cis- or trans-monobenzoindenofluorene or cis- or trans-dibenzoindenofluorene.

In a preferred embodiment of the invention, the index p=1, 2 or 3, particularly preferably 1 or 2, very particularly preferably 1.

In a preferred embodiment of the invention, the sum of all π electrons in groups $Ar^1$, $Ar^2$ and $Ar^3$ is between 28 and 50, particularly preferably between 28 and 46, very particularly preferably between 28 and 42, in particular between 28 and 36, if p=1, and is between 34 and 56, particularly preferably between 34 and 52, very particularly preferably between 34 and 48, in particular between 34 and 40, if p=2, and is between 40 and 62, particularly preferably between 40 and 58, very particularly preferably between 40 and 54, in particular between 40 and 46, if p=3.

Preference is furthermore given to compounds of the formula (1) in which the symbols $Ar^1$, $Ar^2$ and $Ar^3$ stand, identically or differently on each occurrence, for an aryl or heteroaryl group having 5 to 22 aromatic ring atoms, in particular having 5 to 18 aromatic ring atoms. The groups $Ar^1$, $Ar^2$ and $Ar^3$ here are particularly preferably selected, independently of one another, from the group consisting of benzene, naphthalene, anthracene, phenanthrene, fluoranthene, naphthacene, benzanthracene, chrysene, pyrene, benzofluoranthene, triphenylene, perylene, dibenzanthracene, benzopyrene, picene, pentacene, pentaphene, benzophenanthrene, pyridine, pyrazine, pyrimidine, pyridazine, quinoline, isoquinoline, phenanthroline, acridine. The symbols $Ar^1$, $Ar^2$ and $Ar^3$ particularly preferably stand on each occurrence, identically or differently, for an aryl group having 6 to 18 aromatic ring atoms, in particular selected from benzene, naphthalene, anthracene, phenanthrene, fluoranthene, naphthacene, benzanthracene, chrysene, pyrene, benzofluoranthene and triphenylene.

Particularly preferred groups $Ar^1$ and $Ar^3$ which form a five-membered ring with $Ar^2$ are the groups of the formulae (2) to (85) shown below, each of which may be substituted by one or more radicals $R^1$. The symbol * stands for the position of the link from $Ar^1$ or $Ar^3$ to $Ar^2$, and the symbol # stands for the position of the link from $Ar^1$ or $Ar^3$ to X.

formula (2)

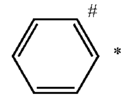

formula (3)

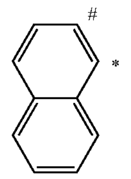

-continued
formula (4)
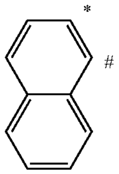
formula (5)
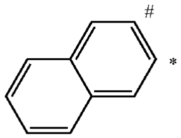
formula (6)
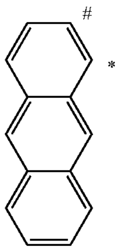
formula (7)
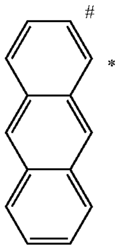
formula (8)
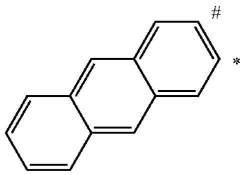
formula (9)
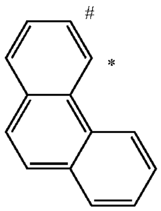
formula (10)
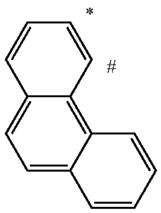
-continued
formula (11)
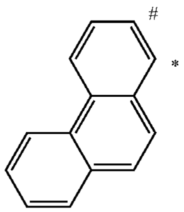
formula (12)
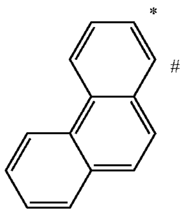
formula (13)
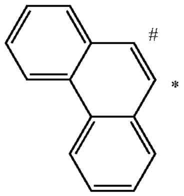
formula (14)
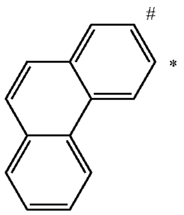
formula (15)
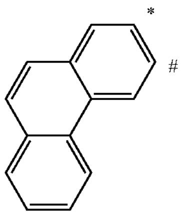
formula (16)
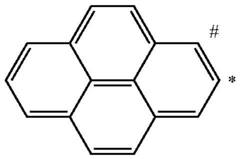
formula (17)
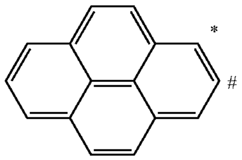

-continued
formula (18)
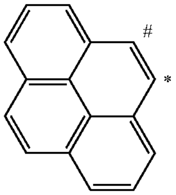
formula (19)
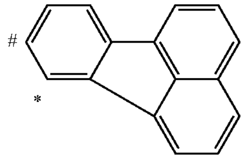
formula (20)
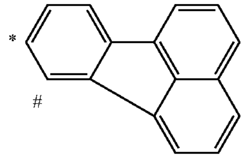
formula (21)
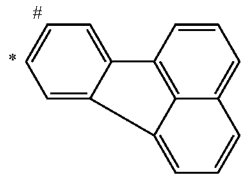
formula (22)
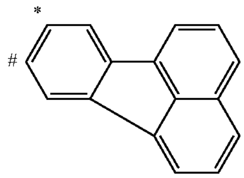
formula (23)
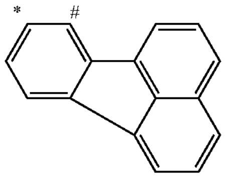
formula (24)
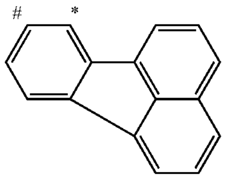
-continued
formula (25)
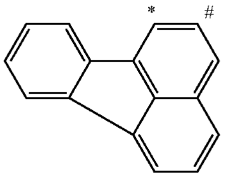
formula (26)
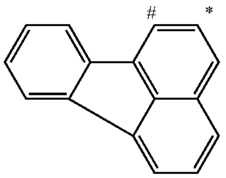
formula (27)
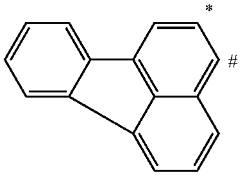
formula (28)
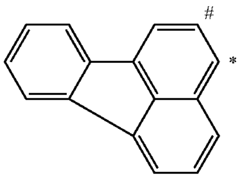
formula (29)
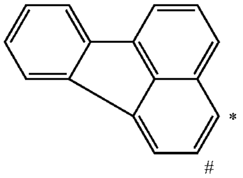
formula (30)
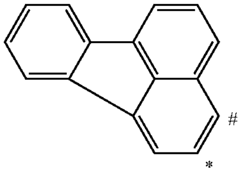
formula (31)
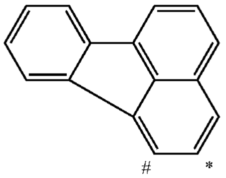
formula (32)
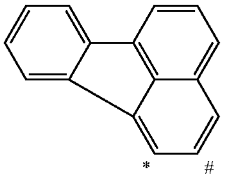

-continued
formula (33)
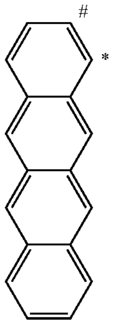
formula (34)
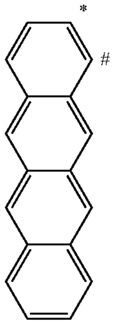
formula (35)
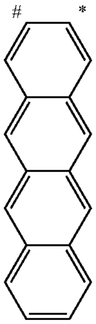
formula (36)
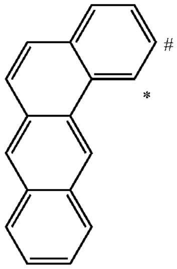
formula (37)
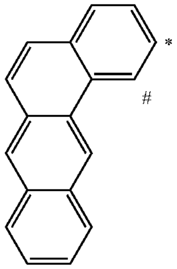
-continued
formula (38)
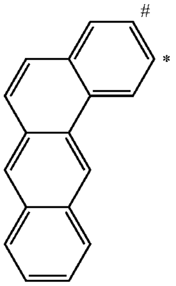
formula (39)
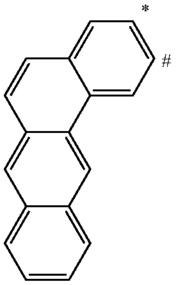
formula (40)
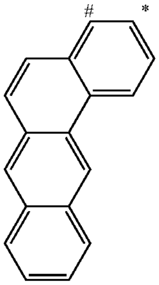
formula (41)
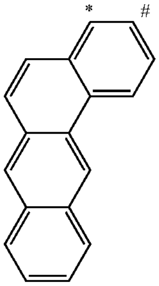
formula (42)
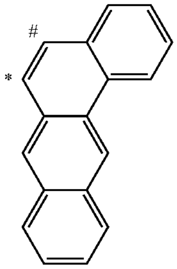

-continued
formula (43)
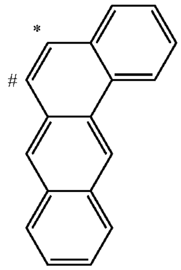
formula (44)
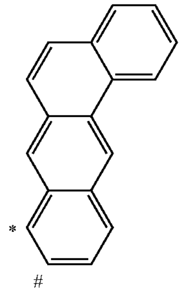
formula (45)
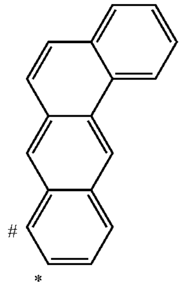
formula (46)
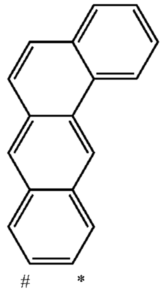
formula (47)
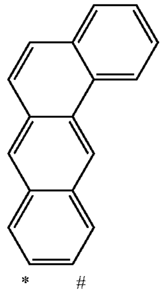
-continued
formula (48)
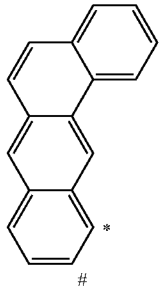
formula (49)
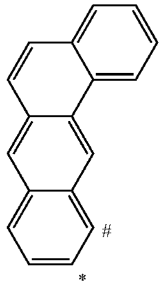
formula (50)
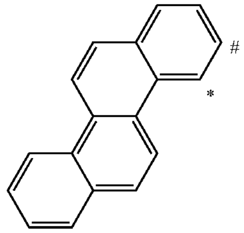
formula (51)
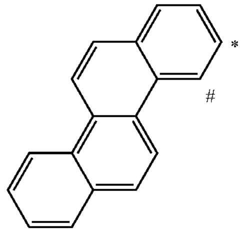
formula (52)
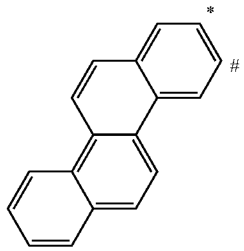
formula (53)
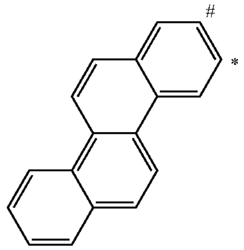

-continued
formula (54)
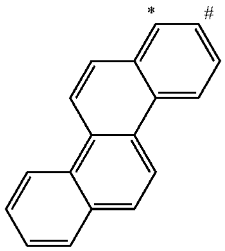
formula (55)
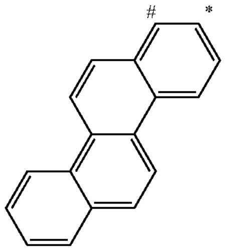
formula (56)
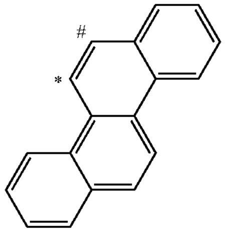
formula (57)
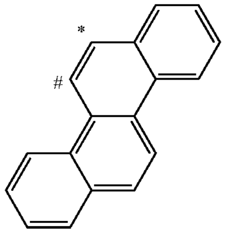
formula (58)
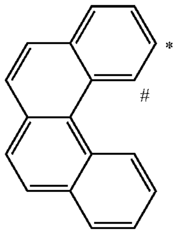
formula (59)
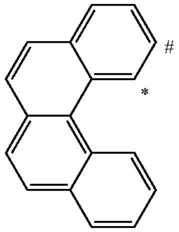
-continued
formula (60)
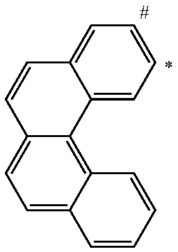
formula (61)
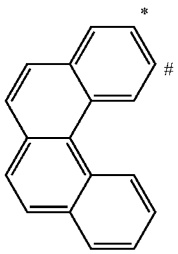
formula (62)
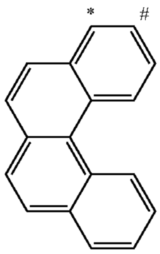
formula (63)
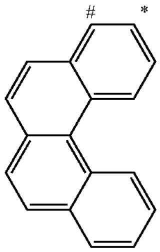
formula (64)
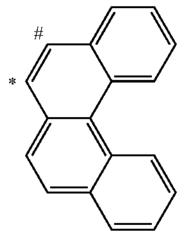
formula (65)
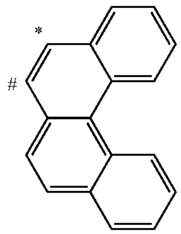

-continued
formula (66)
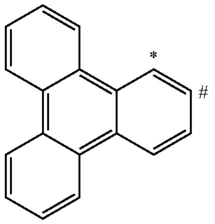
formula (67)
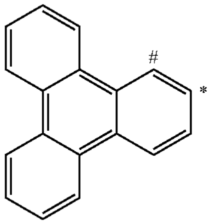
formula (68)
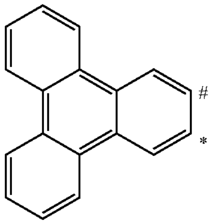
formula (69)
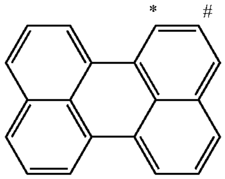
formula (70)
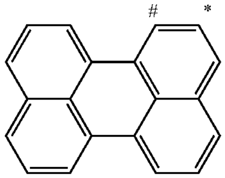
formula (71)
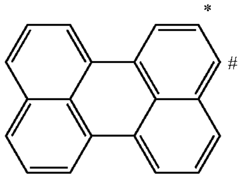
formula (72)
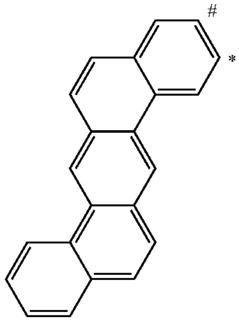
-continued
formula (73)
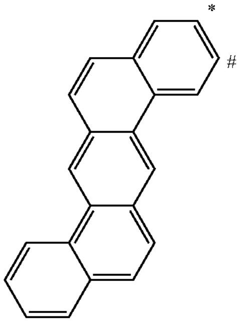
formula (74)
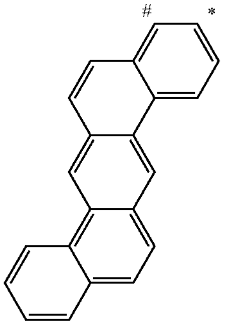
formula (75)
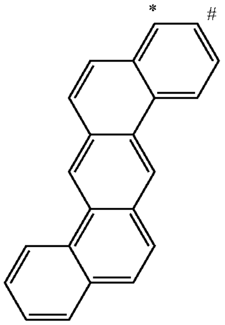
formula (76)
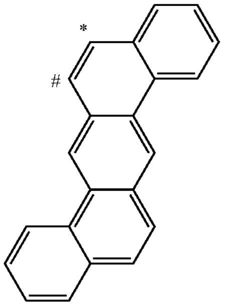
formula (77)
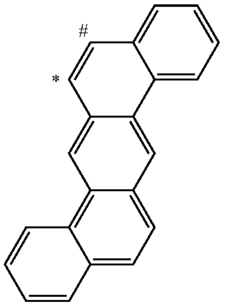

-continued formula (78)

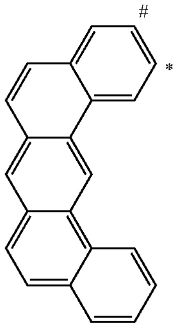

formula (79)

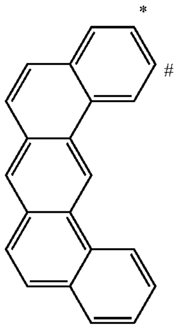

formula (80)

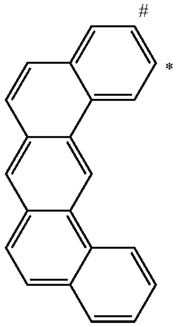

formula (81)

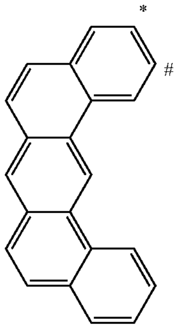

-continued formula (82)

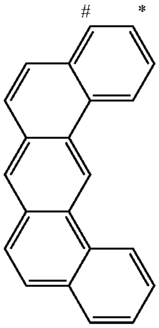

formula (83)

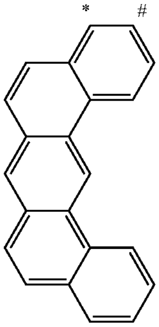

formula (84)

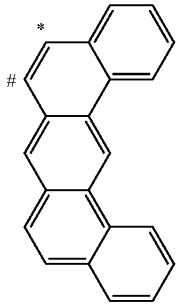

formula (85)

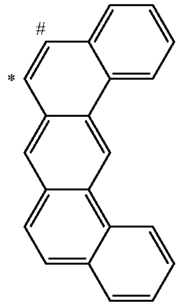

Preference is likewise given to the groups $Ar^1$ and $Ar^3$ mentioned above which form a six-membered ring with $Ar^2$. The formation of a six-membered ring takes place via two groups in the peri position, as depicted by way of example below with reference to the example of an anthracene group:

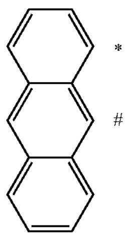

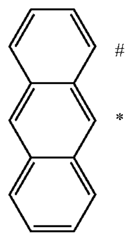

Particularly preferred groups $Ar^2$ are the groups of the formulae (86) to (110) shown below, each of which may be substituted by one or more radicals $R^1$. The symbol * stands for the position of the link from $Ar^2$ to $Ar^1$ or $Ar^3$ and the symbol # stands for the position of the link from $Ar^2$ to X.

formula (86)

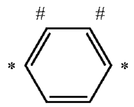

formula (87)

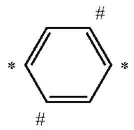

formula (88)

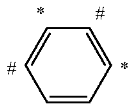

formula (89)

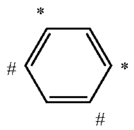

formula (90)

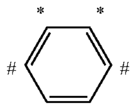

formula (91)

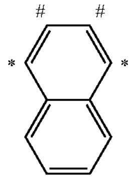

formula (92)

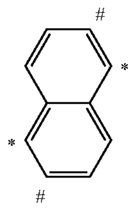

-continued

Formula (93)

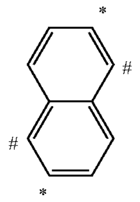

Formula (94)

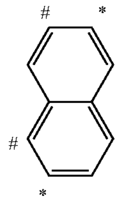

formula (95)

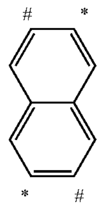

formula (96)

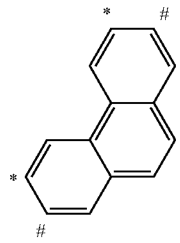

formula (97)

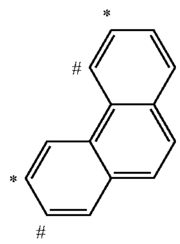

formula (98)

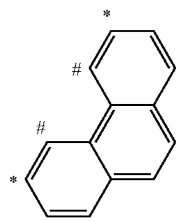

-continued
formula (99)
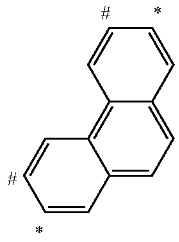
formula (100)
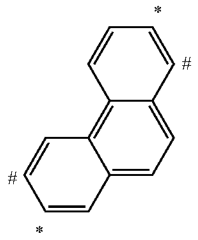
formula (101)
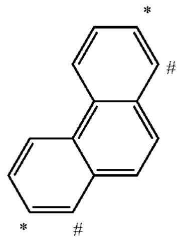
formula (102)
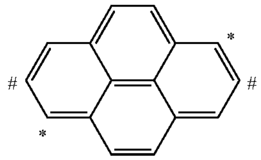
formula (103)
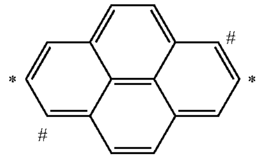
formula (104)
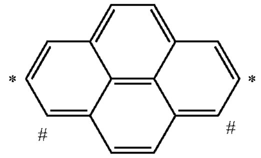
formula (105)
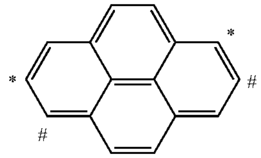
-continued
formula (106)
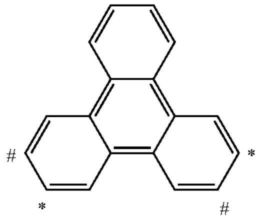
formula (107)
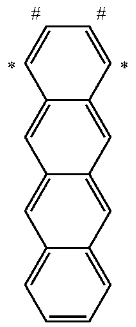
formula (108)
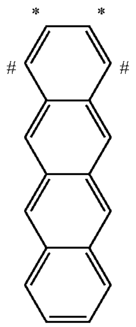
formula (109)
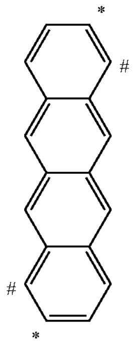
formula (110)
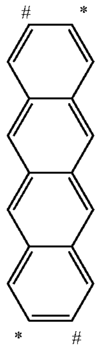

Entirely analogously, groups $Ar^2$ which form a six-membered ring with $Ar^1$ or $Ar^3$ and X are also possible here.

Preference is furthermore given to compounds in which at least one of the groups $Ar^1$, $Ar^2$ and $Ar^3$ has at least three condensed rings, i.e. at least 14 π electrons. Particularly preferably, at least one of the groups $Ar^1$, $Ar^2$ and $Ar^3$ has at least 4 condensed rings, i.e. at least 16 π electrons. Very particularly preferably, at least one of the groups $Ar^1$, $Ar^2$ and $Ar^3$ has at least 4 condensed rings, i.e. at least 16 π electrons, and at least one of the other two groups $Ar^1$, $Ar^2$ or $Ar^3$ has at least 2 condensed rings, i.e. at least 10 π electrons.

Preferred combinations of $Ar^1$, $Ar^2$ and $Ar^3$ are the combinations shown in Table 1 and Table 2. $Ar^1$, $Ar^2$ and $Ar^3$ here may also be substituted by one or more radicals $R^1$.

TABLE 1

| Ar1 | Ar2 | Ar3 |
|---|---|---|
| Benzene | Benzene | Pyrene |
| Benzene | Benzene | Naphthacene |
| Benzene | Benzene | Benzathracene |
| Benzene | Benzene | Chrysene |
| Benzene | Benzene | Benzophenanthrene |
| Benzene | Benzene | Fluoranthene |
| Benzene | Benzene | Triphenylene |
| Benzene | Naphthalene | Anthracene |
| Benzene | Naphthalene | Phenanthrene |
| Benzene | Naphthalene | Pyrene |
| Benzene | Naphthalene | Naphthacene |
| Benzene | Naphthalene | Benzathracene |
| Benzene | Naphthalene | Chrysene |
| Benzene | Naphthalene | Benzophenanthrene |
| Benzene | Naphthalene | Fluoranthene |
| Benzene | Naphthalene | Triphenylene |
| Naphthalene | Benzene | Anthracene |
| Naphthalene | Benzene | Phenanthrene |
| Naphthalene | Benzene | Pyrene |
| Naphthalene | Benzene | Naphthacene |
| Naphthalene | Benzene | Benzathracene |
| Naphthalene | Benzene | Chrysene |
| Naphthalene | Benzene | Benzophenanthrene |
| Naphthalene | Benzene | Fluoranthene |
| Naphthalene | Benzene | Triphenylene |
| Naphthalene | Naphthalene | Naphthalene |
| Naphthalene | Naphthalene | Anthracene |
| Naphthalene | Naphthalene | Phenanthrene |
| Naphthalene | Naphthalene | Pyrene |
| Naphthalene | Naphthalene | Naphthacene |
| Naphthalene | Naphthalene | Benzathracene |
| Naphthalene | Naphthalene | Chrysene |
| Naphthalene | Naphthalene | Benzophenanthrene |
| Naphthalene | Naphthalene | Fluoranthene |
| Naphthalene | Naphthalene | Triphenylene |
| Anthracene | Benzene | Anthracene |
| Anthracene | Benzene | Phenanthrene |
| Anthracene | Benzene | Pyrene |
| Anthracene | Benzene | Naphthacene |
| Anthracene | Benzene | Benzathracene |
| Anthracene | Benzene | Chrysene |
| Anthracene | Benzene | Benzophenanthrene |
| Anthracene | Benzene | Fluoranthene |
| Anthracene | Benzene | Triphenylene |
| Anthracene | Naphthalene | Anthracene |
| Anthracene | Naphthalene | Phenanthrene |
| Anthracene | Naphthalene | Pyrene |
| Anthracene | Naphthalene | Naphthacene |
| Anthracene | Naphthalene | Benzathracene |
| Anthracene | Naphthalene | Chrysene |
| Anthracene | Naphthalene | Benzophenanthrene |
| Anthracene | Naphthalene | Fluoranthene |
| Anthracene | Naphthalene | Triphenylene |
| Phenanthrene | Benzene | Phenanthrene |
| Phenanthrene | Benzene | Pyrene |
| Phenanthrene | Benzene | Naphthacene |
| Phenanthrene | Benzene | Benzathracene |
| Phenanthrene | Benzene | Chrysene |

TABLE 1-continued

| Ar1 | Ar2 | Ar3 |
|---|---|---|
| Phenanthrene | Benzene | Benzophenanthrene |
| Phenanthrene | Benzene | Fluoranthene |
| Phenanthrene | Benzene | Triphenylene |
| Phenanthrene | Naphthalene | Phenanthrene |
| Phenanthrene | Naphthalene | Pyrene |
| Phenanthrene | Naphthalene | Naphthacene |
| Phenanthrene | Naphthalene | Benzathracene |
| Phenanthrene | Naphthalene | Chrysene |
| Phenanthrene | Naphthalene | Benzophenanthrene |
| Phenanthrene | Naphthalene | Fluoranthene |
| Phenanthrene | Naphthalene | Triphenylene |
| Pyrene | Benzene | Pyrene |
| Pyrene | Benzene | Naphthacene |
| Pyrene | Benzene | Benzathracene |
| Pyrene | Benzene | Chrysene |
| Pyrene | Benzene | Benzophenanthrene |
| Pyrene | Benzene | Fluoranthene |
| Pyrene | Benzene | Triphenylene |
| Pyrene | Naphthalene | Pyrene |
| Pyrene | Naphthalene | Naphthacene |
| Pyrene | Naphthalene | Benzathracene |
| Pyrene | Naphthalene | Chrysene |
| Pyrene | Naphthalene | Benzophenanthrene |
| Pyrene | Naphthalene | Fluoranthene |
| Pyrene | Naphthalene | Triphenylene |
| Naphthacene | Benzene | Naphthacene |
| Naphthacene | Benzene | Benzathracene |
| Naphthacene | Benzene | Chrysene |
| Naphthacene | Benzene | Benzophenanthrene |
| Naphthacene | Benzene | Fluoranthene |
| Naphthacene | Benzene | Triphenylene |
| Naphthacene | Naphthalene | Naphthacene |
| Naphthacene | Naphthalene | Benzathracene |
| Naphthacene | Naphthalene | Chrysene |
| Naphthacene | Naphthalene | Benzophenanthrene |
| Naphthacene | Naphthalene | Fluoranthene |
| Naphthacene | Naphthalene | Triphenylene |
| Benzathracene | Benzene | Benzathracene |
| Benzathracene | Benzene | Chrysene |
| Benzathracene | Benzene | Benzophenanthrene |
| Benzathracene | Benzene | Fluoranthene |
| Benzathracene | Benzene | Triphenylene |
| Benzathracene | Naphthalene | Benzathracene |
| Benzathracene | Naphthalene | Chrysene |
| Benzathracene | Naphthalene | Benzophenanthrene |
| Benzathracene | Naphthalene | Fluoranthene |
| Benzathracene | Naphthalene | Triphenylene |
| Chrysene | Benzene | Chrysene |
| Chrysene | Benzene | Benzophenanthrene |
| Chrysene | Benzene | Fluoranthene |
| Chrysene | Benzene | Triphenylene |
| Chrysene | Naphthalene | Chrysene |
| Chrysene | Naphthalene | Benzophenanthrene |
| Chrysene | Naphthalene | Fluoranthene |
| Chrysene | Naphthalene | Triphenylene |
| Benzophenanthrene | Benzene | Benzophenanthrene |
| Benzophenanthrene | Benzene | Fluoranthene |
| Benzophenanthrene | Benzene | Triphenylene |
| Benzophenanthrene | Naphthalene | Benzophenanthrene |
| Benzophenanthrene | Naphthalene | Fluoranthene |
| Benzophenanthrene | Naphthalene | Triphenylene |
| Fluoranthene | Benzene | Fluoranthene |
| Fluoranthene | Benzene | Triphenylene |
| Fluoranthene | Naphthalene | Fluoranthene |
| Fluoranthene | Naphthalene | Triphenylene |
| Triphenylene | Benzene | Triphenylene |
| Triphenylene | Naphthalene | Triphenylene |

The above-mentioned units are preferably selected from the units of the formulae (2) to (110). Thus, for $Ar^1$ or $Ar^3$ in Table 1, the benzene is selected from the formula (2), the naphthalene is selected from structures of the formulae (3) to (5), the pyrene is selected from structures of the formulae (16) to (18), the naphthacene is selected from structures of the formulae (33) to (35), the benzanthracene is selected from structures of the formulae (36) to (49), the chrysene is selected from structures of the formulae (50) to (57), the benzophenanthrene is selected from structures of the formulae (58) to (65), the fluoranthene is selected from structures of the formulae (19) to (32) and the triphenylene is selected from structures of the formulae (66) to (68). For the group $Ar^2$, the benzene is selected from structures of the formulae (96) to (100) and the naphthalene is selected from structures of the formulae (101) to (105). These structures may each be substituted by one or more radicals $R^1$.

TABLE 2

| Ar1 | Ar2 | Ar3 |
|---|---|---|
| Benzene | Phenanthrene | Naphthalene |
| Benzene | Phenanthrene | Anthracene |
| Benzene | Phenanthrene | Phenanthrene |
| Benzene | Phenanthrene | Pyrene |
| Benzene | Phenanthrene | Naphthacene |
| Benzene | Phenanthrene | Benzanthracene |
| Benzene | Phenanthrene | Chrysene |
| Benzene | Phenanthrene | Benzophenanthrene |
| Benzene | Phenanthrene | Fluoranthene |
| Benzene | Phenanthrene | Triphenylene |
| Benzene | Pyrene | Benzene |
| Benzene | Pyrene | Naphthalene |
| Benzene | Pyrene | Anthracene |
| Benzene | Pyrene | Phenanthrene |
| Benzene | Pyrene | Pyrene |
| Benzene | Pyrene | Naphthacene |
| Benzene | Pyrene | Benzanthracene |
| Benzene | Pyrene | Chrysene |
| Benzene | Pyrene | Benzophenanthrene |
| Benzene | Pyrene | Fluoranthene |
| Benzene | Pyrene | Triphenylene |
| Benzene | Benzanthracene | Benzene |
| Benzene | Benzanthracene | Naphthalene |
| Benzene | Benzanthracene | Anthracene |
| Benzene | Benzanthracene | Phenanthrene |
| Benzene | Benzanthracene | Pyrene |
| Benzene | Benzanthracene | Naphthacene |
| Benzene | Benzanthracene | Benzanthracene |
| Benzene | Benzanthracene | Chrysene |
| Benzene | Benzanthracene | Benzophenanthrene |
| Benzene | Benzanthracene | Fluoranthene |
| Benzene | Benzanthracene | Triphenylene |
| Benzene | Chrysene | Benzene |
| Benzene | Chrysene | Naphthalene |
| Benzene | Chrysene | Anthracene |
| Benzene | Chrysene | Phenanthrene |
| Benzene | Chrysene | Pyrene |
| Benzene | Chrysene | Naphthacene |
| Benzene | Chrysene | Benzanthracene |
| Benzene | Chrysene | Chrysene |
| Benzene | Chrysene | Benzophenanthrene |
| Benzene | Chrysene | Fluoranthene |
| Benzene | Chrysene | Triphenylene |
| Benzene | Benzophenanthrene | Benzene |
| Benzene | Benzophenanthrene | Naphthalene |
| Benzene | Benzophenanthrene | Anthracene |
| Benzene | Benzophenanthrene | Phenanthrene |
| Benzene | Benzophenanthrene | Pyrene |
| Benzene | Benzophenanthrene | Naphthacene |
| Benzene | Benzophenanthrene | Benzanthracene |
| Benzene | Benzophenanthrene | Chrysene |
| Benzene | Benzophenanthrene | Benzophenanthrene |
| Benzene | Benzophenanthrene | Fluoranthene |
| Benzene | Benzophenanthrene | Triphenylene |
| Benzene | Fluoranthene | Benzene |
| Benzene | Fluoranthene | Naphthalene |
| Benzene | Fluoranthene | Anthracene |
| Benzene | Fluoranthene | Phenanthrene |
| Benzene | Fluoranthene | Pyrene |
| Benzene | Fluoranthene | Naphthacene |
| Benzene | Fluoranthene | Benzanthracene |
| Benzene | Fluoranthene | Chrysene |
| Benzene | Fluoranthene | Benzophenanthrene |
| Benzene | Fluoranthene | Fluoranthene |
| Benzene | Fluoranthene | Triphenylene |
| Benzene | Triphenylene | Benzene |

TABLE 2-continued

| Ar1 | Ar2 | Ar3 |
|---|---|---|
| Benzene | Triphenylene | Naphthalene |
| Benzene | Triphenylene | Anthracene |
| Benzene | Triphenylene | Phenanthrene |
| Benzene | Triphenylene | Pyrene |
| Benzene | Triphenylene | Naphthacene |
| Benzene | Triphenylene | Benzanthracene |
| Benzene | Triphenylene | Chrysene |
| Benzene | Triphenylene | Benzophenanthrene |
| Benzene | Triphenylene | Fluoranthene |
| Benzene | Triphenylene | Triphenylene |
| Naphthalene | Phenanthrene | Benzene |
| Naphthalene | Phenanthrene | Naphthalene |
| Naphthalene | Phenanthrene | Anthracene |
| Naphthalene | Phenanthrene | Phenanthrene |
| Naphthalene | Phenanthrene | Pyrene |
| Naphthalene | Phenanthrene | Naphthacene |
| Naphthalene | Phenanthrene | Benzanthracene |
| Naphthalene | Phenanthrene | Chrysene |
| Naphthalene | Phenanthrene | Benzophenanthrene |
| Naphthalene | Phenanthrene | Fluoranthene |
| Naphthalene | Phenanthrene | Triphenylene |
| Naphthalene | Pyrene | Benzene |
| Naphthalene | Pyrene | Naphthalene |
| Naphthalene | Pyrene | Anthracene |
| Naphthalene | Pyrene | Phenanthrene |
| Naphthalene | Pyrene | Pyrene |
| Naphthalene | Pyrene | Naphthacene |
| Naphthalene | Pyrene | Benzanthracene |
| Naphthalene | Pyrene | Chrysene |
| Naphthalene | Pyrene | Benzophenanthrene |
| Naphthalene | Pyrene | Fluoranthene |
| Naphthalene | Pyrene | Triphenylene |
| Naphthalene | Benzanthracene | Benzene |
| Naphthalene | Benzanthracene | Naphthalene |
| Naphthalene | Benzanthracene | Anthracene |
| Naphthalene | Benzanthracene | Phenanthrene |
| Naphthalene | Benzanthracene | Pyrene |
| Naphthalene | Benzanthracene | Naphthacene |
| Naphthalene | Benzanthracene | Benzanthracene |
| Naphthalene | Benzanthracene | Chrysene |
| Naphthalene | Benzanthracene | Benzophenanthrene |
| Naphthalene | Benzanthracene | Fluoranthene |
| Naphthalene | Benzanthracene | Triphenylene |
| Naphthalene | Chrysene | Benzene |
| Naphthalene | Chrysene | Naphthalene |
| Naphthalene | Chrysene | Anthracene |
| Naphthalene | Chrysene | Phenanthrene |
| Naphthalene | Chrysene | Pyrene |
| Naphthalene | Chrysene | Naphthacene |
| Naphthalene | Chrysene | Benzanthracene |
| Naphthalene | Chrysene | Chrysene |
| Naphthalene | Chrysene | Benzophenanthrene |
| Naphthalene | Chrysene | Fluoranthene |
| Naphthalene | Chrysene | Triphenylene |
| Naphthalene | Benzophenanthrene | Benzene |
| Naphthalene | Benzophenanthrene | Naphthalene |
| Naphthalene | Benzophenanthrene | Anthracene |
| Naphthalene | Benzophenanthrene | Phenanthrene |
| Naphthalene | Benzophenanthrene | Pyrene |
| Naphthalene | Benzophenanthrene | Naphthacene |
| Naphthalene | Benzophenanthrene | Benzanthracene |
| Naphthalene | Benzophenanthrene | Chrysene |
| Naphthalene | Benzophenanthrene | Benzophenanthrene |
| Naphthalene | Benzophenanthrene | Fluoranthene |
| Naphthalene | Benzophenanthrene | Triphenylene |
| Naphthalene | Fluoranthene | Benzene |
| Naphthalene | Fluoranthene | Naphthalene |
| Naphthalene | Fluoranthene | Anthracene |
| Naphthalene | Fluoranthene | Phenanthrene |
| Naphthalene | Fluoranthene | Pyrene |
| Naphthalene | Fluoranthene | Naphthacene |
| Naphthalene | Fluoranthene | Benzanthracene |
| Naphthalene | Fluoranthene | Chrysene |
| Naphthalene | Fluoranthene | Benzophenanthrene |
| Naphthalene | Fluoranthene | Fluoranthene |
| Naphthalene | Fluoranthene | Triphenylene |
| Naphthalene | Triphenylene | Benzene |
| Naphthalene | Triphenylene | Naphthalene |

TABLE 2-continued

| Ar1 | Ar2 | Ar3 |
|---|---|---|
| Naphthalene | Triphenylene | Anthracene |
| Naphthalene | Triphenylene | Phenanthrene |
| Naphthalene | Triphenylene | Pyrene |
| Naphthalene | Triphenylene | Naphthacene |
| Naphthalene | Triphenylene | Benzanthracene |
| Naphthalene | Triphenylene | Chrysene |
| Naphthalene | Triphenylene | Benzophenanthrene |
| Naphthalene | Triphenylene | Fluoranthene |
| Naphthalene | Triphenylene | Triphenylene |

For $Ar^1$ and $Ar^3$ in Table 2, the benzene is a group of the formula (2), and the naphthalene is selected from structures of the formulae (3) to (5). For the group $Ar^2$, the pyrene is selected from structures of the formulae (112) to (115), the naphthacene is selected from structures of the formulae (117) to (120), and the triphenylene is selected from structures of the formula (116). These structures may each be substituted by one or more radicals $R^1$.

Specific particularly preferred combinations of $Ar^1$, $Ar^2$ and $Ar^3$ are revealed, for example, by Table 3 below. The bridges X for these structures are particularly preferably $C(R^2)_2$ groups. Very particularly preferably, both bridges X stand for $C(CH_3)_2$ or both bridges X stand for $C(phenyl)_2$ or one bridge X stands for $C(CH_3)_2$ and the other bridge X stands for $C(phenyl)_2$. The groups $Ar^1$, $Ar^2$ and $Ar^3$ here may be substituted by one or more radicals $R^1$, but are preferably unsubstituted.

TABLE 3

| No. | Ar1 | Ar2 | Ar3 |
|---|---|---|---|
| 1 | Formula (2) | Formula (86) | Formula (17) |
| 2 | Formula (2) | Formula (86) | Formula (28) |
| 3 | Formula (2) | Formula (86) | Formula (41) |
| 4 | Formula (2) | Formula (87) | Formula (17) |
| 5 | Formula (2) | Formula (87) | Formula (28) |
| 6 | Formula (2) | Formula (87) | Formula (41) |
| 7 | Formula (2) | Formula (91) | Formula (7) |
| 8 | Formula (2) | Formula (91) | Formula (8) |
| 9 | Formula (2) | Formula (91) | Formula (13) |
| 10 | Formula (2) | Formula (91) | Formula (17) |
| 11 | Formula (2) | Formula (91) | Formula (28) |
| 12 | Formula (2) | Formula (91) | Formula (41) |
| 13 | Formula (2) | Formula (93) | Formula (7) |
| 14 | Formula (2) | Formula (93) | Formula (8) |
| 15 | Formula (2) | Formula (93) | Formula (13) |
| 16 | Formula (2) | Formula (93) | Formula (17) |
| 17 | Formula (2) | Formula (93) | Formula (28) |
| 18 | Formula (2) | Formula (93) | Formula (41) |
| 19 | Formula (2) | Formula (95) | Formula (7) |
| 20 | Formula (2) | Formula (95) | Formula (8) |
| 21 | Formula (2) | Formula (95) | Formula (13) |
| 22 | Formula (2) | Formula (95) | Formula (17) |
| 23 | Formula (2) | Formula (95) | Formula (28) |
| 24 | Formula (2) | Formula (95) | Formula (41) |
| 25 | Formula (2) | Formula (102) | Formula (2) |
| 26 | Formula (2) | Formula (102) | Formula (3) |
| 27 | Formula (2) | Formula (102) | Formula (4) |
| 28 | Formula (2) | Formula (102) | Formula (7) |
| 29 | Formula (2) | Formula (102) | Formula (8) |
| 30 | Formula (2) | Formula (102) | Formula (13) |
| 31 | Formula (2) | Formula (102) | Formula (17) |
| 32 | Formula (2) | Formula (102) | Formula (28) |
| 33 | Formula (2) | Formula (102) | Formula (41) |
| 34 | Formula (3) | Formula (86) | Formula (7) |
| 35 | Formula (3) | Formula (86) | Formula (8) |
| 36 | Formula (3) | Formula (86) | Formula (13) |
| 37 | Formula (3) | Formula (86) | Formula (17) |
| 38 | Formula (3) | Formula (86) | Formula (28) |
| 39 | Formula (3) | Formula (86) | Formula (41) |
| 40 | Formula (3) | Formula (87) | Formula (7) |

TABLE 3-continued

| No. | Ar1 | Ar2 | Ar3 |
|---|---|---|---|
| 41 | Formula (3) | Formula (87) | Formula (8) |
| 42 | Formula (3) | Formula (87) | Formula (13) |
| 43 | Formula (3) | Formula (87) | Formula (17) |
| 44 | Formula (3) | Formula (87) | Formula (28) |
| 45 | Formula (3) | Formula (87) | Formula (41) |
| 46 | Formula (3) | Formula (91) | Formula (3) |
| 47 | Formula (3) | Formula (91) | Formula (4) |
| 48 | Formula (3) | Formula (91) | Formula (7) |
| 49 | Formula (3) | Formula (91) | Formula (8) |
| 50 | Formula (3) | Formula (91) | Formula (13) |
| 51 | Formula (3) | Formula (91) | Formula (17) |
| 52 | Formula (3) | Formula (91) | Formula (28) |
| 52 | Formula (3) | Formula (91) | Formula (41) |
| 53 | Formula (3) | Formula (93) | Formula (3) |
| 54 | Formula (3) | Formula (93) | Formula (4) |
| 55 | Formula (3) | Formula (93) | Formula (7) |
| 56 | Formula (3) | Formula (93) | Formula (8) |
| 57 | Formula (3) | Formula (93) | Formula (13) |
| 58 | Formula (3) | Formula (93) | Formula (17) |
| 59 | Formula (3) | Formula (93) | Formula (28) |
| 60 | Formula (3) | Formula (93) | Formula (41) |
| 61 | Formula (3) | Formula (95) | Formula (3) |
| 62 | Formula (3) | Formula (95) | Formula (4) |
| 63 | Formula (3) | Formula (95) | Formula (7) |
| 64 | Formula (3) | Formula (95) | Formula (8) |
| 65 | Formula (3) | Formula (95) | Formula (13) |
| 66 | Formula (3) | Formula (95) | Formula (17) |
| 67 | Formula (3) | Formula (95) | Formula (28) |
| 68 | Formula (3) | Formula (95) | Formula (41) |
| 69 | Formula (3) | Formula (102) | Formula (2) |
| 70 | Formula (3) | Formula (102) | Formula (3) |
| 71 | Formula (3) | Formula (102) | Formula (4) |
| 72 | Formula (3) | Formula (102) | Formula (7) |
| 73 | Formula (3) | Formula (102) | Formula (8) |
| 74 | Formula (3) | Formula (102) | Formula (13) |
| 75 | Formula (3) | Formula (102) | Formula (17) |
| 76 | Formula (3) | Formula (102) | Formula (28) |
| 77 | Formula (3) | Formula (102) | Formula (41) |
| 78 | Formula (4) | Formula (86) | Formula (7) |
| 79 | Formula (4) | Formula (86) | Formula (8) |
| 80 | Formula (4) | Formula (86) | Formula (13) |
| 81 | Formula (4) | Formula (86) | Formula (17) |
| 82 | Formula (4) | Formula (86) | Formula (28) |
| 83 | Formula (4) | Formula (86) | Formula (41) |
| 84 | Formula (4) | Formula (87) | Formula (7) |
| 85 | Formula (4) | Formula (87) | Formula (8) |
| 86 | Formula (4) | Formula (87) | Formula (13) |
| 87 | Formula (4) | Formula (87) | Formula (17) |
| 88 | Formula (4) | Formula (87) | Formula (28) |
| 89 | Formula (4) | Formula (87) | Formula (41) |
| 90 | Formula (4) | Formula (91) | Formula (3) |
| 91 | Formula (4) | Formula (91) | Formula (4) |
| 92 | Formula (4) | Formula (91) | Formula (7) |
| 93 | Formula (4) | Formula (91) | Formula (8) |
| 94 | Formula (4) | Formula (91) | Formula (13) |
| 95 | Formula (4) | Formula (91) | Formula (17) |
| 96 | Formula (4) | Formula (91) | Formula (28) |
| 97 | Formula (4) | Formula (91) | Formula (41) |
| 98 | Formula (4) | Formula (93) | Formula (2) |
| 99 | Formula (4) | Formula (93) | Formula (3) |
| 100 | Formula (4) | Formula (93) | Formula (4) |
| 101 | Formula (4) | Formula (93) | Formula (7) |
| 102 | Formula (4) | Formula (93) | Formula (8) |
| 103 | Formula (4) | Formula (93) | Formula (13) |
| 104 | Formula (4) | Formula (93) | Formula (17) |
| 105 | Formula (4) | Formula (93) | Formula (28) |
| 106 | Formula (4) | Formula (93) | Formula (41) |
| 107 | Formula (4) | Formula (95) | Formula (2) |
| 108 | Formula (4) | Formula (95) | Formula (3) |
| 109 | Formula (4) | Formula (95) | Formula (4) |
| 110 | Formula (4) | Formula (95) | Formula (7) |
| 111 | Formula (4) | Formula (95) | Formula (8) |
| 112 | Formula (4) | Formula (95) | Formula (13) |
| 113 | Formula (4) | Formula (95) | Formula (17) |
| 114 | Formula (4) | Formula (95) | Formula (28) |
| 115 | Formula (4) | Formula (95) | Formula (41) |
| 116 | Formula (4) | Formula (102) | Formula (2) |
| 117 | Formula (4) | Formula (102) | Formula (3) |

TABLE 3-continued

| No. | Ar1 | Ar2 | Ar3 |
|---|---|---|---|
| 118 | Formula (4) | Formula (102) | Formula (4) |
| 119 | Formula (4) | Formula (102) | Formula (7) |
| 120 | Formula (4) | Formula (102) | Formula (8) |
| 121 | Formula (4) | Formula (102) | Formula (13) |
| 122 | Formula (4) | Formula (102) | Formula (17) |
| 123 | Formula (4) | Formula (102) | Formula (28) |
| 124 | Formula (4) | Formula (102) | Formula (41) |
| 125 | Formula (7) | Formula (86) | Formula (3) |
| 126 | Formula (7) | Formula (86) | Formula (4) |
| 127 | Formula (7) | Formula (86) | Formula (7) |
| 128 | Formula (7) | Formula (86) | Formula (8) |
| 129 | Formula (7) | Formula (86) | Formula (13) |
| 130 | Formula (7) | Formula (86) | Formula (17) |
| 131 | Formula (7) | Formula (86) | Formula (28) |
| 132 | Formula (7) | Formula (86) | Formula (41) |
| 133 | Formula (7) | Formula (87) | Formula (3) |
| 134 | Formula (7) | Formula (87) | Formula (4) |
| 135 | Formula (7) | Formula (87) | Formula (7) |
| 136 | Formula (7) | Formula (87) | Formula (8) |
| 137 | Formula (7) | Formula (87) | Formula (13) |
| 138 | Formula (7) | Formula (87) | Formula (17) |
| 139 | Formula (7) | Formula (87) | Formula (28) |
| 140 | Formula (7) | Formula (87) | Formula (41) |
| 141 | Formula (7) | Formula (91) | Formula (2) |
| 142 | Formula (7) | Formula (91) | Formula (3) |
| 143 | Formula (7) | Formula (91) | Formula (4) |
| 144 | Formula (7) | Formula (91) | Formula (7) |
| 145 | Formula (7) | Formula (91) | Formula (8) |
| 146 | Formula (7) | Formula (91) | Formula (13) |
| 147 | Formula (7) | Formula (91) | Formula (17) |
| 148 | Formula (7) | Formula (91) | Formula (28) |
| 149 | Formula (7) | Formula (91) | Formula (41) |
| 150 | Formula (7) | Formula (93) | Formula (2) |
| 151 | Formula (7) | Formula (93) | Formula (3) |
| 152 | Formula (7) | Formula (93) | Formula (4) |
| 153 | Formula (7) | Formula (93) | Formula (7) |
| 154 | Formula (7) | Formula (93) | Formula (8) |
| 155 | Formula (7) | Formula (93) | Formula (13) |
| 156 | Formula (7) | Formula (93) | Formula (17) |
| 157 | Formula (7) | Formula (93) | Formula (28) |
| 158 | Formula (7) | Formula (93) | Formula (41) |
| 159 | Formula (7) | Formula (95) | Formula (2) |
| 160 | Formula (7) | Formula (95) | Formula (3) |
| 161 | Formula (7) | Formula (95) | Formula (4) |
| 162 | Formula (7) | Formula (95) | Formula (7) |
| 163 | Formula (7) | Formula (95) | Formula (8) |
| 164 | Formula (7) | Formula (95) | Formula (13) |
| 165 | Formula (7) | Formula (95) | Formula (17) |
| 166 | Formula (7) | Formula (95) | Formula (28) |
| 167 | Formula (7) | Formula (95) | Formula (41) |
| 168 | Formula (7) | Formula (102) | Formula (2) |
| 169 | Formula (7) | Formula (102) | Formula (3) |
| 170 | Formula (7) | Formula (102) | Formula (4) |
| 171 | Formula (7) | Formula (102) | Formula (7) |
| 172 | Formula (7) | Formula (102) | Formula (8) |
| 173 | Formula (7) | Formula (102) | Formula (13) |
| 174 | Formula (7) | Formula (102) | Formula (17) |
| 175 | Formula (7) | Formula (102) | Formula (28) |
| 176 | Formula (7) | Formula (102) | Formula (41) |
| 177 | Formula (8) | Formula (86) | Formula (3) |
| 178 | Formula (8) | Formula (86) | Formula (4) |
| 179 | Formula (8) | Formula (86) | Formula (7) |
| 180 | Formula (8) | Formula (86) | Formula (8) |
| 181 | Formula (8) | Formula (86) | Formula (13) |
| 182 | Formula (8) | Formula (86) | Formula (17) |
| 183 | Formula (8) | Formula (86) | Formula (28) |
| 184 | Formula (8) | Formula (86) | Formula (41) |
| 185 | Formula (8) | Formula (87) | Formula (3) |
| 186 | Formula (8) | Formula (87) | Formula (4) |
| 187 | Formula (8) | Formula (87) | Formula (7) |
| 188 | Formula (8) | Formula (87) | Formula (8) |
| 189 | Formula (8) | Formula (87) | Formula (13) |
| 190 | Formula (8) | Formula (87) | Formula (17) |
| 191 | Formula (8) | Formula (87) | Formula (28) |
| 192 | Formula (8) | Formula (87) | Formula (41) |
| 193 | Formula (8) | Formula (91) | Formula (2) |
| 194 | Formula (8) | Formula (91) | Formula (3) |
| 195 | Formula (8) | Formula (91) | Formula (4) |

TABLE 3-continued

| No. | Ar1 | Ar2 | Ar3 |
|---|---|---|---|
| 196 | Formula (8) | Formula (91) | Formula (7) |
| 197 | Formula (8) | Formula (91) | Formula (8) |
| 198 | Formula (8) | Formula (91) | Formula (13) |
| 199 | Formula (8) | Formula (91) | Formula (17) |
| 200 | Formula (8) | Formula (91) | Formula (28) |
| 201 | Formula (8) | Formula (91) | Formula (41) |
| 202 | Formula (8) | Formula (93) | Formula (2) |
| 203 | Formula (8) | Formula (93) | Formula (3) |
| 204 | Formula (8) | Formula (93) | Formula (4) |
| 205 | Formula (8) | Formula (93) | Formula (7) |
| 206 | Formula (8) | Formula (93) | Formula (8) |
| 207 | Formula (8) | Formula (93) | Formula (13) |
| 208 | Formula (8) | Formula (93) | Formula (17) |
| 209 | Formula (8) | Formula (93) | Formula (28) |
| 210 | Formula (8) | Formula (93) | Formula (41) |
| 211 | Formula (8) | Formula (95) | Formula (2) |
| 212 | Formula (8) | Formula (95) | Formula (3) |
| 213 | Formula (8) | Formula (95) | Formula (4) |
| 214 | Formula (8) | Formula (95) | Formula (7) |
| 215 | Formula (8) | Formula (95) | Formula (8) |
| 216 | Formula (8) | Formula (95) | Formula (13) |
| 217 | Formula (8) | Formula (95) | Formula (17) |
| 218 | Formula (8) | Formula (95) | Formula (28) |
| 219 | Formula (8) | Formula (95) | Formula (41) |
| 220 | Formula (8) | Formula (102) | Formula (2) |
| 221 | Formula (8) | Formula (102) | Formula (3) |
| 222 | Formula (8) | Formula (102) | Formula (4) |
| 223 | Formula (8) | Formula (102) | Formula (7) |
| 224 | Formula (8) | Formula (102) | Formula (8) |
| 225 | Formula (8) | Formula (102) | Formula (13) |
| 226 | Formula (8) | Formula (102) | Formula (17) |
| 227 | Formula (8) | Formula (102) | Formula (28) |
| 228 | Formula (8) | Formula (102) | Formula (41) |
| 229 | Formula (13) | Formula (86) | Formula (3) |
| 230 | Formula (13) | Formula (86) | Formula (4) |
| 231 | Formula (13) | Formula (86) | Formula (7) |
| 232 | Formula (13) | Formula (86) | Formula (8) |
| 233 | Formula (13) | Formula (86) | Formula (13) |
| 234 | Formula (13) | Formula (86) | Formula (17) |
| 235 | Formula (13) | Formula (86) | Formula (28) |
| 236 | Formula (13) | Formula (86) | Formula (41) |
| 237 | Formula (13) | Formula (87) | Formula (3) |
| 238 | Formula (13) | Formula (87) | Formula (4) |
| 239 | Formula (13) | Formula (87) | Formula (7) |
| 240 | Formula (13) | Formula (87) | Formula (8) |
| 241 | Formula (13) | Formula (87) | Formula (13) |
| 242 | Formula (13) | Formula (87) | Formula (17) |
| 243 | Formula (13) | Formula (87) | Formula (28) |
| 244 | Formula (13) | Formula (87) | Formula (41) |
| 245 | Formula (13) | Formula (91) | Formula (2) |
| 246 | Formula (13) | Formula (91) | Formula (3) |
| 247 | Formula (13) | Formula (91) | Formula (4) |
| 248 | Formula (13) | Formula (91) | Formula (7) |
| 249 | Formula (13) | Formula (91) | Formula (8) |
| 250 | Formula (13) | Formula (91) | Formula (13) |
| 251 | Formula (13) | Formula (91) | Formula (17) |
| 252 | Formula (13) | Formula (91) | Formula (28) |
| 253 | Formula (13) | Formula (91) | Formula (41) |
| 254 | Formula (13) | Formula (93) | Formula (2) |
| 255 | Formula (13) | Formula (93) | Formula (3) |
| 256 | Formula (13) | Formula (93) | Formula (4) |
| 257 | Formula (13) | Formula (93) | Formula (7) |
| 258 | Formula (13) | Formula (93) | Formula (8) |
| 259 | Formula (13) | Formula (93) | Formula (13) |
| 260 | Formula (13) | Formula (93) | Formula (17) |
| 261 | Formula (13) | Formula (93) | Formula (28) |
| 262 | Formula (13) | Formula (93) | Formula (41) |
| 263 | Formula (13) | Formula (95) | Formula (2) |
| 264 | Formula (13) | Formula (95) | Formula (3) |
| 265 | Formula (13) | Formula (95) | Formula (4) |
| 266 | Formula (13) | Formula (95) | Formula (7) |
| 267 | Formula (13) | Formula (95) | Formula (8) |
| 268 | Formula (13) | Formula (95) | Formula (13) |
| 269 | Formula (13) | Formula (95) | Formula (17) |
| 270 | Formula (13) | Formula (95) | Formula (28) |
| 271 | Formula (13) | Formula (95) | Formula (41) |
| 272 | Formula (13) | Formula (102) | Formula (2) |
| 273 | Formula (13) | Formula (102) | Formula (3) |

TABLE 3-continued

| No. | Ar1 | Ar2 | Ar3 |
|---|---|---|---|
| 274 | Formula (13) | Formula (102) | Formula (4) |
| 275 | Formula (13) | Formula (102) | Formula (7) |
| 276 | Formula (13) | Formula (102) | Formula (8) |
| 277 | Formula (13) | Formula (102) | Formula (13) |
| 278 | Formula (13) | Formula (102) | Formula (17) |
| 279 | Formula (13) | Formula (102) | Formula (28) |
| 280 | Formula (13) | Formula (102) | Formula (41) |
| 281 | Formula (17) | Formula (86) | Formula (2) |
| 282 | Formula (17) | Formula (86) | Formula (3) |
| 283 | Formula (17) | Formula (86) | Formula (4) |
| 284 | Formula (17) | Formula (86) | Formula (7) |
| 285 | Formula (17) | Formula (86) | Formula (8) |
| 286 | Formula (17) | Formula (86) | Formula (13) |
| 287 | Formula (17) | Formula (86) | Formula (17) |
| 288 | Formula (17) | Formula (86) | Formula (28) |
| 289 | Formula (17) | Formula (86) | Formula (41) |
| 290 | Formula (17) | Formula (87) | Formula (2) |
| 291 | Formula (17) | Formula (87) | Formula (3) |
| 292 | Formula (17) | Formula (87) | Formula (4) |
| 293 | Formula (17) | Formula (87) | Formula (7) |
| 294 | Formula (17) | Formula (87) | Formula (8) |
| 295 | Formula (17) | Formula (87) | Formula (13) |
| 296 | Formula (17) | Formula (87) | Formula (17) |
| 297 | Formula (17) | Formula (87) | Formula (28) |
| 298 | Formula (17) | Formula (87) | Formula (41) |
| 299 | Formula (17) | Formula (91) | Formula (2) |
| 300 | Formula (17) | Formula (91) | Formula (3) |
| 301 | Formula (17) | Formula (91) | Formula (4) |
| 302 | Formula (17) | Formula (91) | Formula (7) |
| 303 | Formula (17) | Formula (91) | Formula (8) |
| 304 | Formula (17) | Formula (91) | Formula (13) |
| 305 | Formula (17) | Formula (91) | Formula (17) |
| 306 | Formula (17) | Formula (91) | Formula (28) |
| 307 | Formula (17) | Formula (91) | Formula (41) |
| 308 | Formula (17) | Formula (93) | Formula (2) |
| 309 | Formula (17) | Formula (93) | Formula (3) |
| 310 | Formula (17) | Formula (93) | Formula (4) |
| 311 | Formula (17) | Formula (93) | Formula (7) |
| 312 | Formula (17) | Formula (93) | Formula (8) |
| 313 | Formula (17) | Formula (93) | Formula (13) |
| 314 | Formula (17) | Formula (93) | Formula (17) |
| 315 | Formula (17) | Formula (93) | Formula (28) |
| 316 | Formula (17) | Formula (93) | Formula (41) |
| 317 | Formula (17) | Formula (95) | Formula (2) |
| 318 | Formula (17) | Formula (95) | Formula (3) |
| 319 | Formula (17) | Formula (95) | Formula (4) |
| 320 | Formula (17) | Formula (95) | Formula (7) |
| 321 | Formula (17) | Formula (95) | Formula (8) |
| 322 | Formula (17) | Formula (95) | Formula (13) |
| 323 | Formula (17) | Formula (95) | Formula (17) |
| 324 | Formula (17) | Formula (95) | Formula (28) |
| 325 | Formula (17) | Formula (95) | Formula (41) |
| 326 | Formula (17) | Formula (102) | Formula (2) |
| 327 | Formula (17) | Formula (102) | Formula (3) |
| 328 | Formula (17) | Formula (102) | Formula (4) |
| 329 | Formula (17) | Formula (102) | Formula (7) |
| 330 | Formula (17) | Formula (102) | Formula (8) |
| 331 | Formula (17) | Formula (102) | Formula (13) |
| 332 | Formula (17) | Formula (102) | Formula (17) |
| 333 | Formula (17) | Formula (102) | Formula (28) |
| 334 | Formula (17) | Formula (102) | Formula (41) |
| 335 | Formula (28) | Formula (86) | Formula (2) |
| 336 | Formula (28) | Formula (86) | Formula (3) |
| 337 | Formula (28) | Formula (86) | Formula (4) |
| 338 | Formula (28) | Formula (86) | Formula (7) |
| 339 | Formula (28) | Formula (86) | Formula (8) |
| 340 | Formula (28) | Formula (86) | Formula (13) |
| 341 | Formula (28) | Formula (86) | Formula (17) |
| 342 | Formula (28) | Formula (86) | Formula (28) |
| 343 | Formula (28) | Formula (86) | Formula (41) |
| 344 | Formula (28) | Formula (87) | Formula (2) |
| 345 | Formula (28) | Formula (87) | Formula (3) |
| 346 | Formula (28) | Formula (87) | Formula (4) |
| 347 | Formula (28) | Formula (87) | Formula (7) |
| 348 | Formula (28) | Formula (87) | Formula (8) |
| 349 | Formula (28) | Formula (87) | Formula (13) |
| 350 | Formula (28) | Formula (87) | Formula (17) |
| 351 | Formula (28) | Formula (87) | Formula (28) |
| 352 | Formula (28) | Formula (87) | Formula (41) |
| 353 | Formula (28) | Formula (91) | Formula (2) |
| 354 | Formula (28) | Formula (91) | Formula (3) |
| 355 | Formula (28) | Formula (91) | Formula (4) |
| 356 | Formula (28) | Formula (91) | Formula (7) |
| 357 | Formula (28) | Formula (91) | Formula (8) |
| 358 | Formula (28) | Formula (91) | Formula (13) |
| 359 | Formula (28) | Formula (91) | Formula (17) |
| 360 | Formula (28) | Formula (91) | Formula (28) |
| 361 | Formula (28) | Formula (91) | Formula (41) |
| 362 | Formula (28) | Formula (93) | Formula (2) |
| 363 | Formula (28) | Formula (93) | Formula (3) |
| 364 | Formula (28) | Formula (93) | Formula (4) |
| 365 | Formula (28) | Formula (93) | Formula (7) |
| 366 | Formula (28) | Formula (93) | Formula (8) |
| 367 | Formula (28) | Formula (93) | Formula (13) |
| 368 | Formula (28) | Formula (93) | Formula (17) |
| 369 | Formula (28) | Formula (93) | Formula (28) |
| 370 | Formula (28) | Formula (93) | Formula (41) |
| 371 | Formula (28) | Formula (95) | Formula (2) |
| 372 | Formula (28) | Formula (95) | Formula (3) |
| 373 | Formula (28) | Formula (95) | Formula (4) |
| 374 | Formula (28) | Formula (95) | Formula (7) |
| 375 | Formula (28) | Formula (95) | Formula (8) |
| 376 | Formula (28) | Formula (95) | Formula (13) |
| 377 | Formula (28) | Formula (95) | Formula (17) |
| 378 | Formula (28) | Formula (95) | Formula (28) |
| 379 | Formula (28) | Formula (95) | Formula (41) |
| 380 | Formula (28) | Formula (102) | Formula (2) |
| 381 | Formula (28) | Formula (102) | Formula (3) |
| 382 | Formula (28) | Formula (102) | Formula (4) |
| 383 | Formula (28) | Formula (102) | Formula (7) |
| 384 | Formula (28) | Formula (102) | Formula (8) |
| 385 | Formula (28) | Formula (102) | Formula (13) |
| 386 | Formula (28) | Formula (102) | Formula (17) |
| 387 | Formula (28) | Formula (102) | Formula (28) |
| 388 | Formula (28) | Formula (102) | Formula (41) |
| 389 | Formula (41) | Formula (86) | Formula (2) |
| 390 | Formula (41) | Formula (86) | Formula (3) |
| 391 | Formula (41) | Formula (86) | Formula (4) |
| 392 | Formula (41) | Formula (86) | Formula (7) |
| 393 | Formula (41) | Formula (86) | Formula (8) |
| 394 | Formula (41) | Formula (86) | Formula (13) |
| 395 | Formula (41) | Formula (86) | Formula (17) |
| 396 | Formula (41) | Formula (86) | Formula (28) |
| 397 | Formula (41) | Formula (86) | Formula (41) |
| 398 | Formula (41) | Formula (87) | Formula (2) |
| 399 | Formula (41) | Formula (87) | Formula (3) |
| 400 | Formula (41) | Formula (87) | Formula (4) |
| 401 | Formula (41) | Formula (87) | Formula (7) |
| 402 | Formula (41) | Formula (87) | Formula (8) |
| 403 | Formula (41) | Formula (87) | Formula (13) |
| 404 | Formula (41) | Formula (87) | Formula (17) |
| 405 | Formula (41) | Formula (87) | Formula (28) |
| 406 | Formula (41) | Formula (87) | Formula (41) |
| 407 | Formula (41) | Formula (91) | Formula (2) |
| 408 | Formula (41) | Formula (91) | Formula (3) |
| 409 | Formula (41) | Formula (91) | Formula (4) |
| 410 | Formula (41) | Formula (91) | Formula (7) |
| 411 | Formula (41) | Formula (91) | Formula (8) |
| 412 | Formula (41) | Formula (91) | Formula (13) |
| 413 | Formula (41) | Formula (91) | Formula (17) |
| 414 | Formula (41) | Formula (91) | Formula (28) |
| 415 | Formula (41) | Formula (91) | Formula (41) |
| 416 | Formula (41) | Formula (93) | Formula (2) |
| 417 | Formula (41) | Formula (93) | Formula (3) |
| 418 | Formula (41) | Formula (93) | Formula (4) |
| 419 | Formula (41) | Formula (93) | Formula (7) |
| 420 | Formula (41) | Formula (93) | Formula (8) |
| 421 | Formula (41) | Formula (93) | Formula (13) |
| 422 | Formula (41) | Formula (93) | Formula (17) |
| 423 | Formula (41) | Formula (93) | Formula (28) |
| 424 | Formula (41) | Formula (93) | Formula (41) |
| 425 | Formula (41) | Formula (95) | Formula (2) |
| 426 | Formula (41) | Formula (95) | Formula (3) |
| 427 | Formula (41) | Formula (95) | Formula (4) |
| 428 | Formula (41) | Formula (95) | Formula (7) |
| 429 | Formula (41) | Formula (95) | Formula (8) |

TABLE 3-continued

| No. | Ar1 | Ar2 | Ar3 |
|---|---|---|---|
| 430 | Formula (41) | Formula (95) | Formula (13) |
| 431 | Formula (41) | Formula (95) | Formula (17) |
| 432 | Formula (41) | Formula (95) | Formula (28) |
| 433 | Formula (41) | Formula (95) | Formula (41) |
| 434 | Formula (41) | Formula (102) | Formula (2) |
| 435 | Formula (41) | Formula (102) | Formula (3) |
| 436 | Formula (41) | Formula (102) | Formula (4) |
| 437 | Formula (41) | Formula (102) | Formula (7) |
| 438 | Formula (41) | Formula (102) | Formula (8) |
| 439 | Formula (41) | Formula (102) | Formula (13) |
| 440 | Formula (41) | Formula (102) | Formula (17) |
| 441 | Formula (41) | Formula (102) | Formula (28) |
| 442 | Formula (41) | Formula (102) | Formula (41) |

Preference is furthermore given to compounds of the formula (1) in which the symbol p=1 or p=2. Particular preference is given to compounds where p=1. This preference also applies to the combinations of $Ar^1$, $Ar^2$ and $Ar^3$ shown above in Tables 1, 2 and 3.

Preference is furthermore given to compounds of the formula (1) in which the symbol X is selected, identically or differently on each occurrence, from the group consisting of $B(R^2)$, $C(R^2)_2$, $Si(R^2)_2$, O, S or $N(R^2)$, particularly preferably $C(R^2)_2$, S or $N(R^2)$. Very particularly preferably, all symbols X stand, identically or differently on each occurrence, for $C(R^2)_2$. $R^2$ here preferably stands for an alkyl or aryl group.

$Ar^1$, $Ar^2$ and $Ar^3$ are particularly preferably selected as shown in Tables 1 and 2, and X simultaneously stands, identically or differently on each occurrence, for $C(R^2)_2$. $R^2$ here preferably stands for an alkyl or aryl group.

Particular preference is given to compounds of the formula (1) selected from the formulae (111) to (141), where the aromatic systems may each also be substituted by one or more radicals $R^1$:

formula (111)

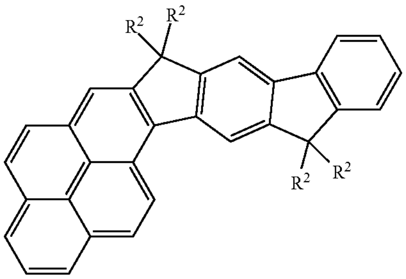

formula (112)

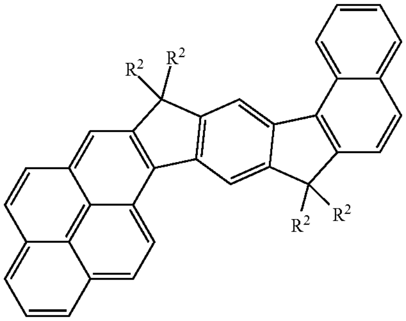

-continued formula (113)

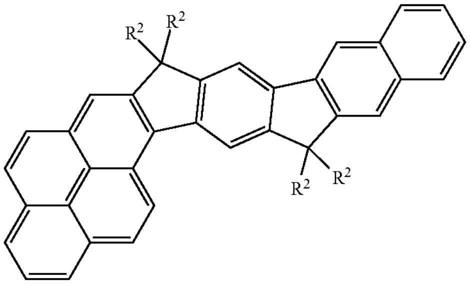

formula (114)

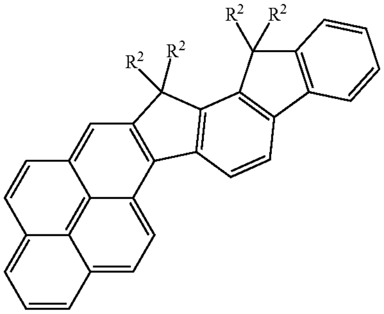

formula (115)

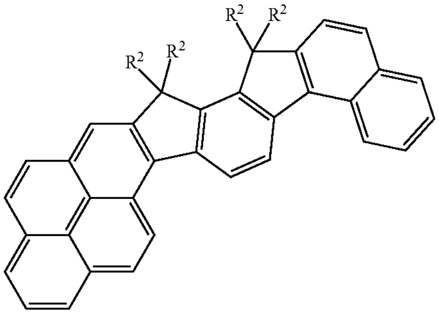

formula (116)

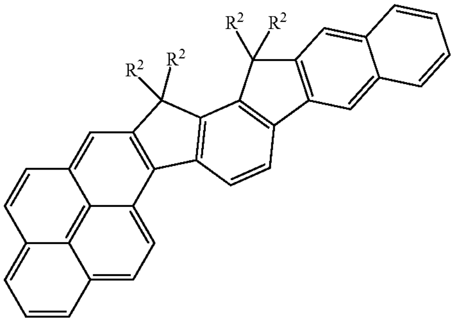

formula (117)

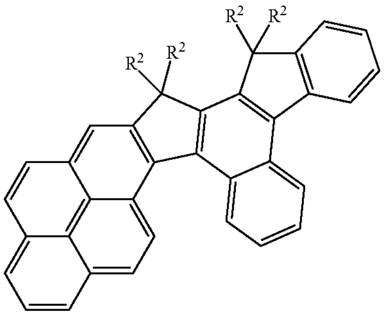

-continued
formula (118)
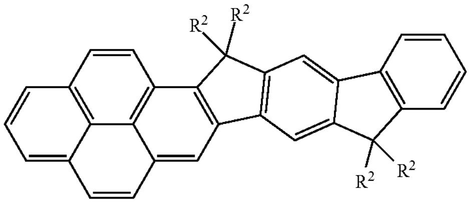
formula (119)
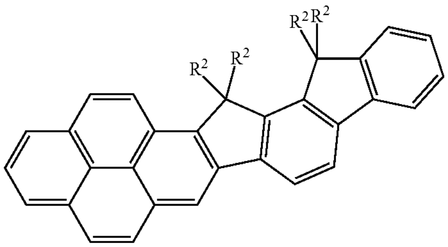
formula (120)
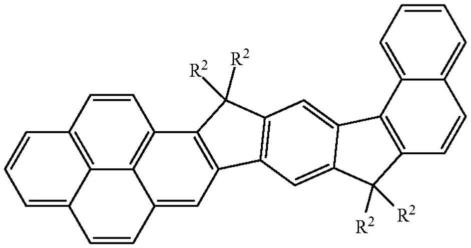
formula (121)
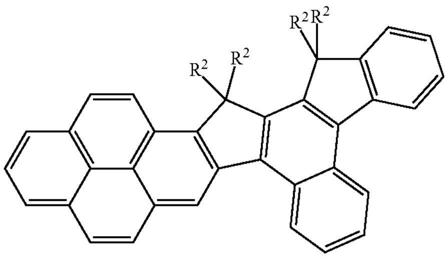
formula (122)
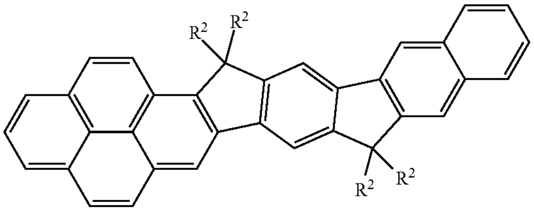
formula (123)
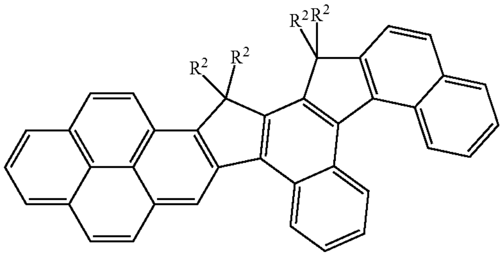
-continued
formula (124)
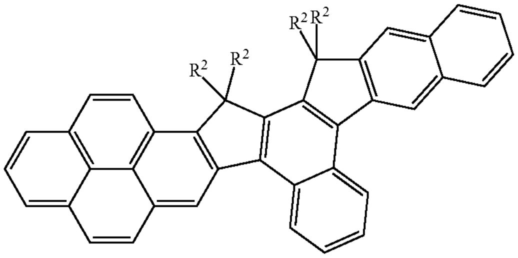
formula (125)
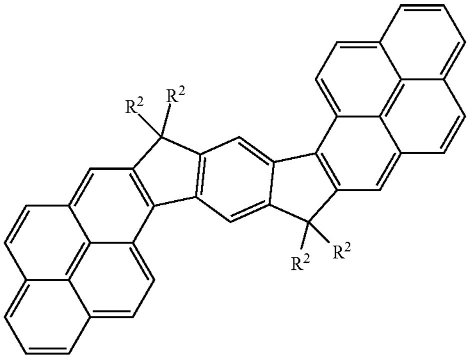
formula (126)
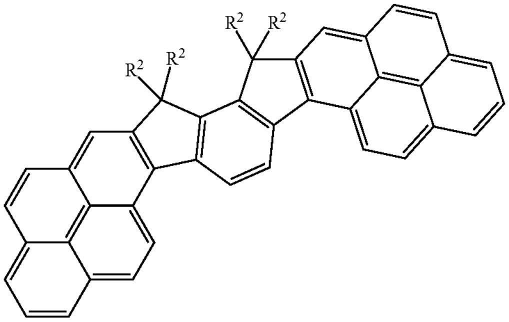
formula (127)
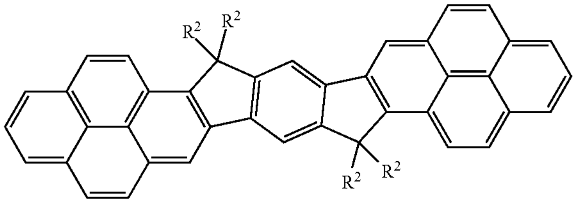
formula (128)
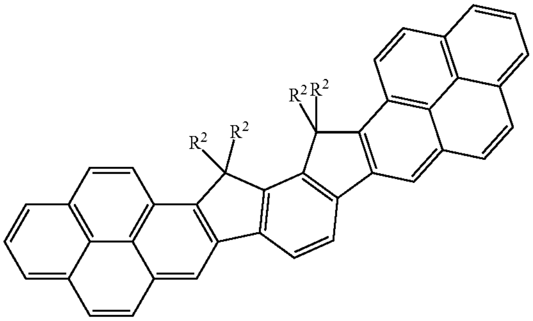

-continued
formula (129)
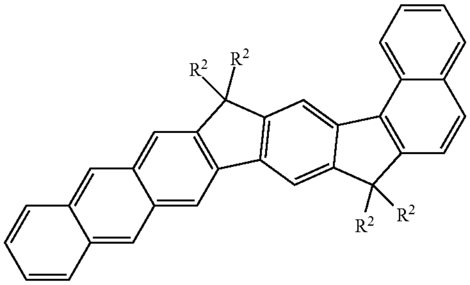
formula (130)
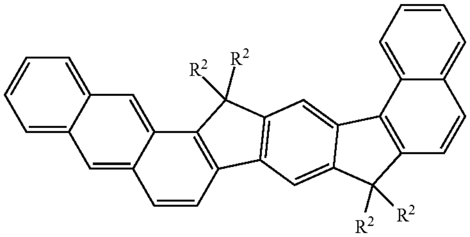
formula (131)
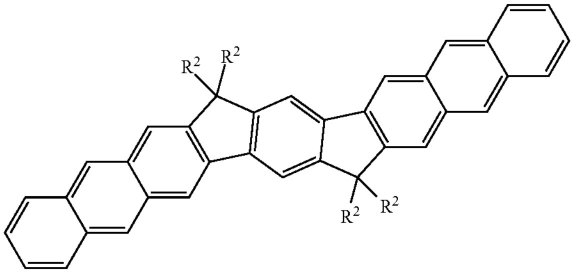
formula (132)
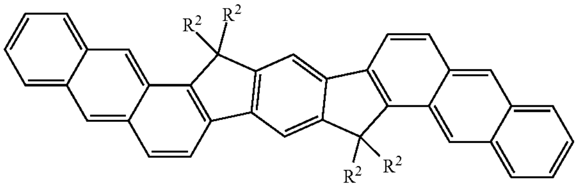
formula (133)
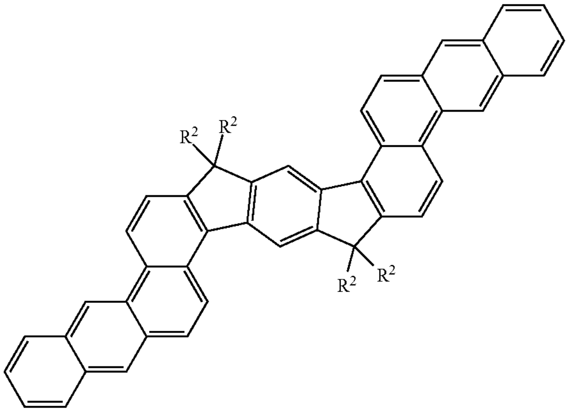
-continued
formula (134)
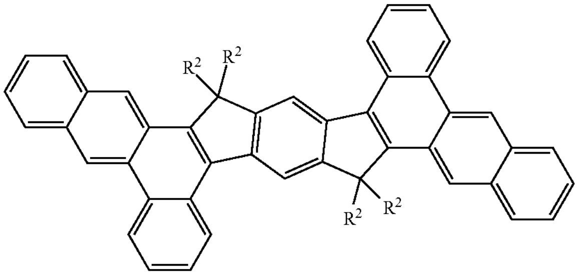
formula (135)
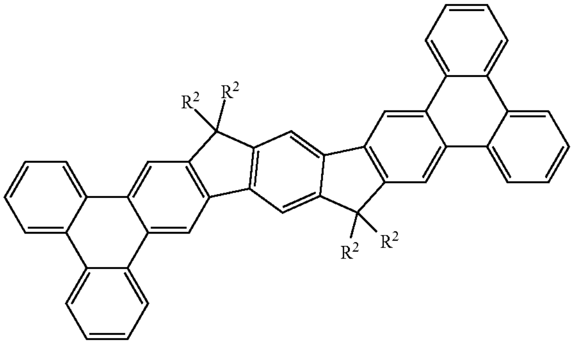
formula (136)
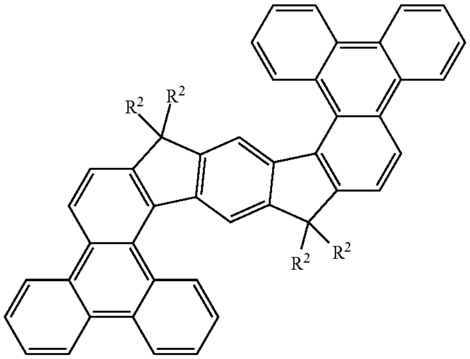
formula (137)
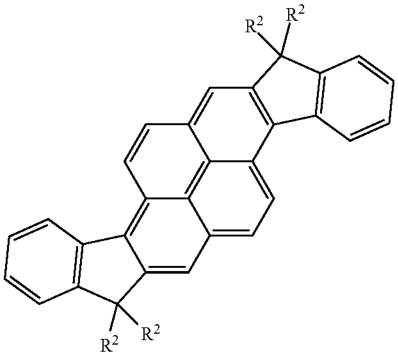

-continued formula (138)

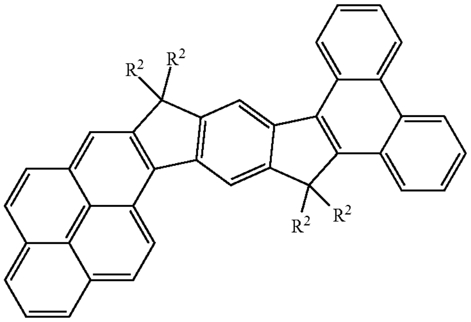

formula (139)

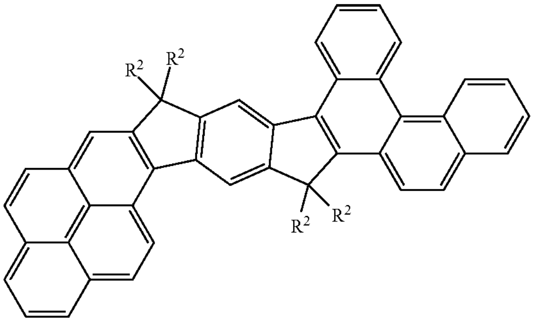

formula (140)

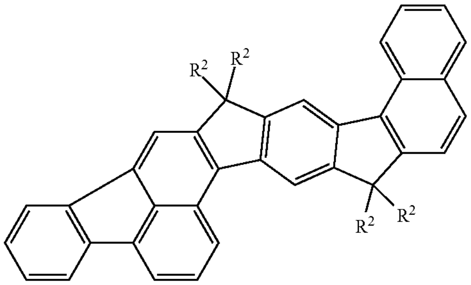

formula (141)

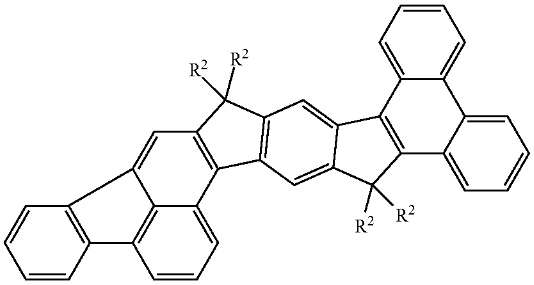

Preference is furthermore given to compounds of the formula (1) in which the symbol $R^1$, which may be bonded to $Ar^1$, $Ar^2$ or $Ar^3$ as a substituent, is selected on each occurrence, identically or differently, from the group consisting of H, D, F, $Si(R^3)_3$, straight-chain alkyl or alkoxy groups having 1 to 10 C atoms or branched or cyclic alkyl or alkoxy groups having 3 to 10 C atoms, each of which may be substituted by one or more radicals $R^3$, where in each case one or more non-adjacent $CH_2$ groups may be replaced by $R^3C{=}CR^3$ or O and where one or more H atoms may be replaced by F, or aromatic or heteroaromatic ring systems having 5 to 40 aromatic ring atoms, or a combination of these systems; two or more substituents $R^1$ here may also form a mono- or polycyclic, aliphatic or aromatic ring system with one another. The substituent $R^1$ is particularly preferably selected from H, D, straight-chain alkyl groups having 1 to 6 C atoms, branched or cyclic alkyl groups having 3 to 6 C atoms or an aromatic or heteroaromatic ring system having 5 to 24 aromatic ring atoms; two or more substituents $R^1$ here may also form a mono- or polycyclic ring system with one another. The substituent $R^1$ is very particularly preferably selected from H, D, alkyl groups selected from methyl, ethyl, n-propyl, isopropyl, n-butyl, isobutyl, tert-butyl, cyclopentyl or cyclohexyl, in particular methyl or tert-butyl, and aromatic or heteroaromatic ring systems selected from the group consisting of unsubstituted or $R^3$-substituted phenyl, naphthyl, benzimidazole, which may also be substituted by phenyl, phenylbenzimidazole, where the benzimidazole may also be substituted by phenyl or other radicals $R^3$, or triazine, which may also be substituted by phenyl or other radicals $R^3$.

Preference is furthermore given to compounds of the formula (1) in which the symbol $R^2$, which is bonded to the group X, is selected on each occurrence, identically or differently, from H, straight-chain alkyl groups having 1 to 10 C atoms or branched or cyclic alkyl groups having 3 to 10 C atoms, where in each case one or more non-adjacent $CH_2$ groups may be replaced by $—R^2C{=}CR^2—$ or —O— and where one or more H atoms may be replaced by F, or a monovalent aryl or heteroaryl group having 5 to 16 aromatic ring atoms, which may be substituted by one or more non-aromatic radicals $R^2$; two radicals $R^2$ which are bonded in the same group X may also form a ring system with one another. The radicals $R^2$ are particularly preferably selected from straight-chain alkyl groups having 1 to 4 C atoms or branched alkyl groups having 3 or 4 C atoms, in particular methyl groups, or phenyl groups; two or more radicals $R^2$ here may form a ring system with one another. If a plurality of radicals $R^2$ form a ring system with one another, a spiro structure is thereby formed. This may be preferred, in particular, if the radicals $R^2$ stand for phenyl groups or if two radicals $R^2$ stand for alkyl groups which form a ring system with one another.

Examples of preferred compounds of the formula (1) are structures (1) to (246) depicted below.

(1)

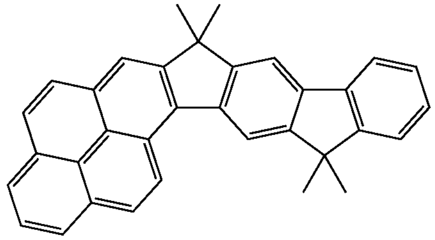

(2)

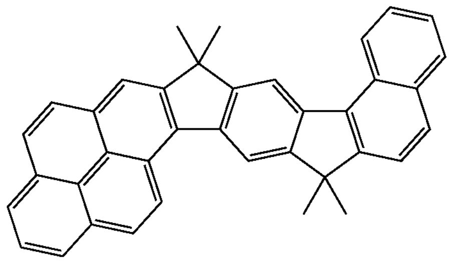

-continued
(3)
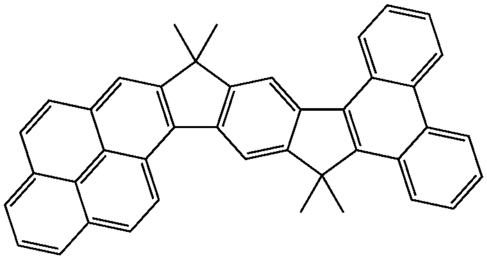
(4)
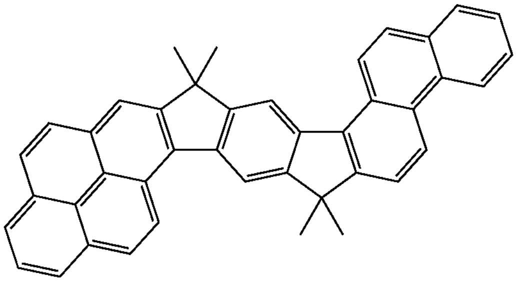
(5)
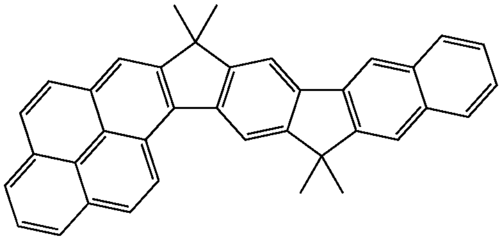
(6)
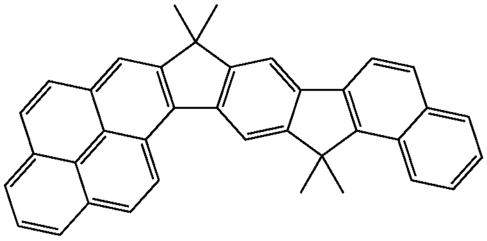
(7)
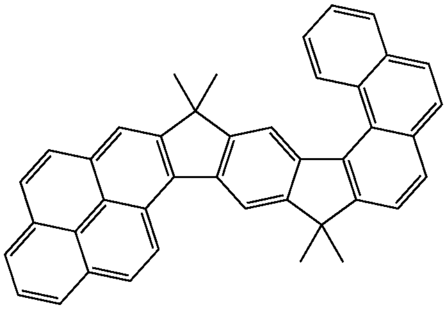
-continued
(8)
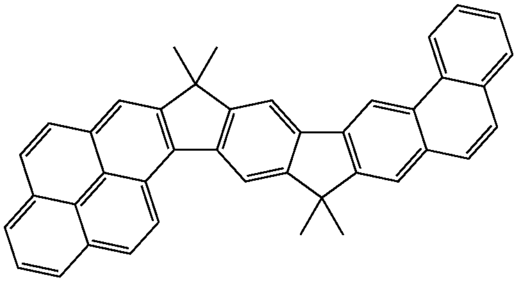
(9)
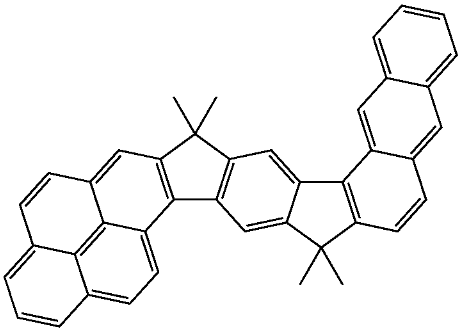
(10)
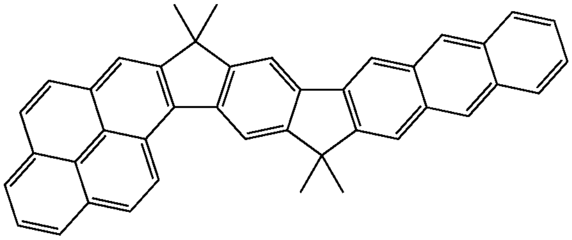
(11)
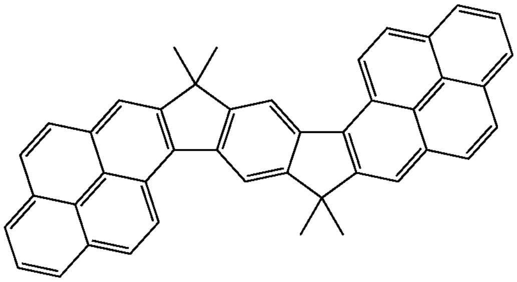
(12)
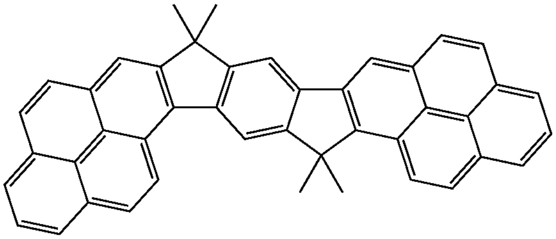

(13)
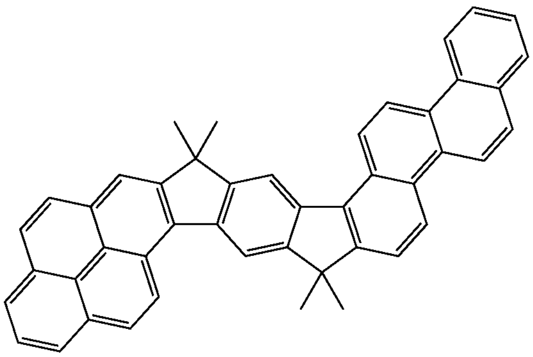
(14)
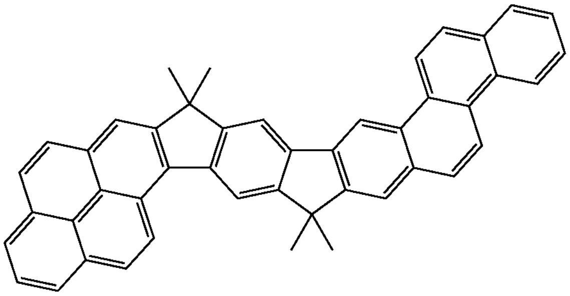
(15)
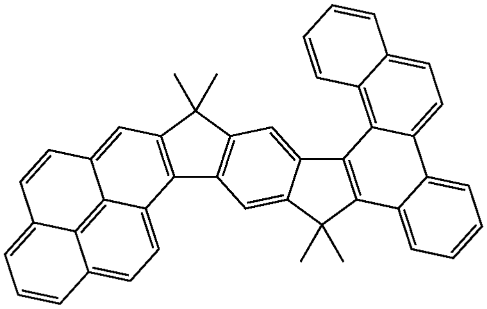
(16)
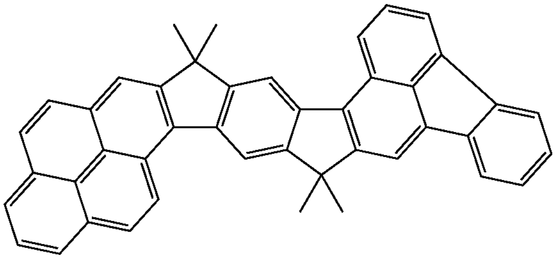
(17)
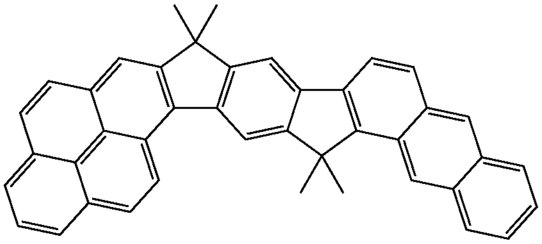
(18)
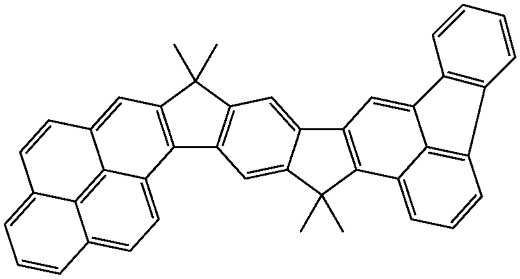
(19)
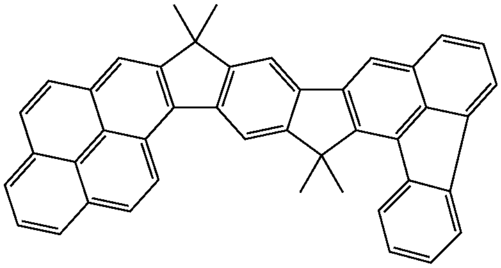
(20)
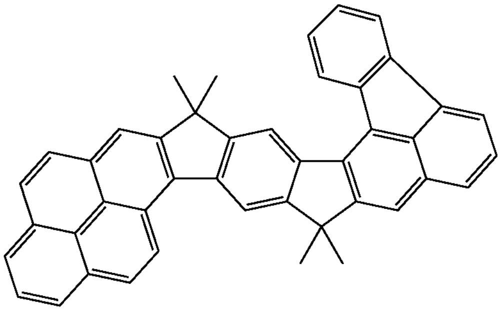
(21)
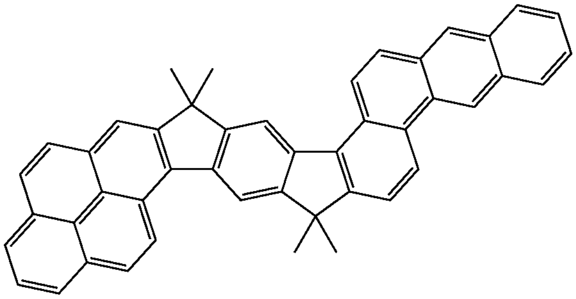
(22)
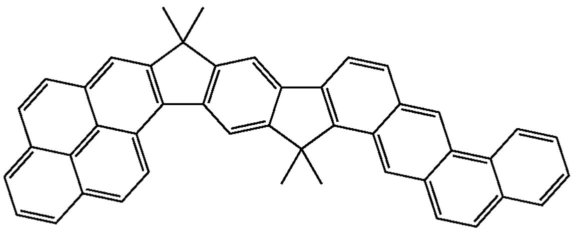

-continued
(23)
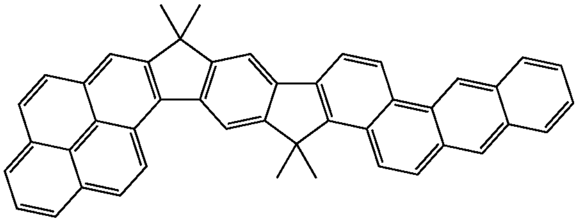
(24)
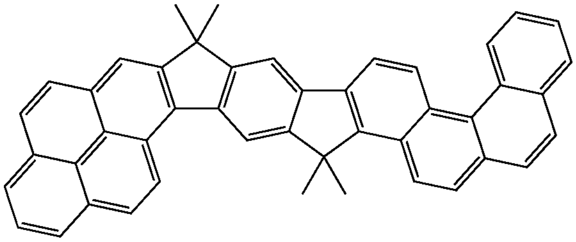
(25)
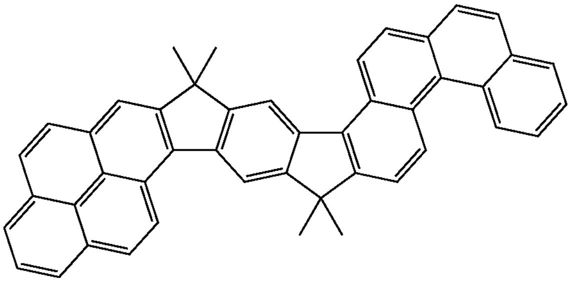
(26)
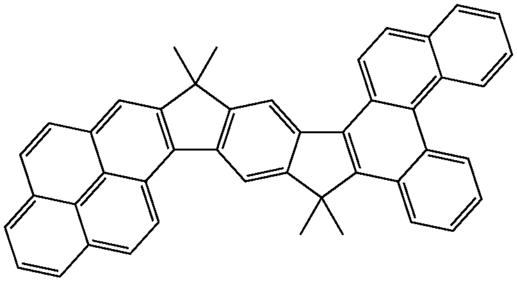
(27)
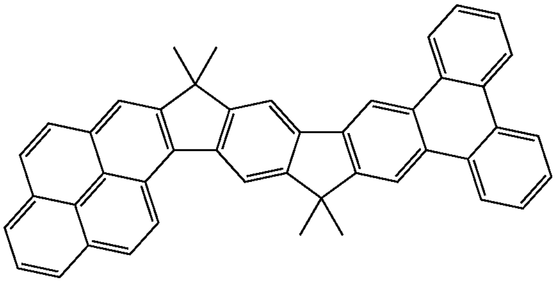
-continued
(28)
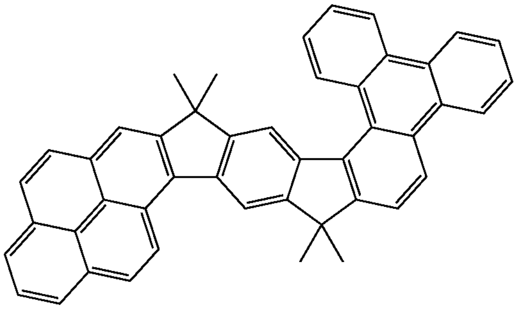
(29)
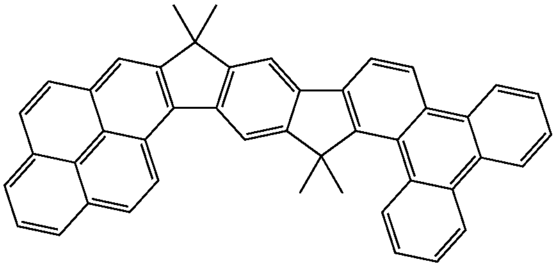
(30)
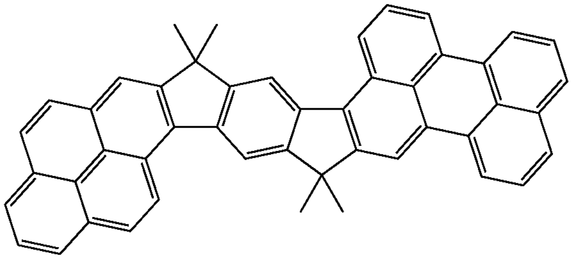
(31)
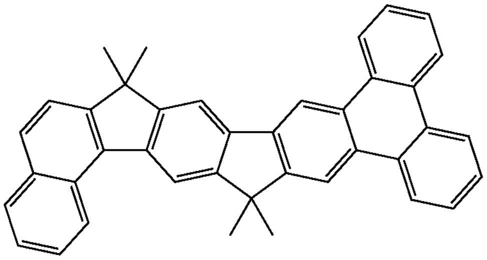
(32)
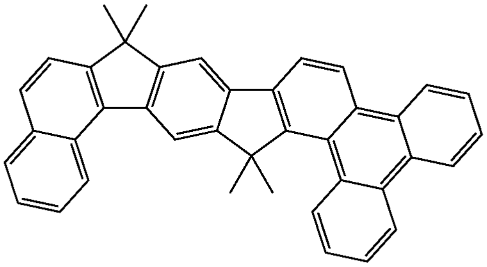

-continued
(33)
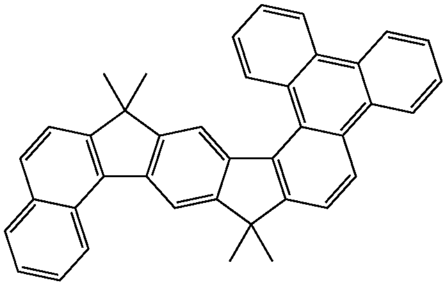
(34)
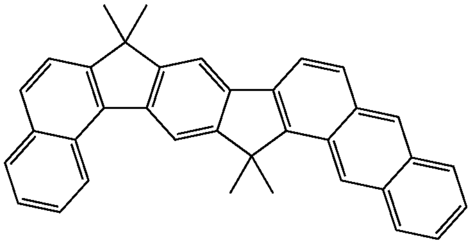
(35)
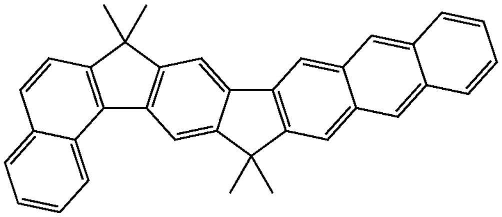
(36)
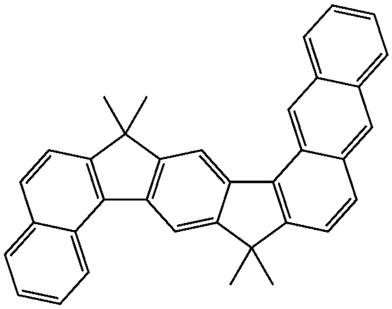
(37)
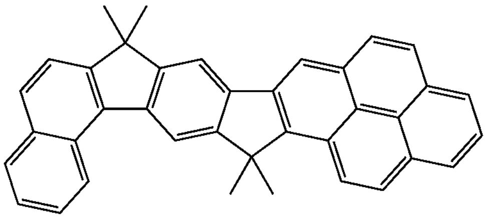
(38)
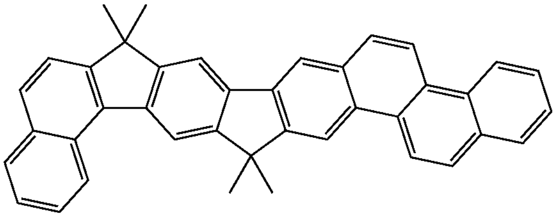
-continued
(39)
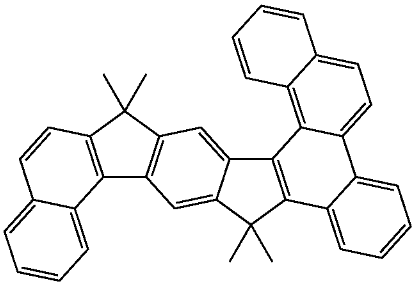
(40)
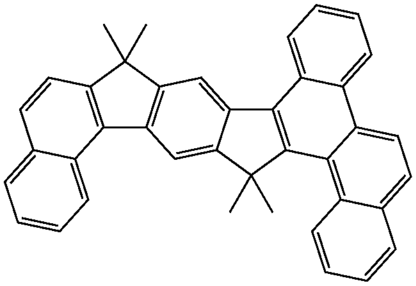
(41)
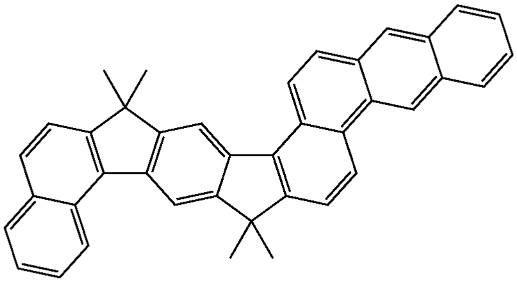
(42)
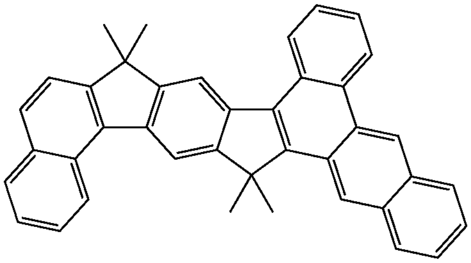
(43)
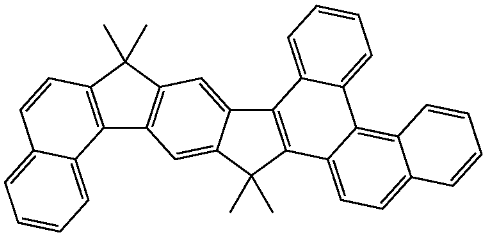

-continued
(44)
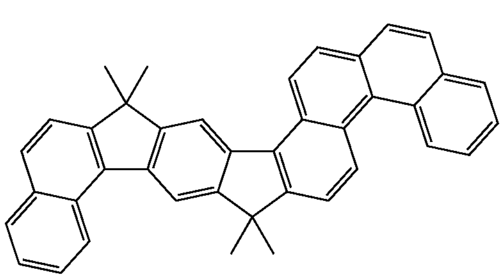
(45)
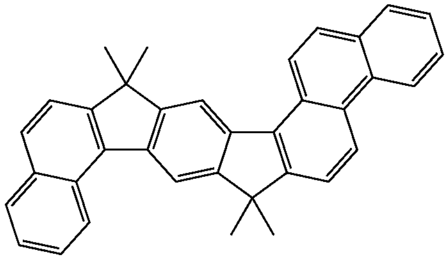
(46)
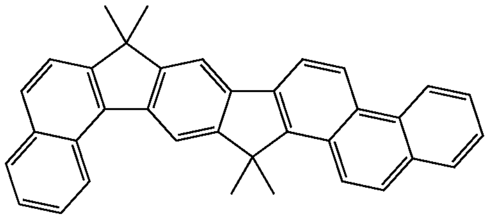
(47)
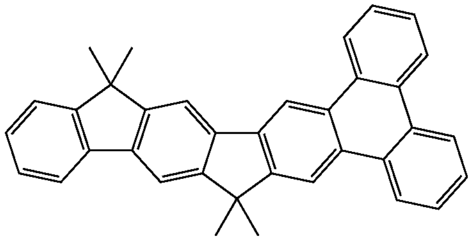
(48)
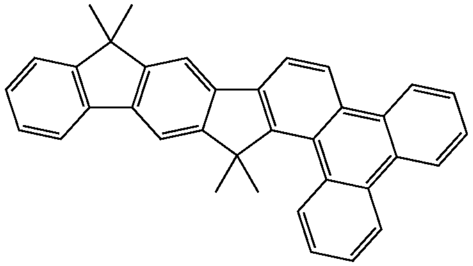
(49)
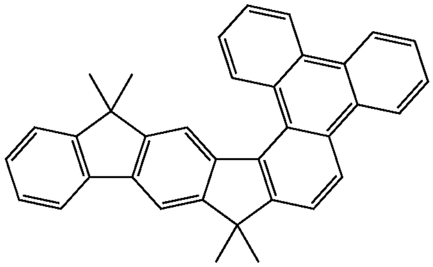
-continued
(50)
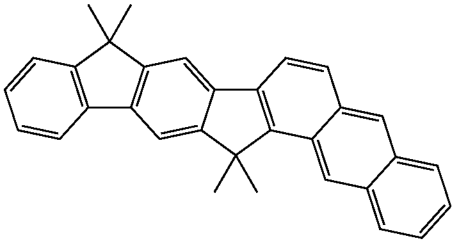
(51)
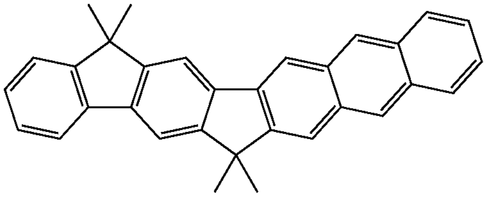
(52)
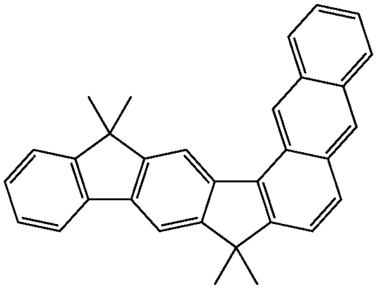
(53)
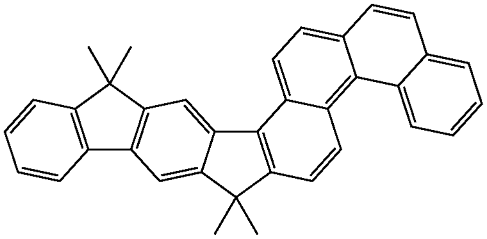
(54)
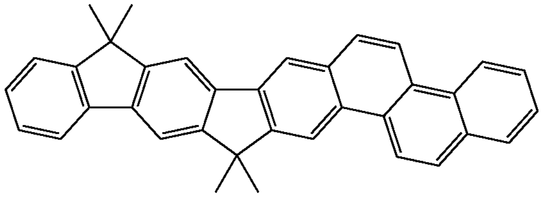
(55)
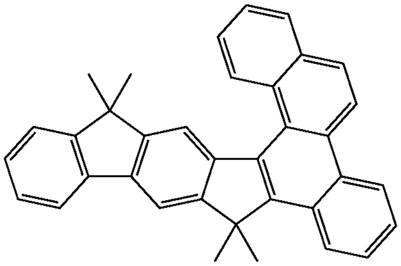

-continued
(56)
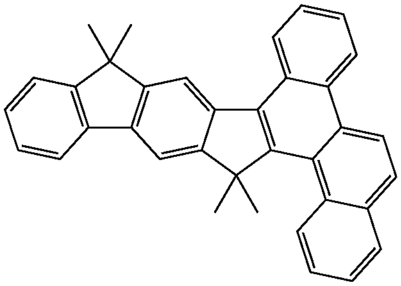
(57)
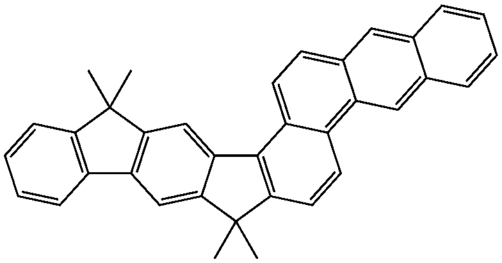
(58)
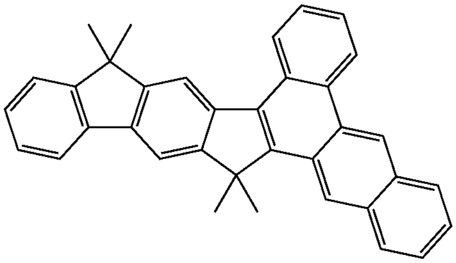
(59)
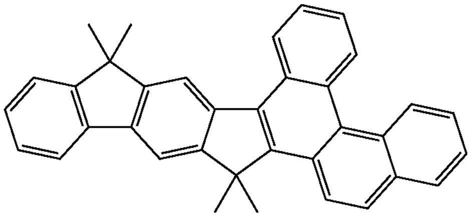
(60)
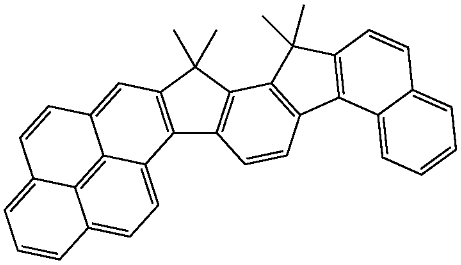
(61)
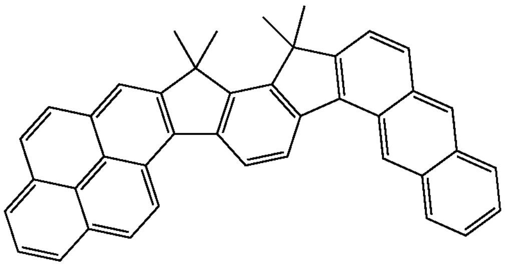
-continued
(62)
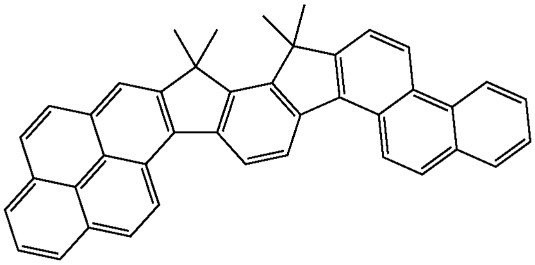
(63)
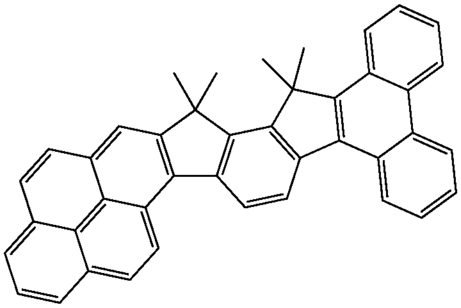
(64)
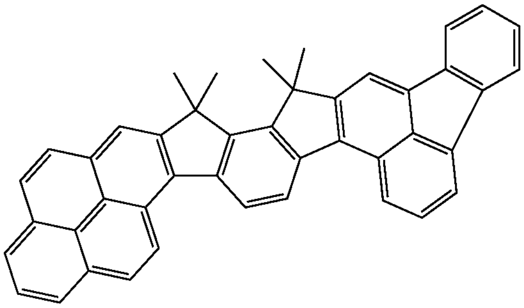
(65)
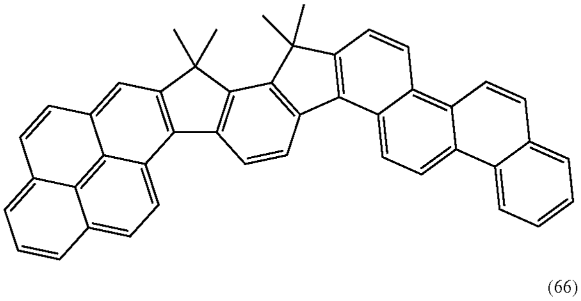
(66)
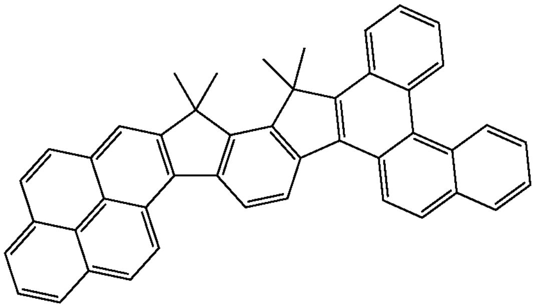

-continued
(67)
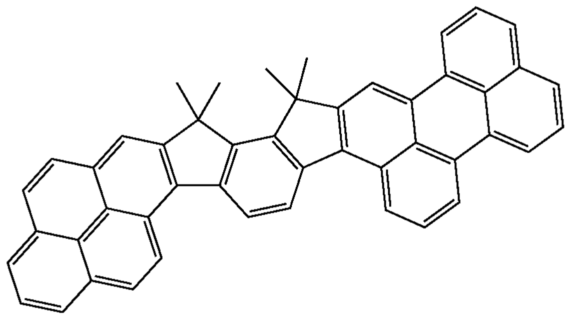
(68)
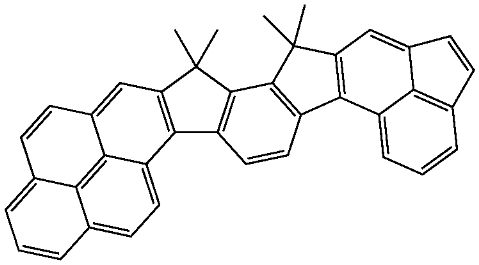
(69)
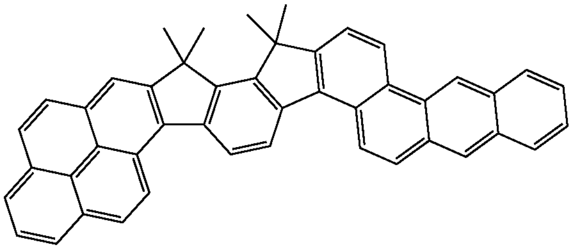
(70)
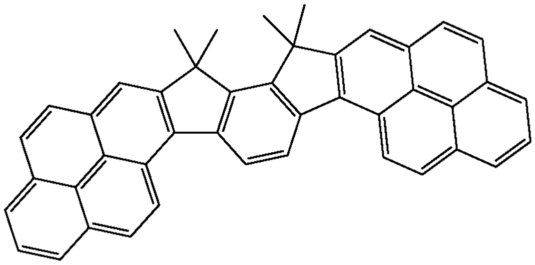
(71)
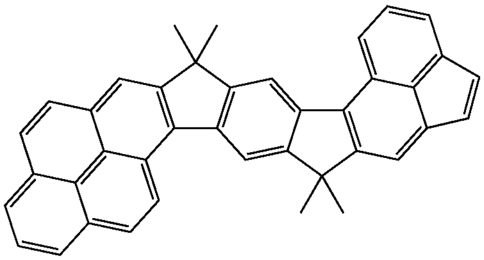
-continued
(72)
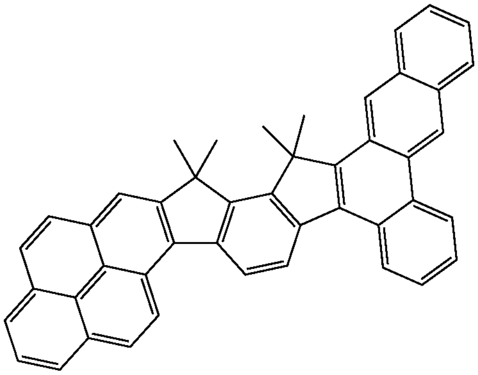
(73)
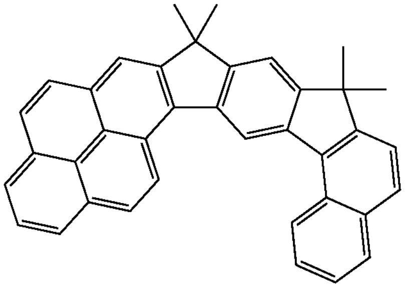
(74)
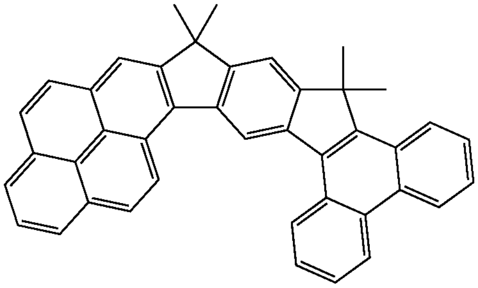
(75)
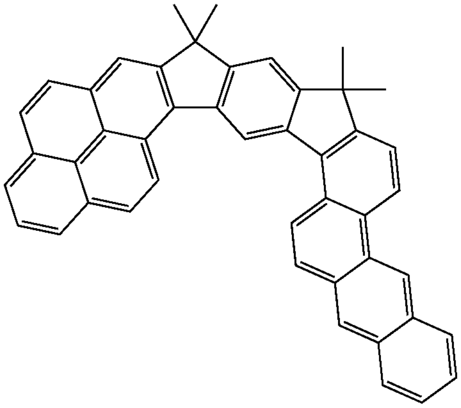

-continued
(76)
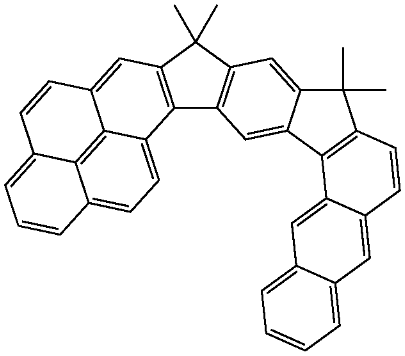
(77)
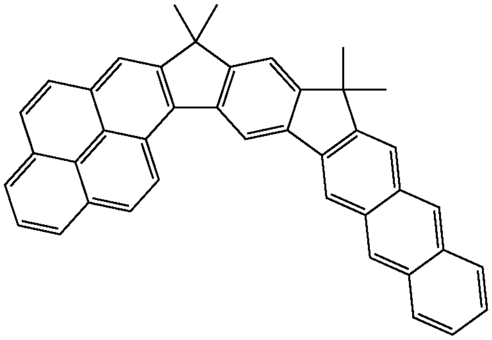
(78)
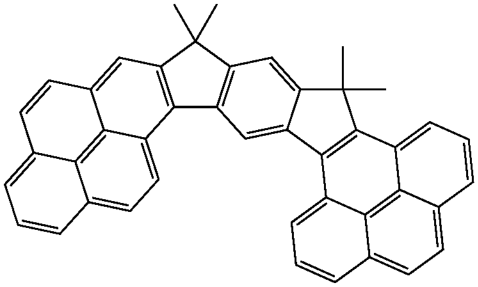
(79)
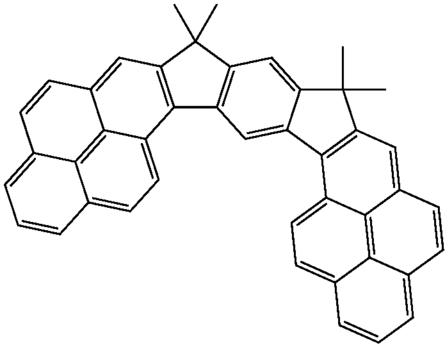
-continued
(80)
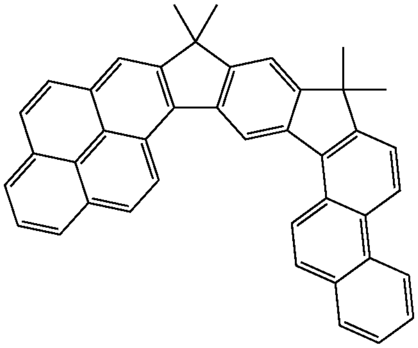
(81)
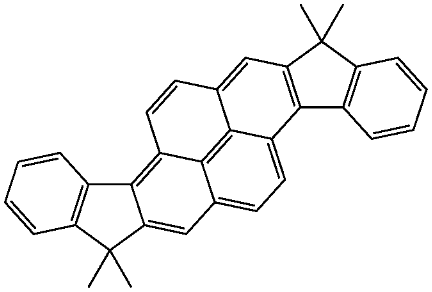
(82)
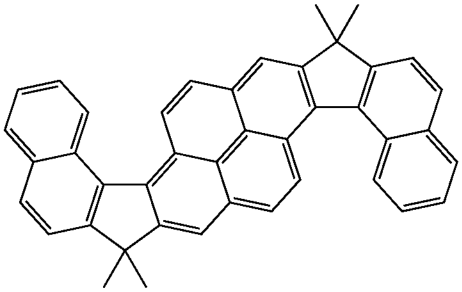
(83)
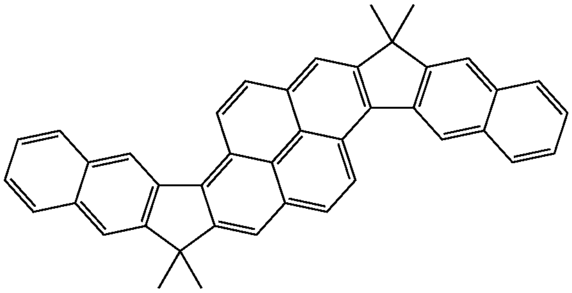
(84)
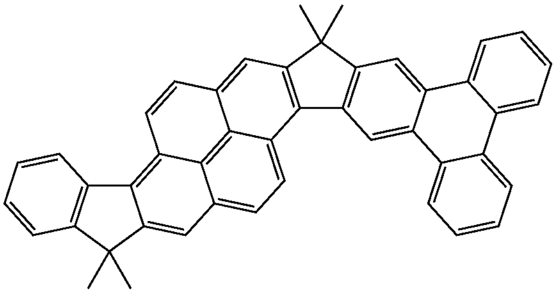

-continued
(85)
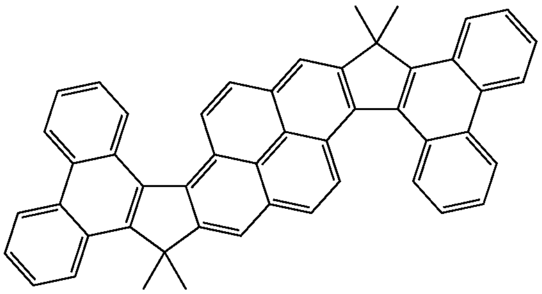
(86)
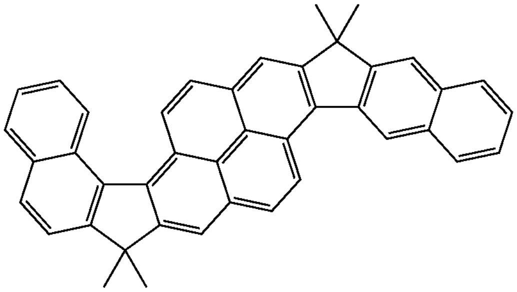
-continued
(87)
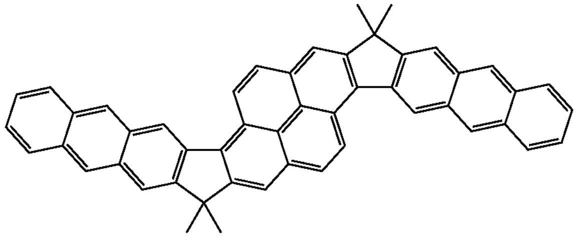
(88)
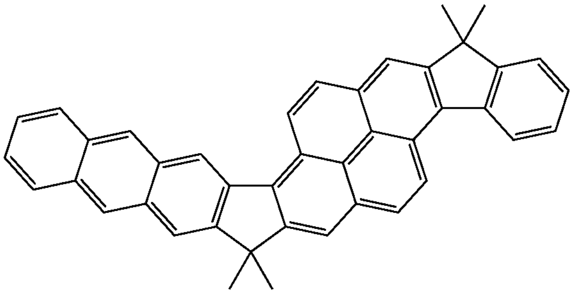
(89)
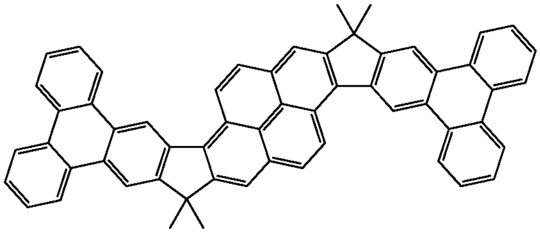
(90)
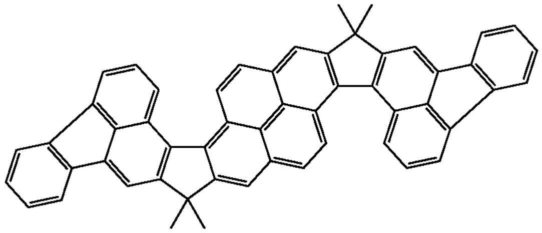
(91)
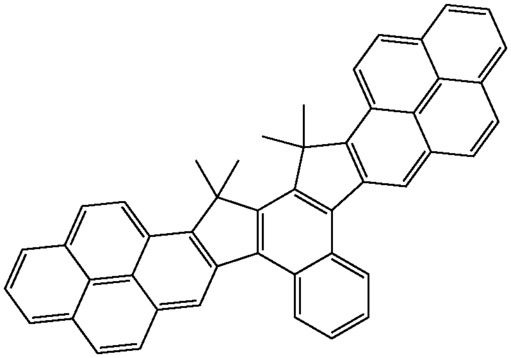
(92)
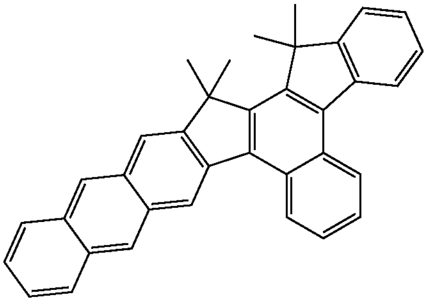

-continued
(93)
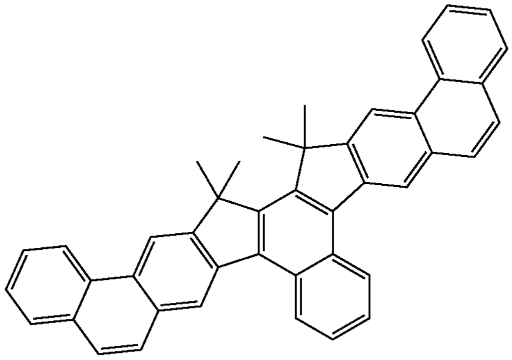
(94)
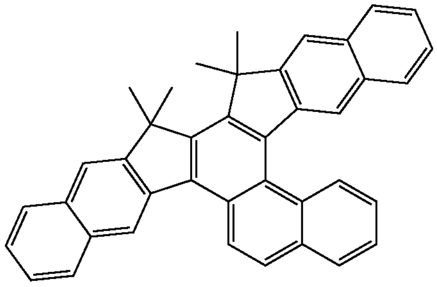
(95)
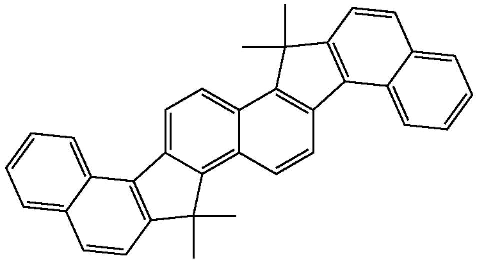
(96)
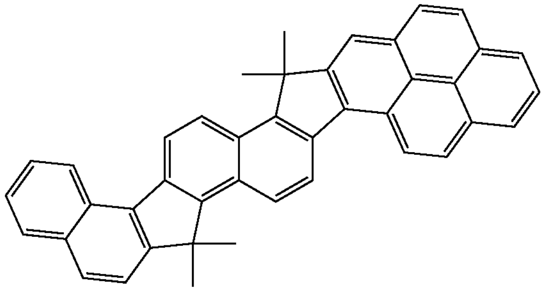
(97)
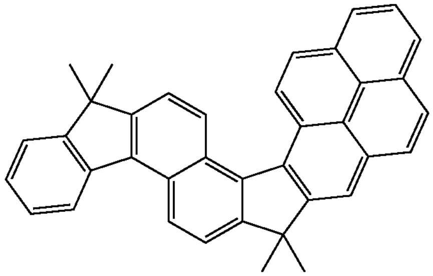
(98)
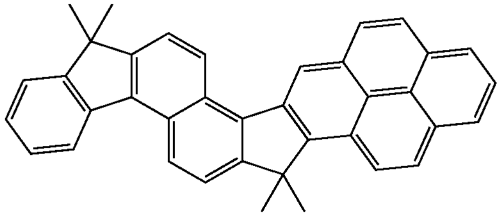
(99)
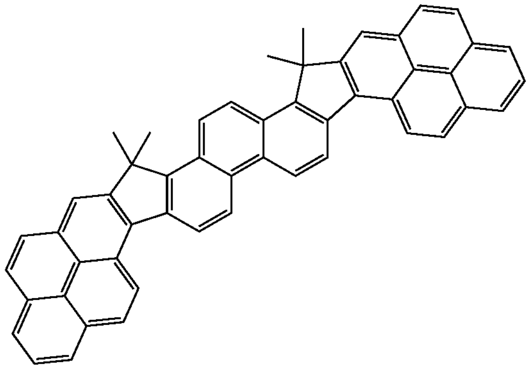
(100)
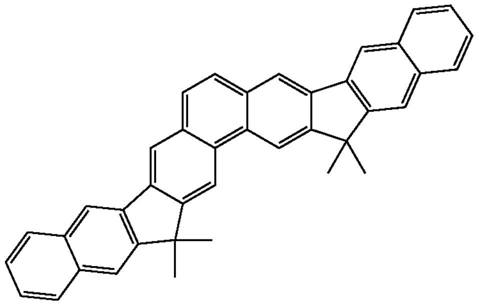

-continued
(101)
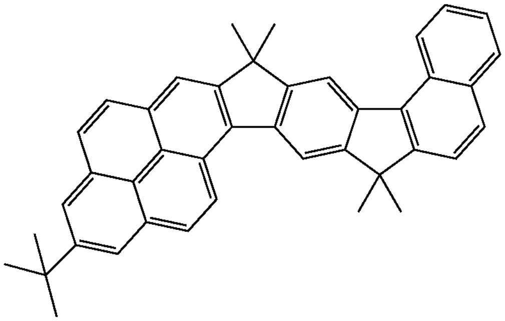
(102)
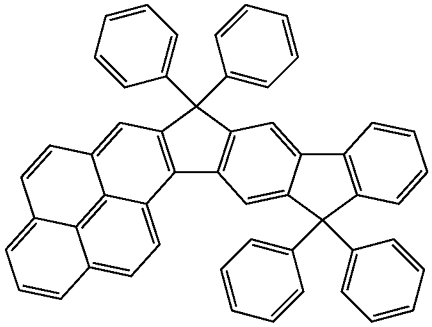
(103)
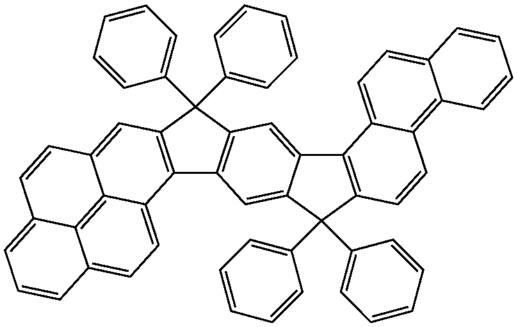
(104)
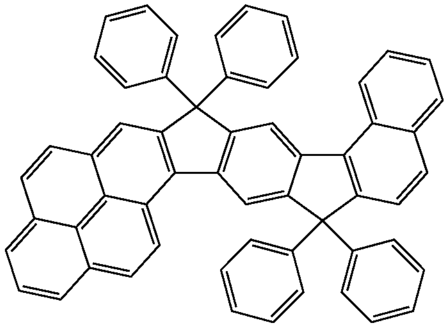
(105)
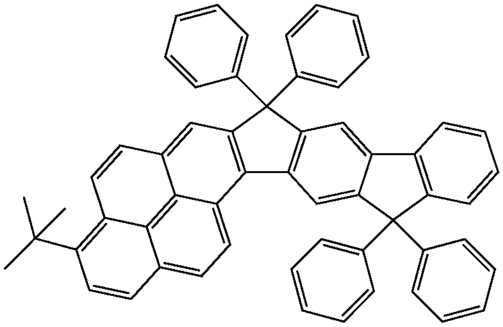
(106)
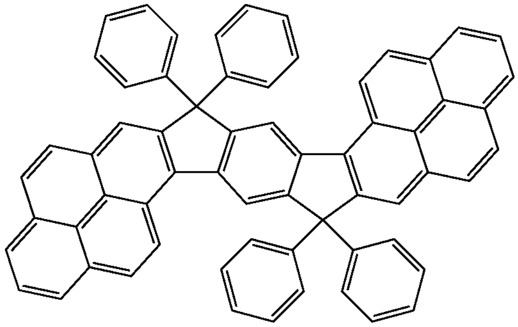
(107)
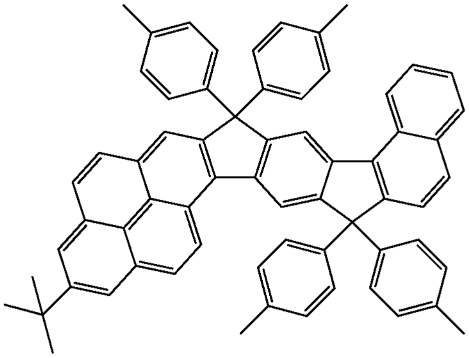
(108)
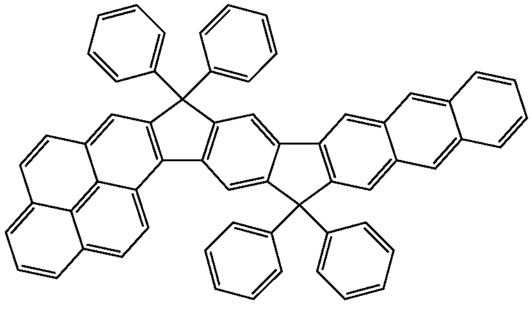

-continued
(109)
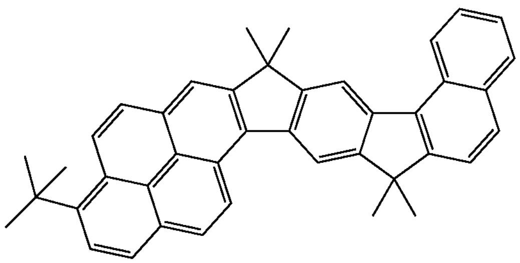
(110)
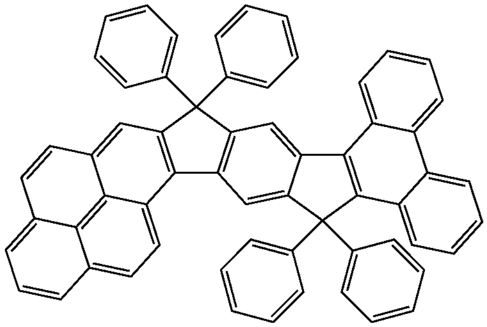
(111)
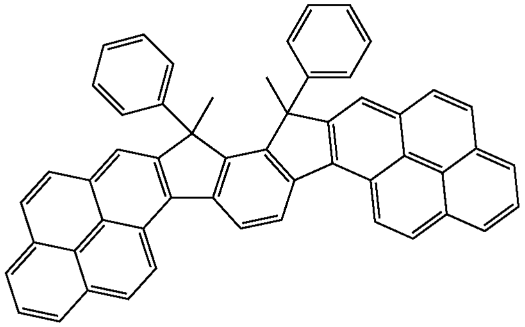
(112)
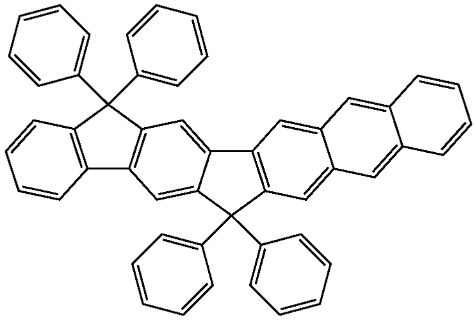
(113)
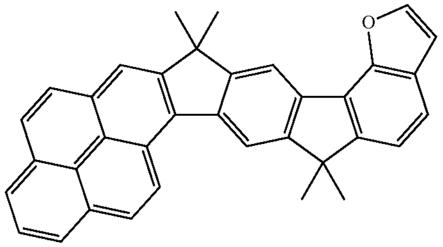
(114)
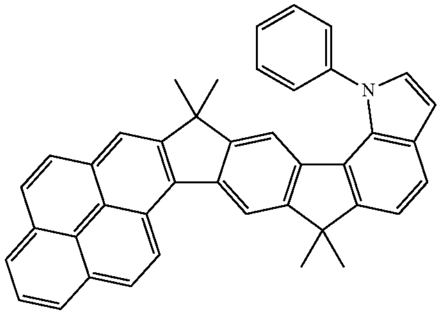
(115)
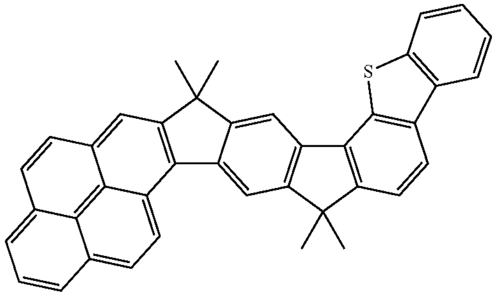
(116)
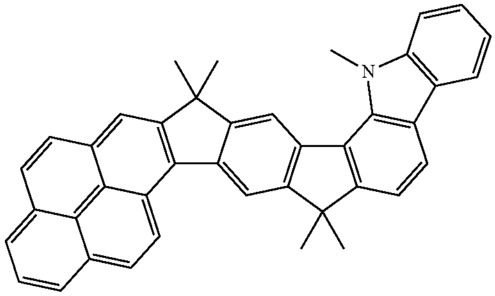

-continued
(117)
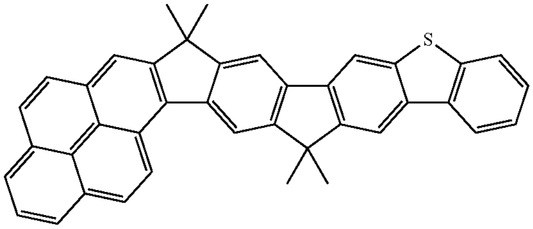
(118)
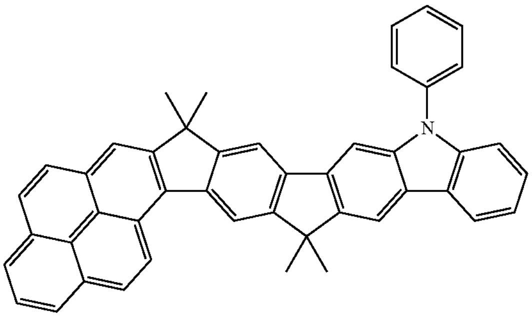
(119)
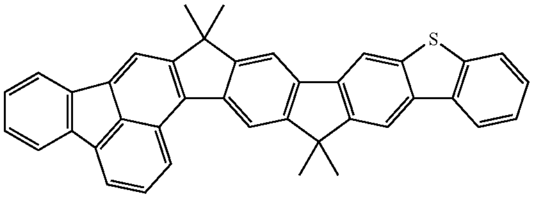
(120)
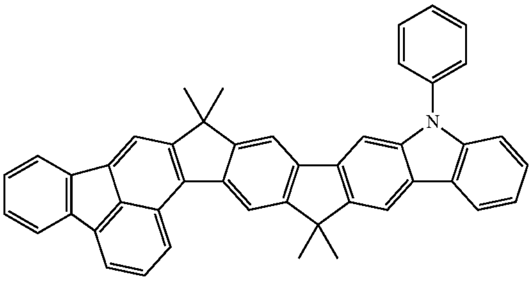
(121)
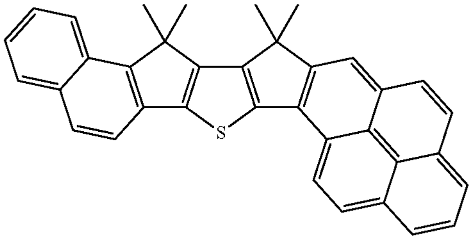
(122)
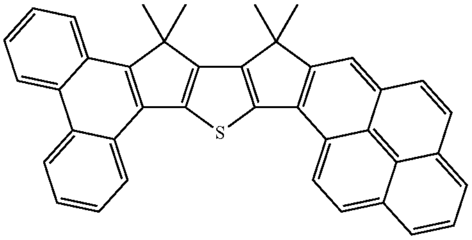
(123)
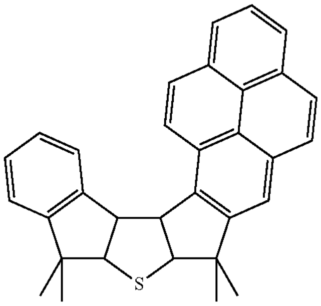
(124)
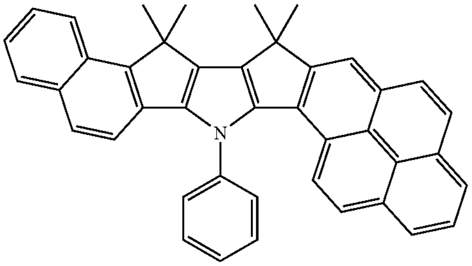
(125)
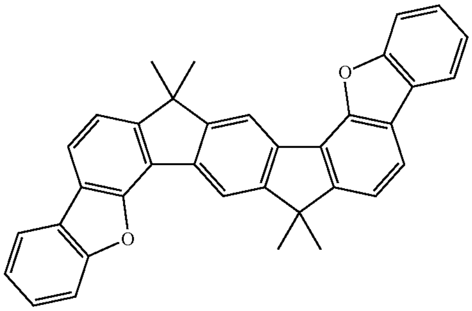
(126)
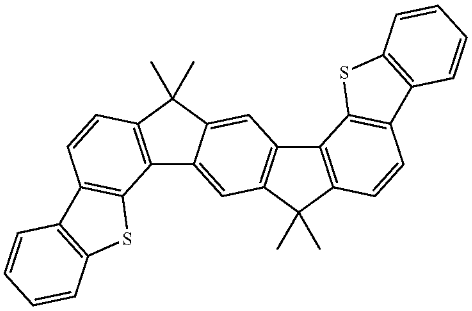

-continued
(127)
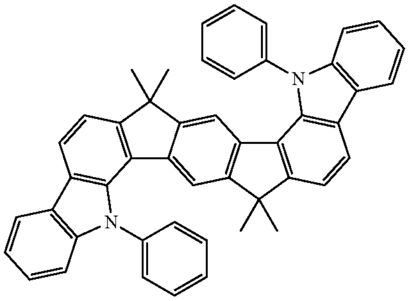
(128)
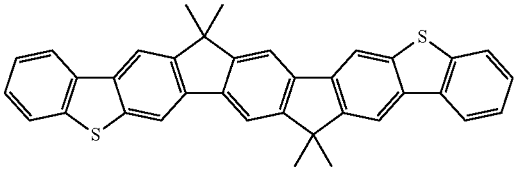
(129)
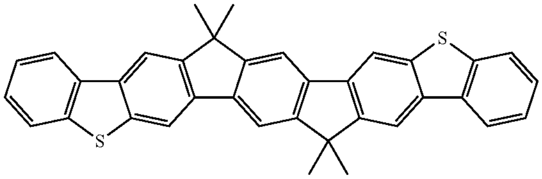
(130)
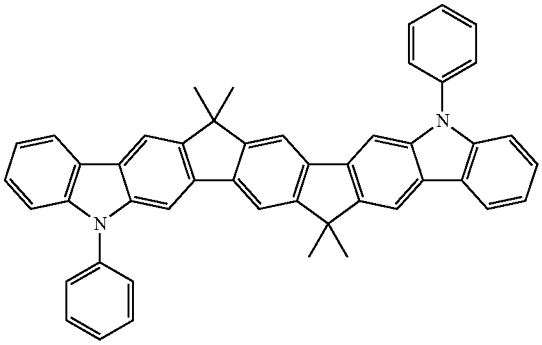
(131)
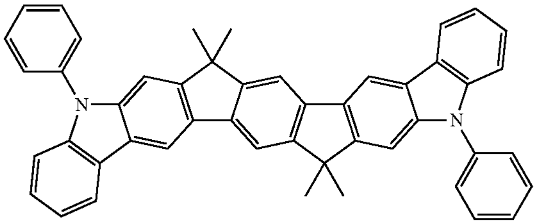
(132)
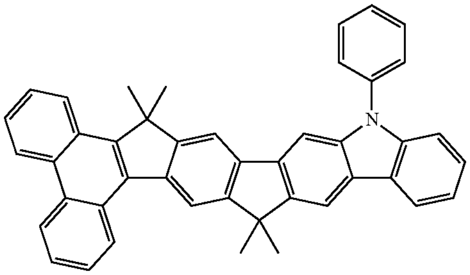
(133)
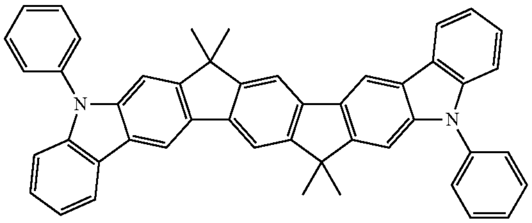
(134)
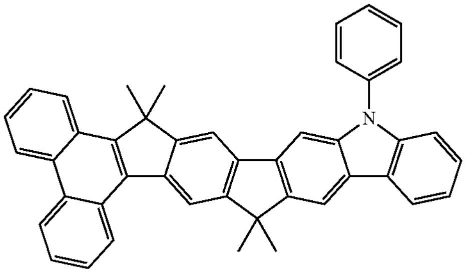
(135)
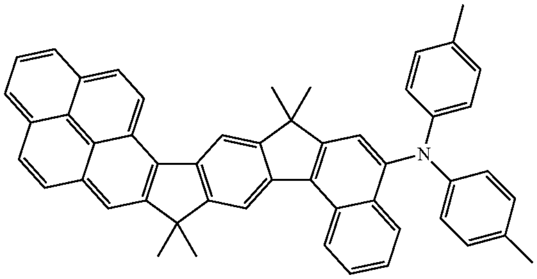
(136)
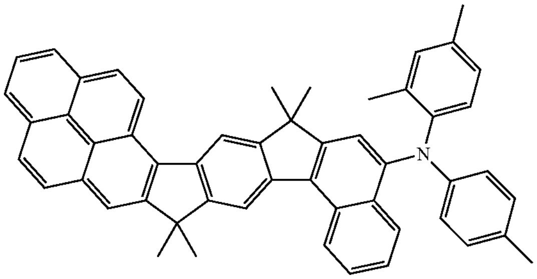

-continued
(137)
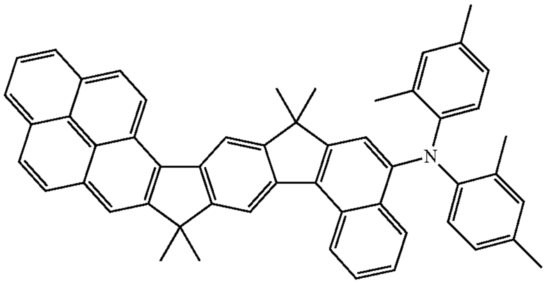
(138)
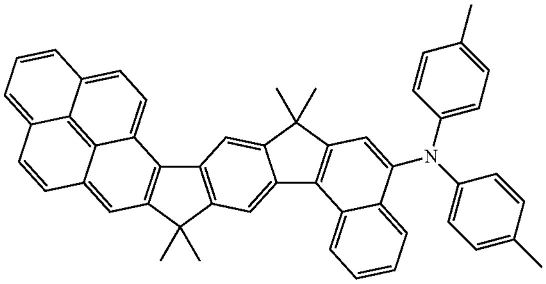
(139)
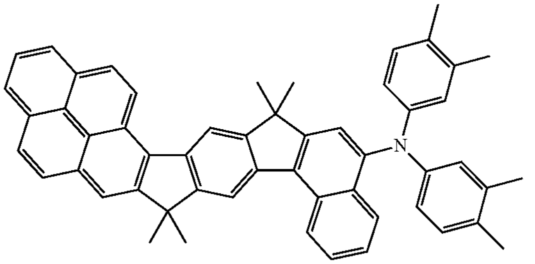
(140)
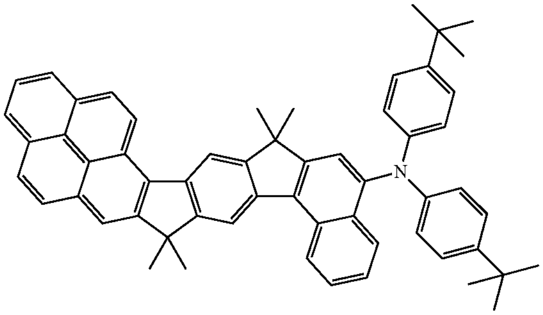
(141)
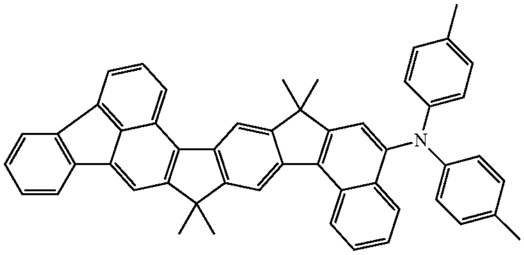
(142)
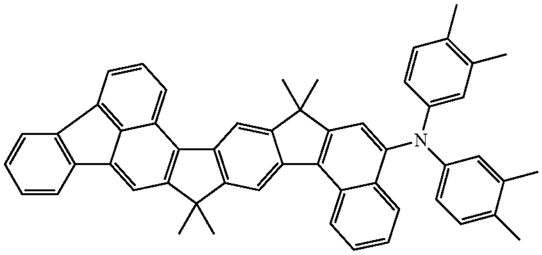
(143)
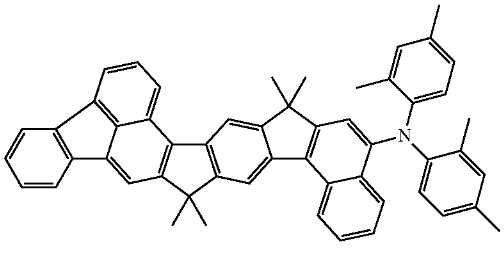
(144)
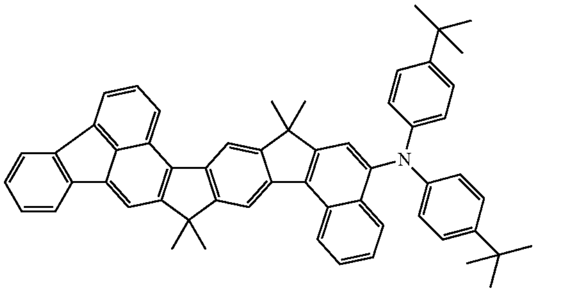

-continued
(145)
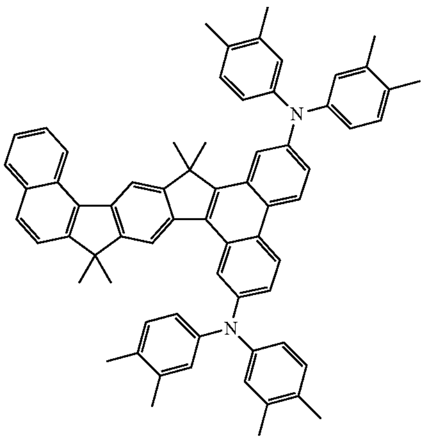
(146)
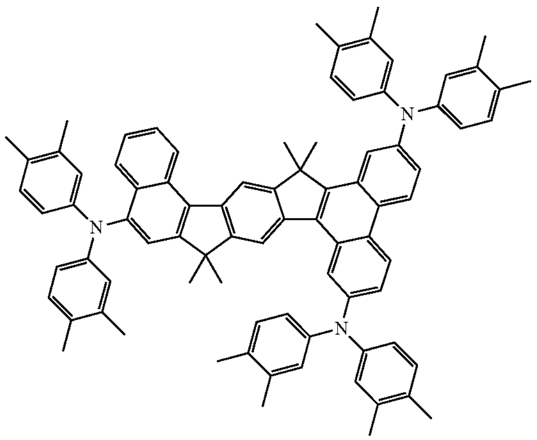
(147)
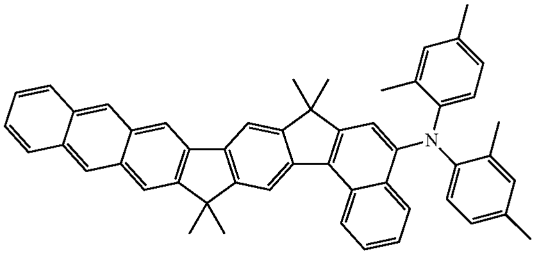
(148)
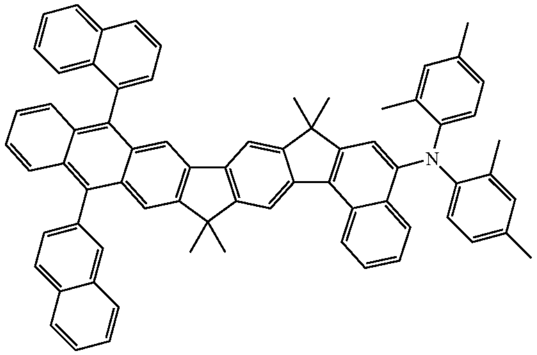
(149)
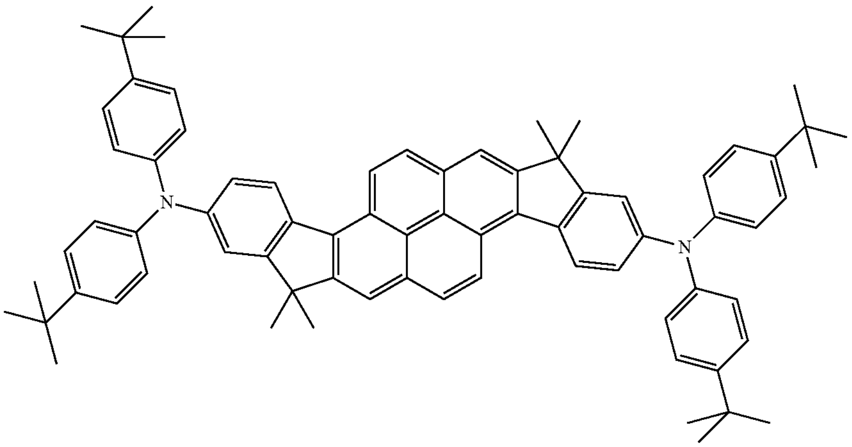

-continued
(150)
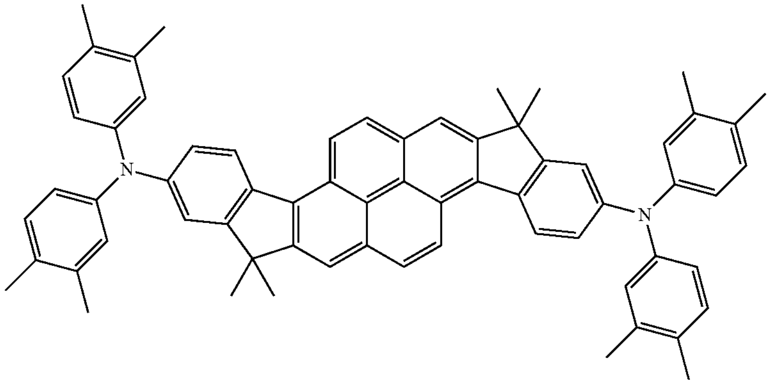
(151)
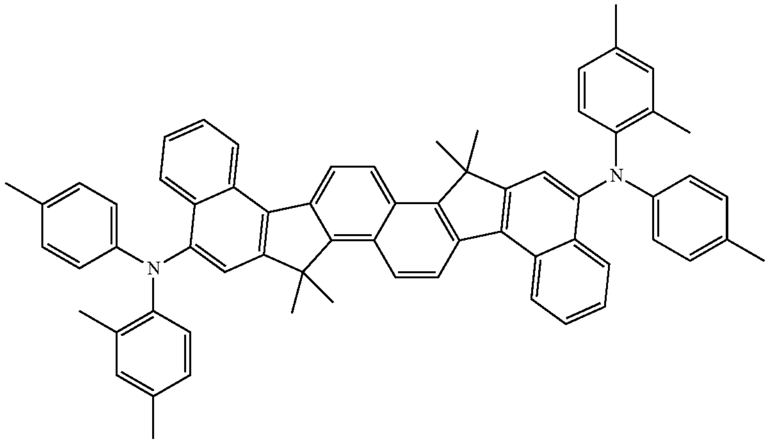
(152)
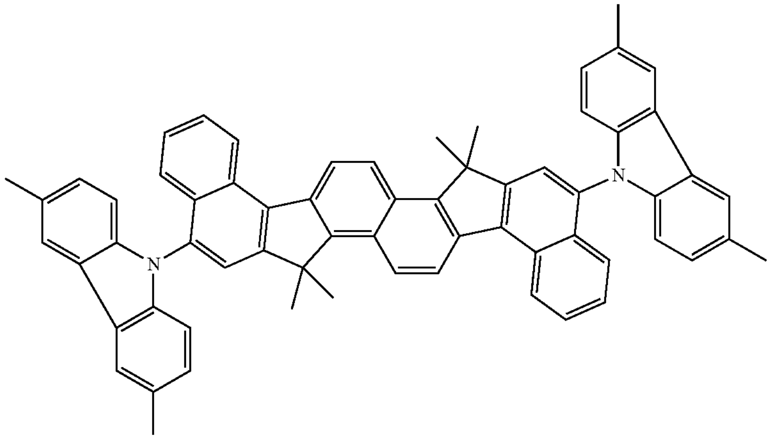
(153)
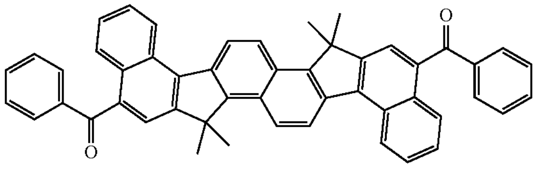
(154)
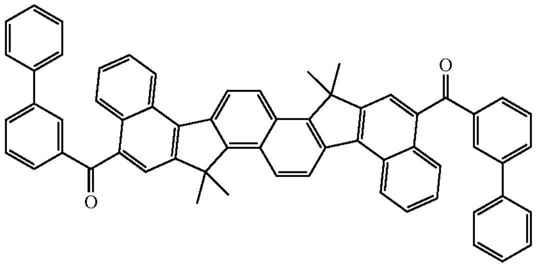

-continued
(155)
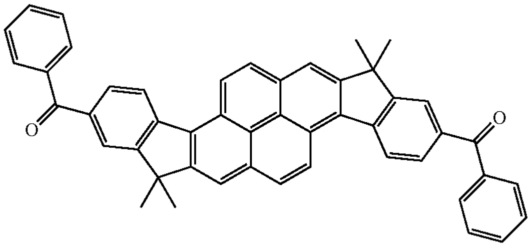
(156)
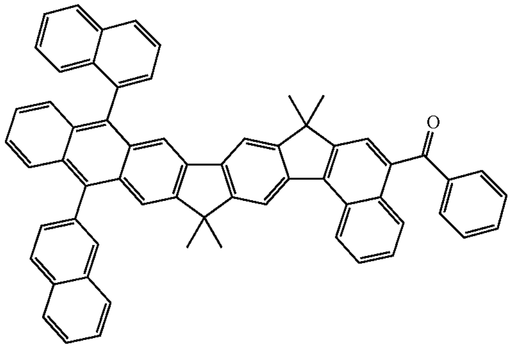
(157)
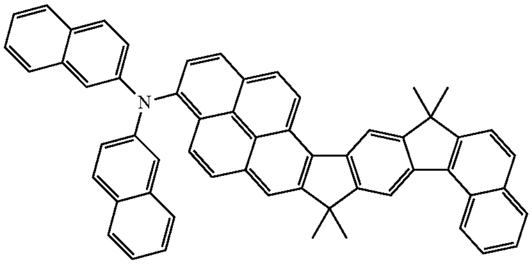
(158)
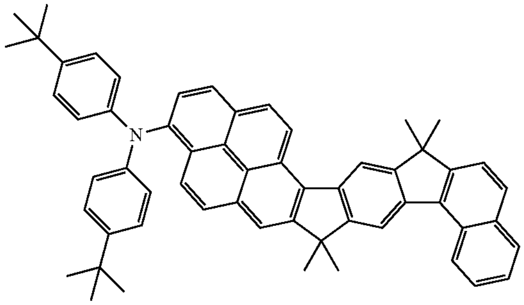
(159)
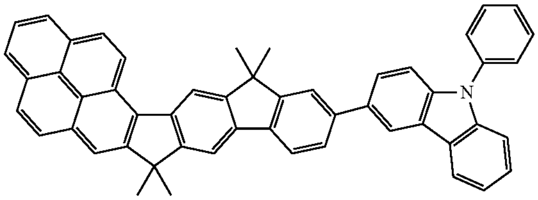
(160)
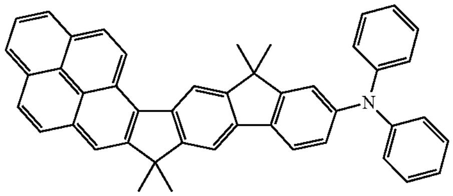
(161)
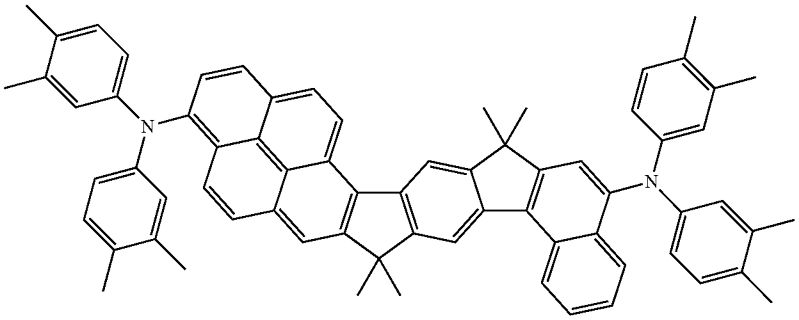
(162)
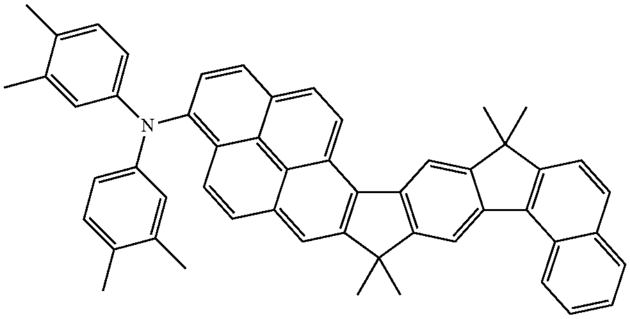

(163)
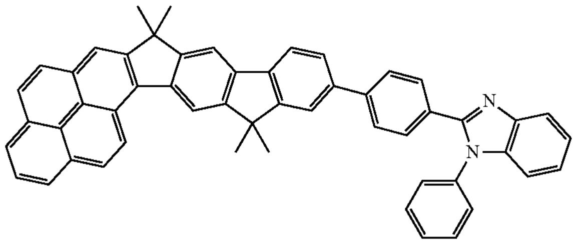
(164)
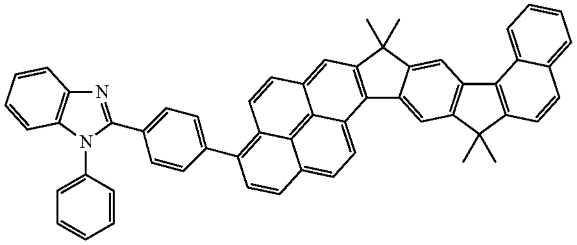
(165)
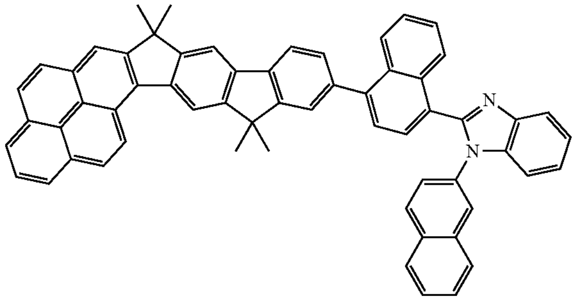
(166)
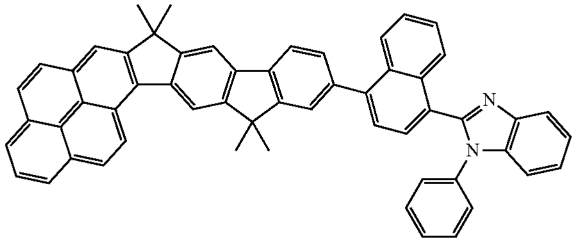
(167)
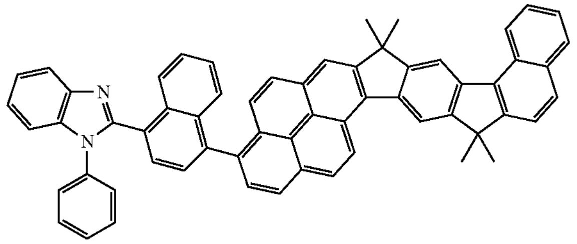
-continued
(168)
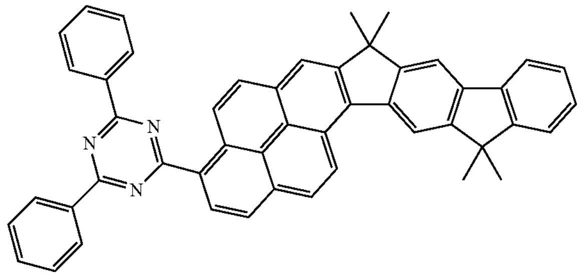
(169)
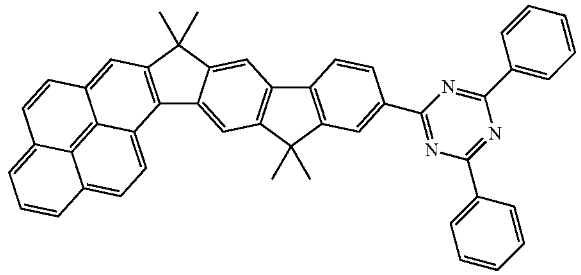
(170)
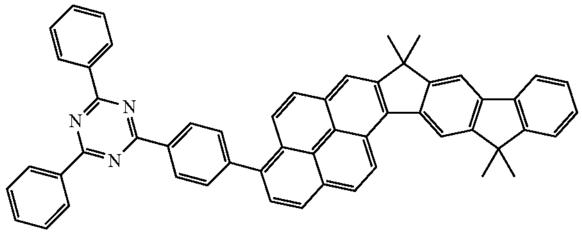
(171)
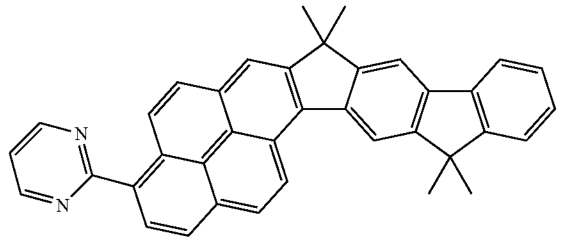
(172)
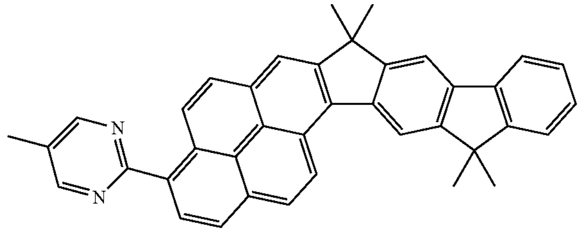
(173)
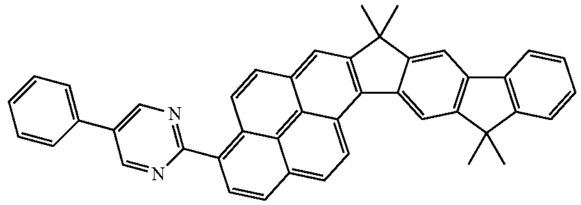

-continued
(174)
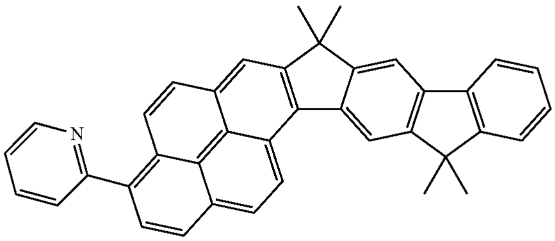
(175)
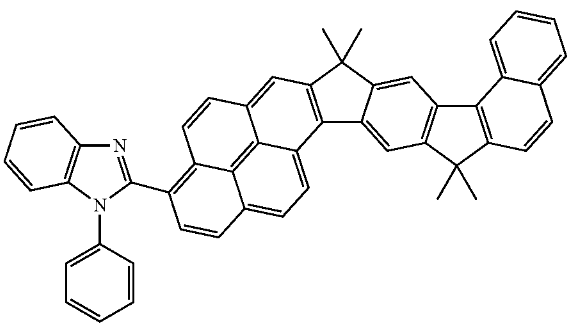
(176)
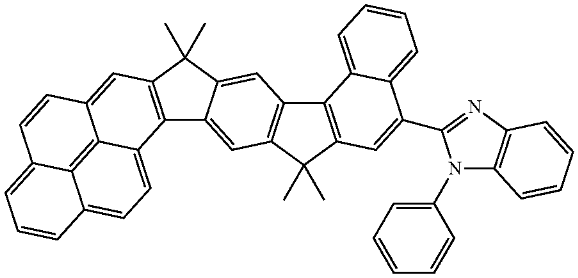
(177)
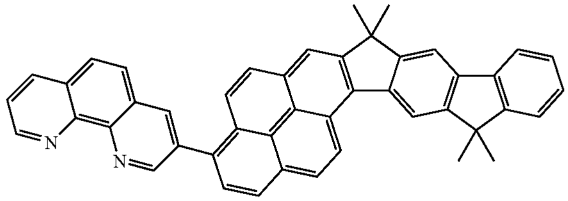
(178)
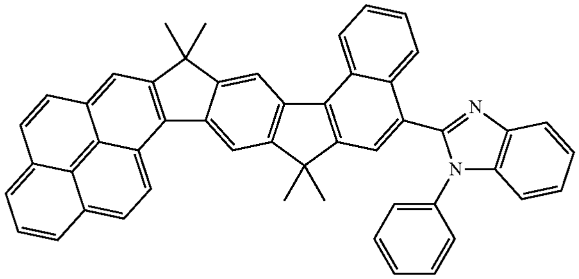
-continued
(179)
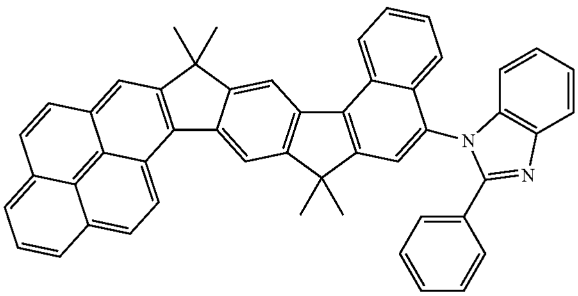
(180)
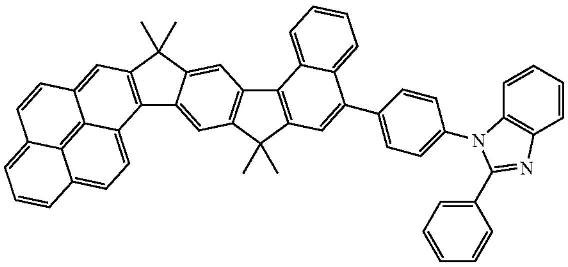
(181)
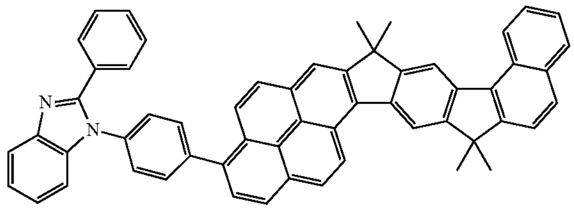
(182)
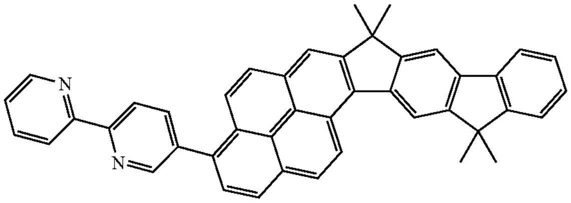
(183)
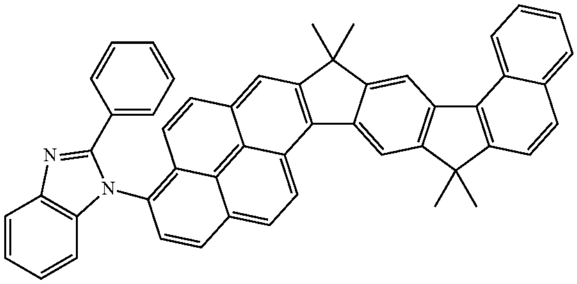

-continued
(184)
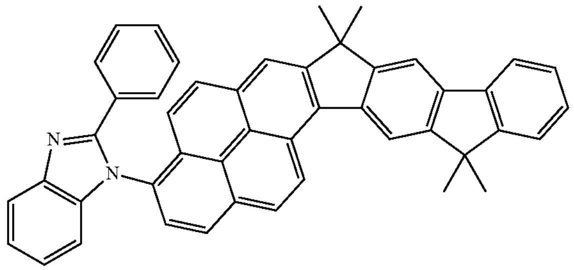
(185)
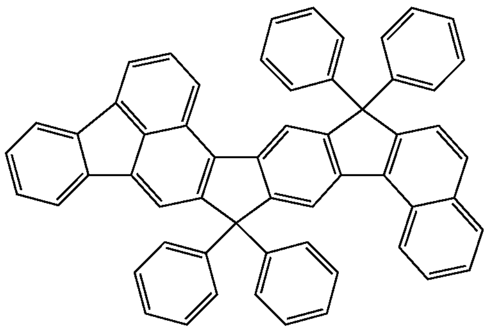
(186)
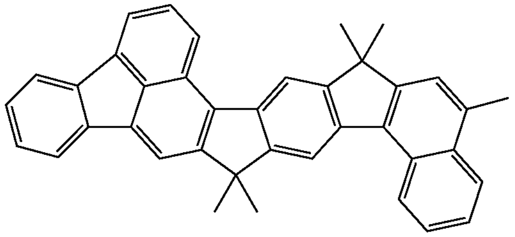
(187)
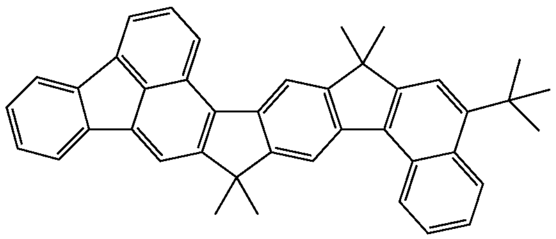
(188)
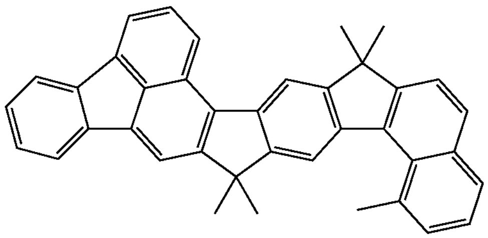
-continued
(189)
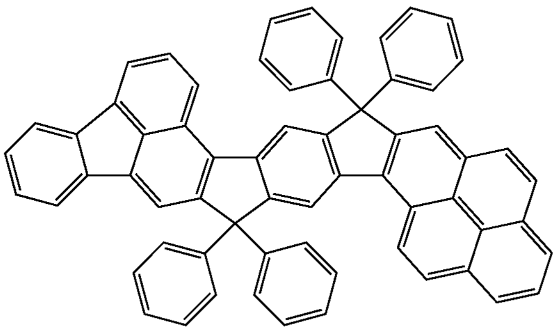
(190)
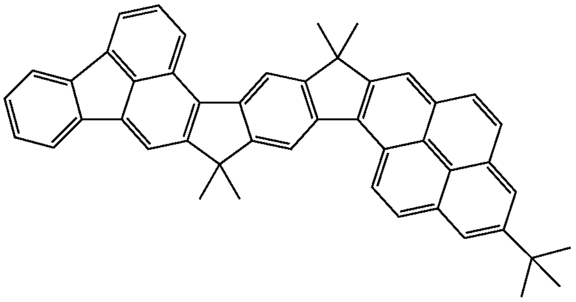
(191)
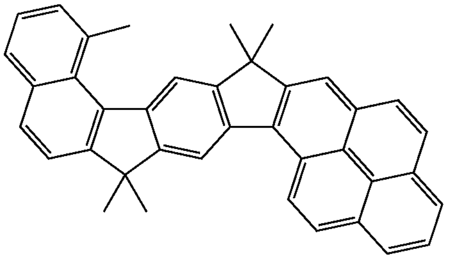
(192)
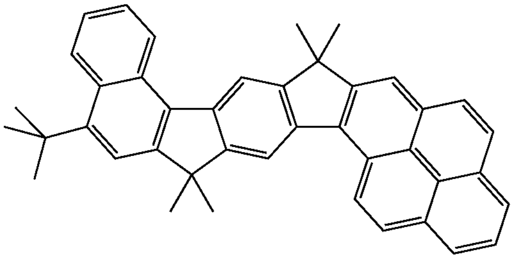
(193)
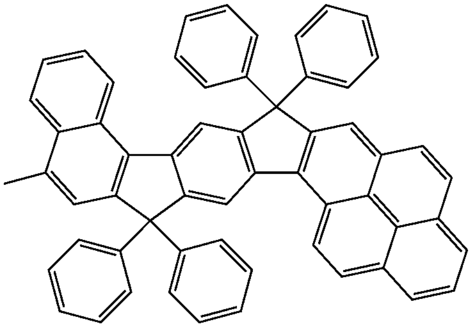

-continued
(194)
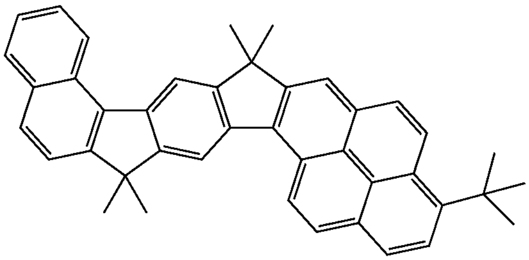
(195)
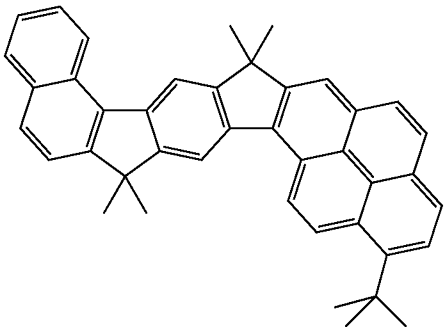
(196)
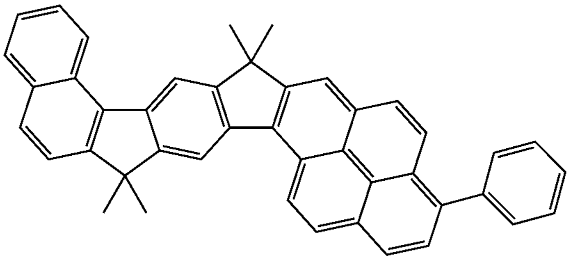
(197)
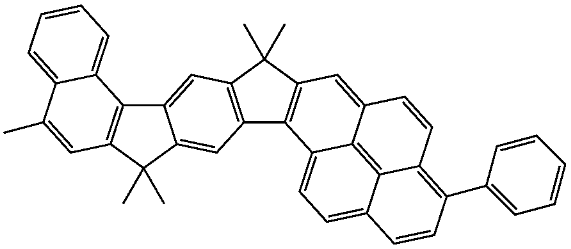
(198)
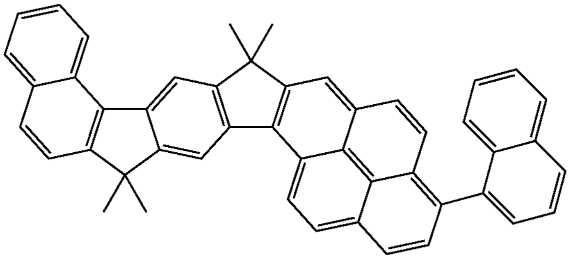
-continued
(199)
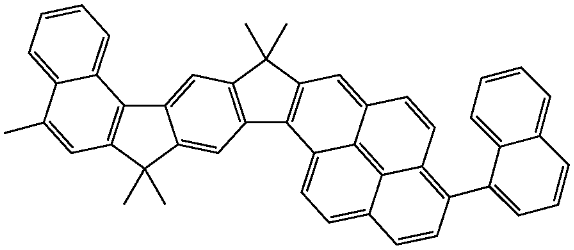
(200)
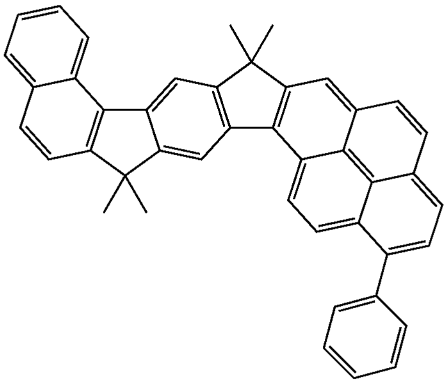
(201)
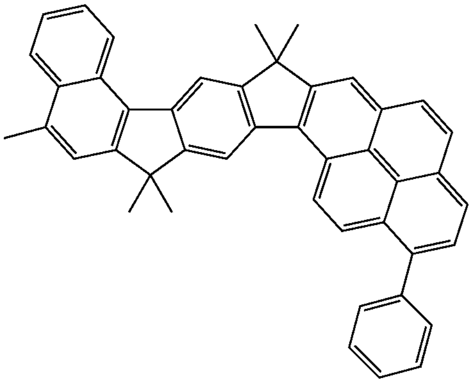
(202)
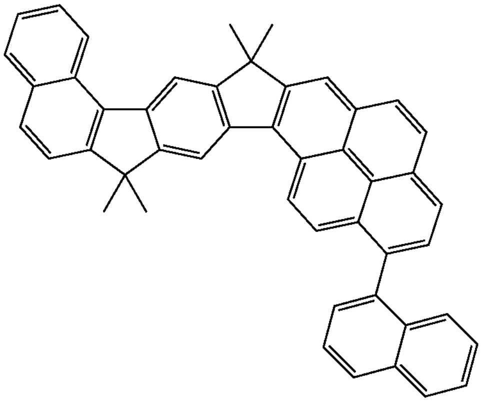

-continued
(203)
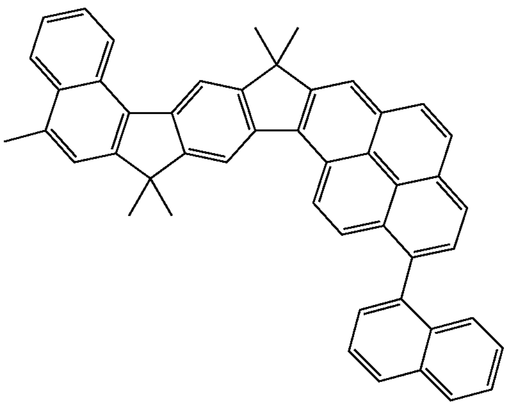
(204)
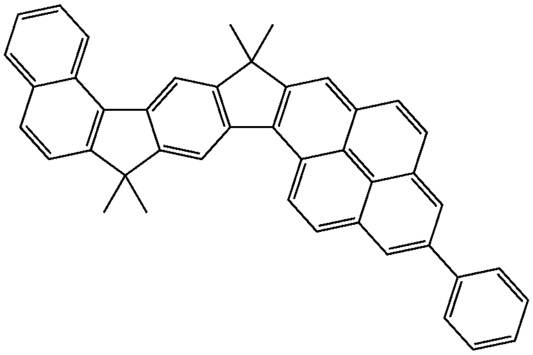
(205)
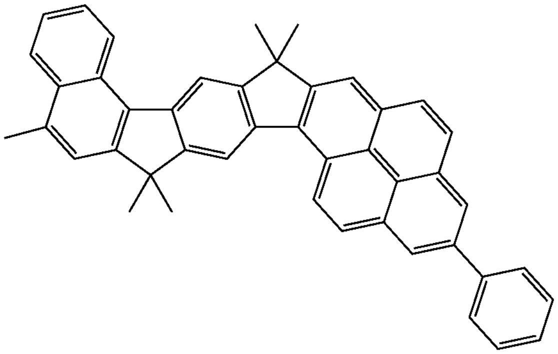
(206)
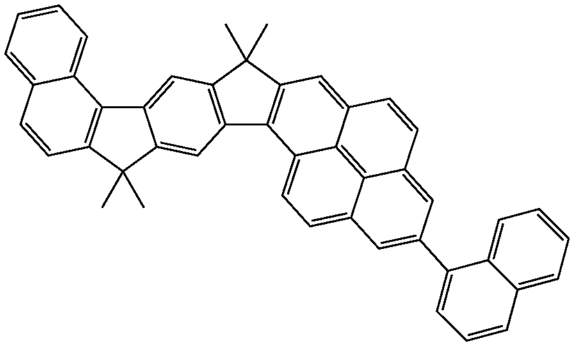
-continued
(207)
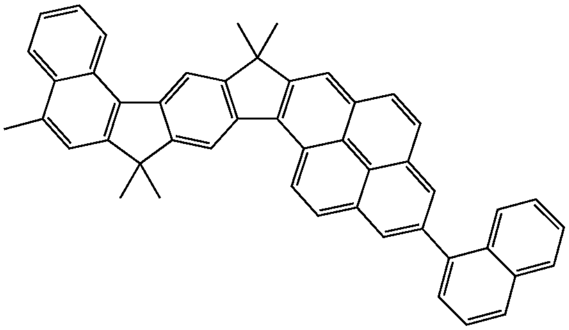
(208)
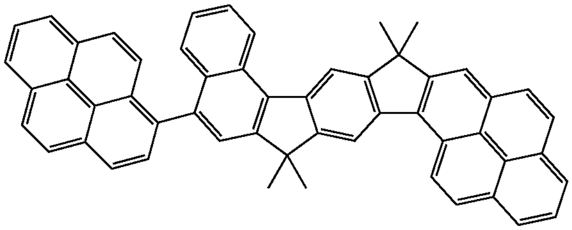
(209)
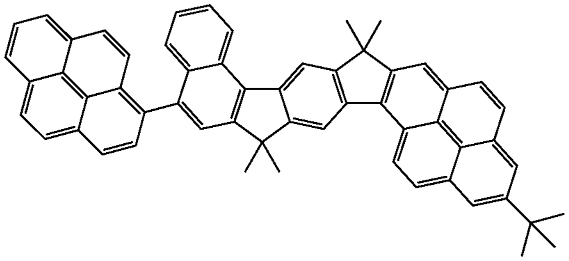
(210)
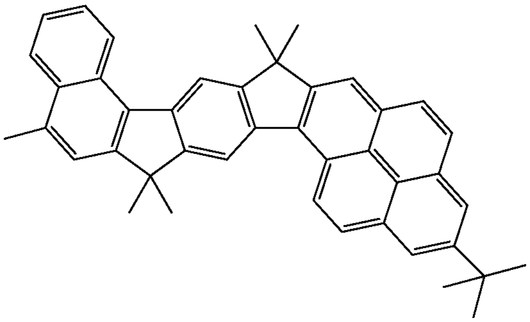
(211)
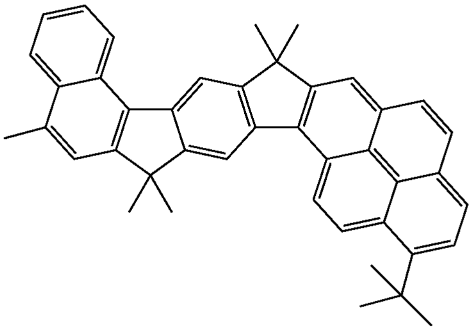

-continued
(212)
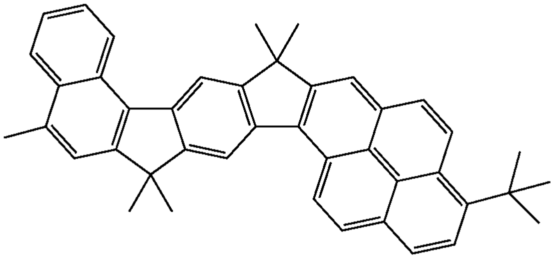
(213)
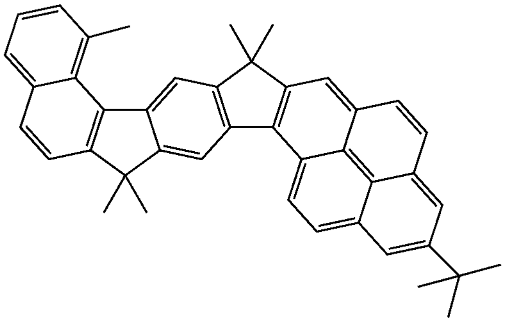
(214)
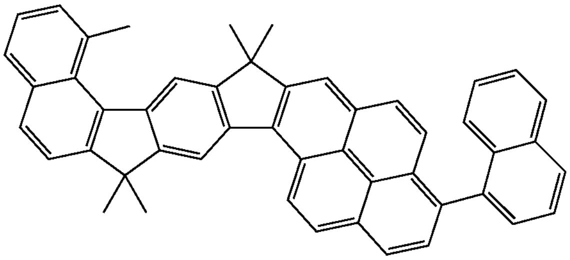
(215)
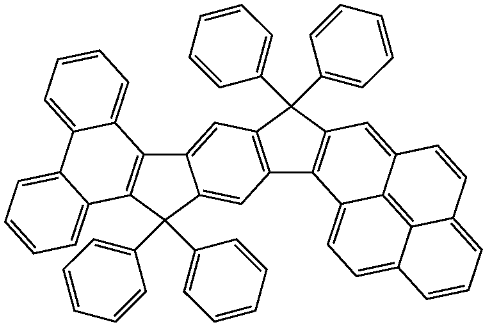
(216)
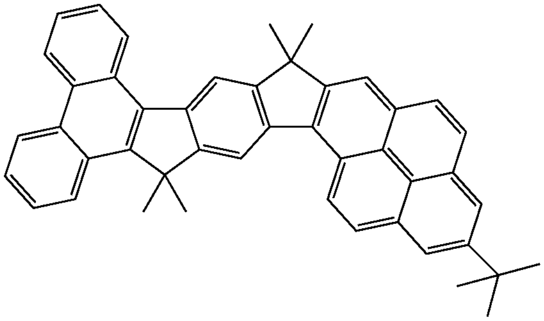
-continued
(217)
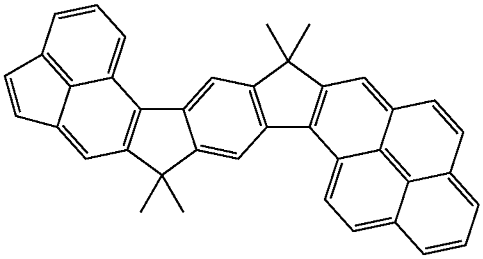
(218)
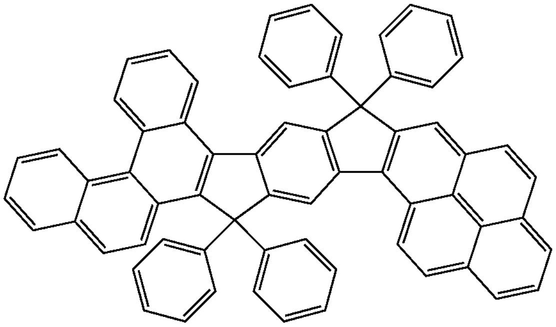
(219)
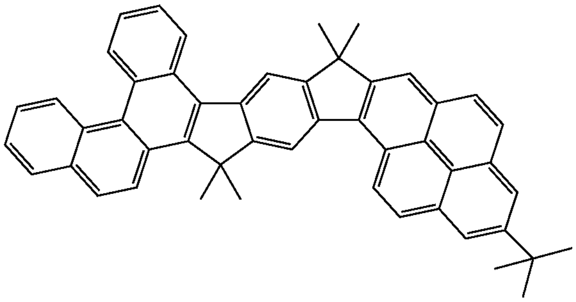
(220)
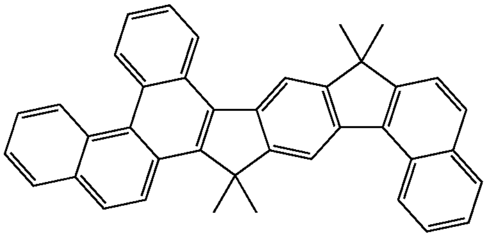
(221)
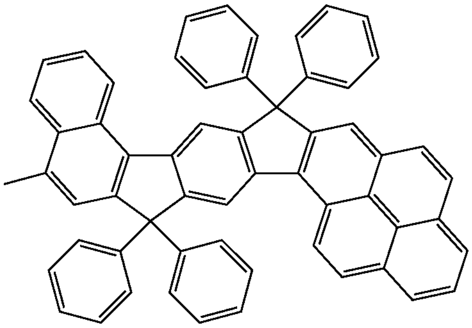

-continued
(222)
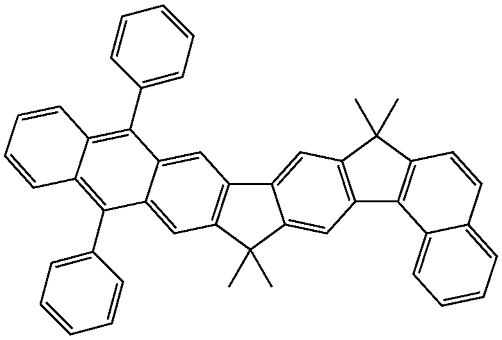
(223)
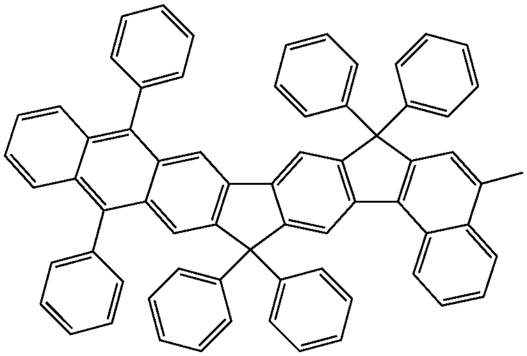
(224)
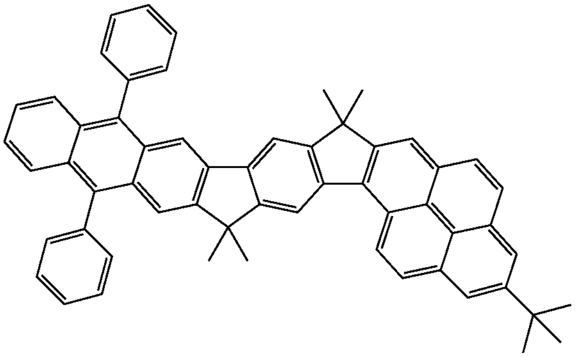
(225)
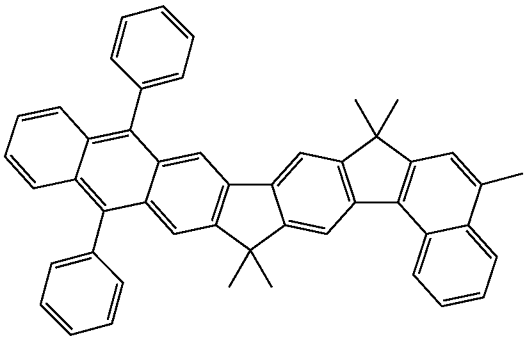
-continued
(226)
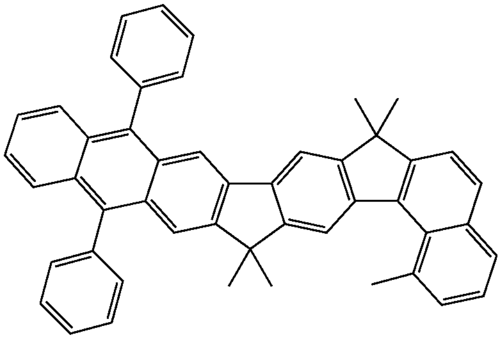
(227)
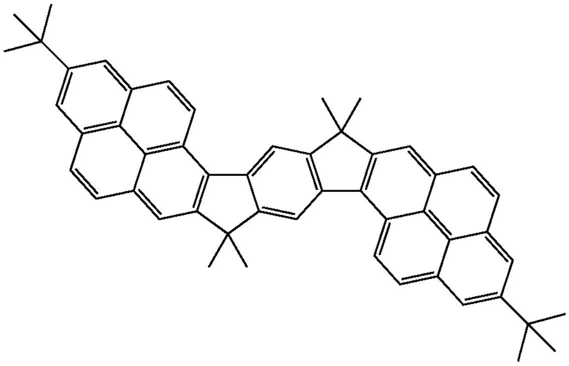
(228)
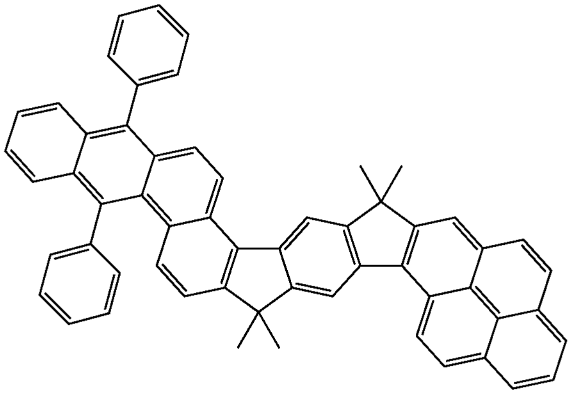
(229)
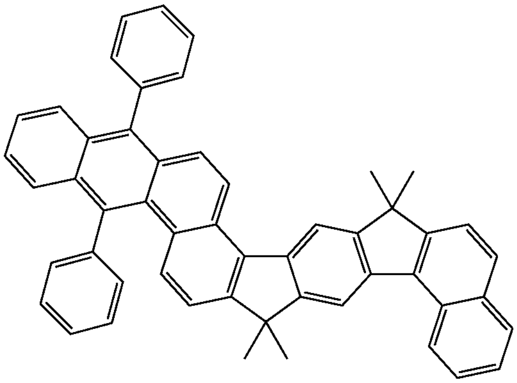

-continued
(230)
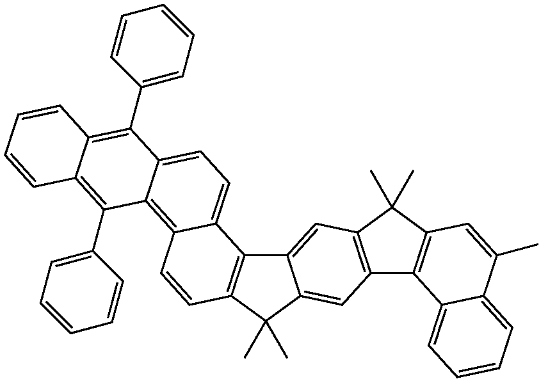
(231)
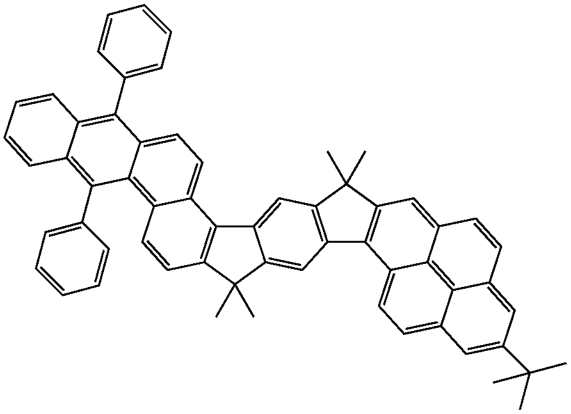
(232)
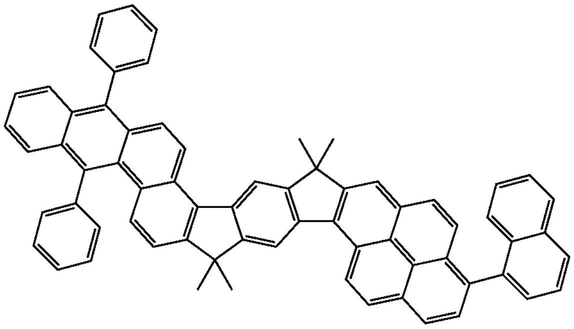
(233)
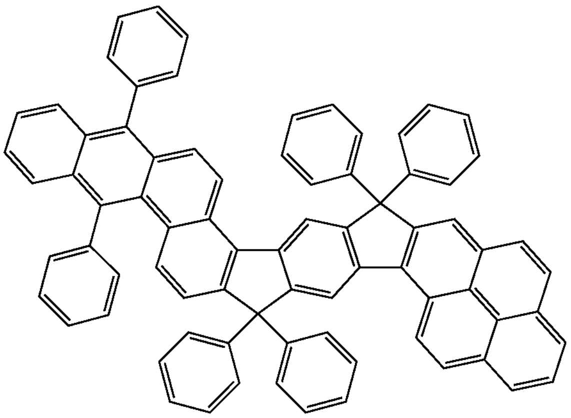
-continued
(234)
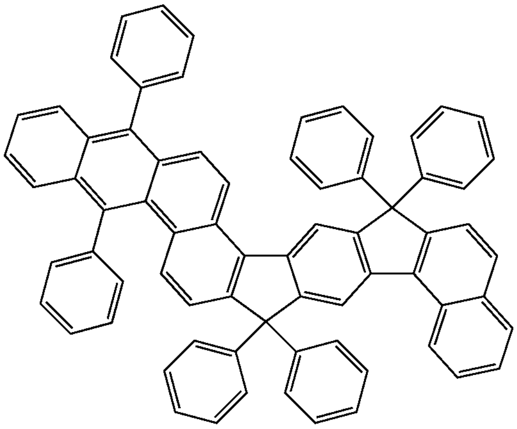
(235)
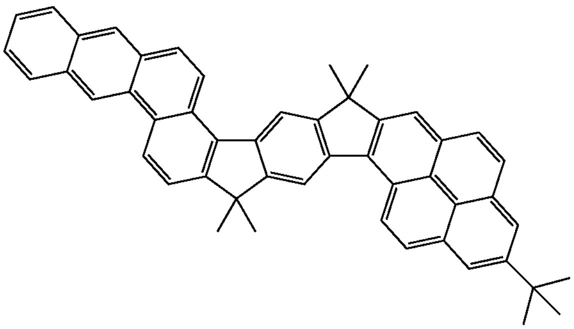
(236)
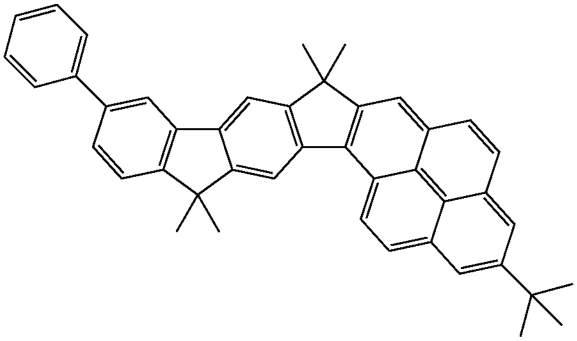
(237)
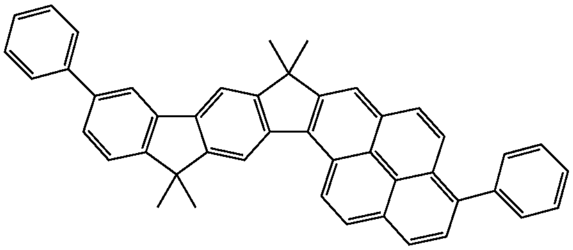

-continued (238)

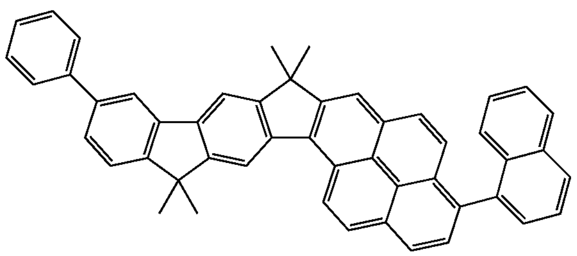

(239)

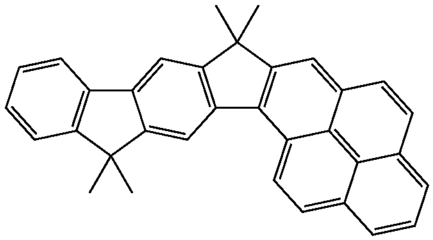

(240)

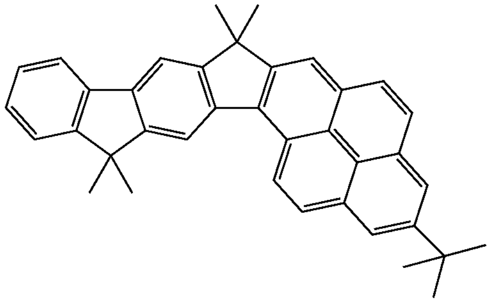

(241)

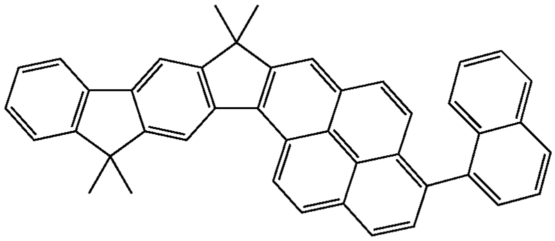

(242)

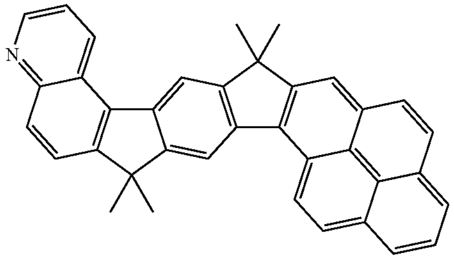

-continued (243)

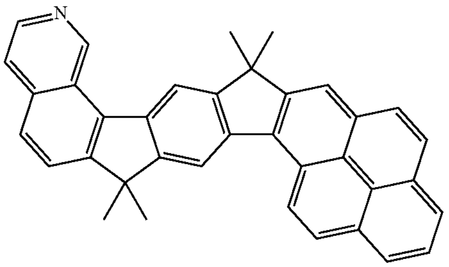

(244)

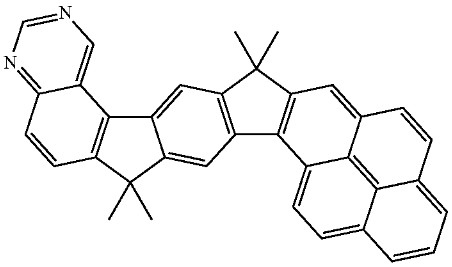

(245)

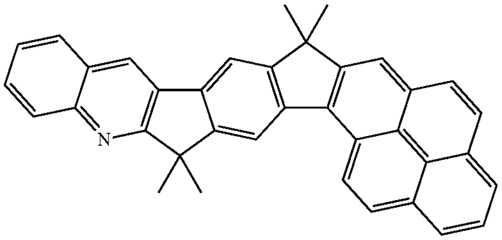

(246)

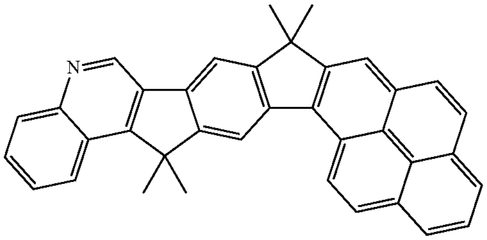

The compounds according to the invention can be prepared by synthesis steps known to the person skilled in the art, such as, for example, Suzuki coupling and cyclisation reactions, as shown in Scheme 1 for compounds of the formula (112). The synthesis can be carried out entirely analogously with other aryl groups $Ar^1$, $Ar^2$ and $Ar^3$. It is likewise possible firstly to carry out the coupling with the naphthalene and then the coupling with the pyrene.

Scheme 1:

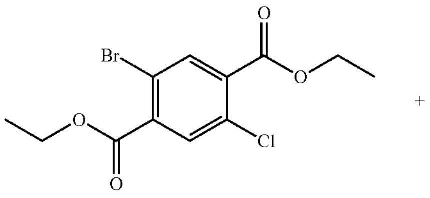

-continued

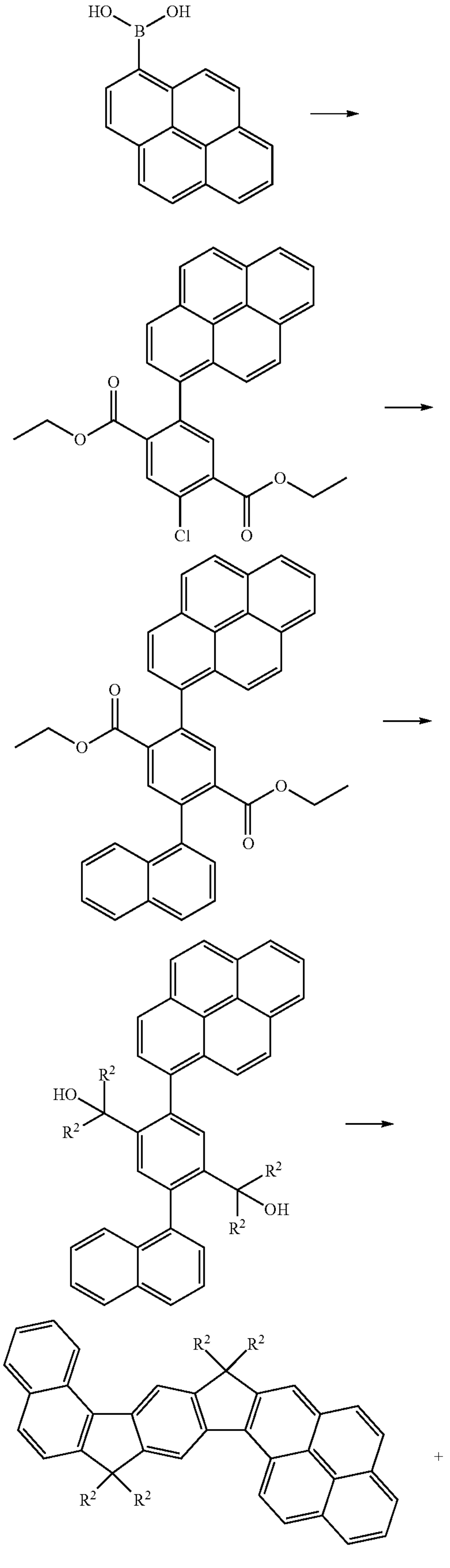

-continued

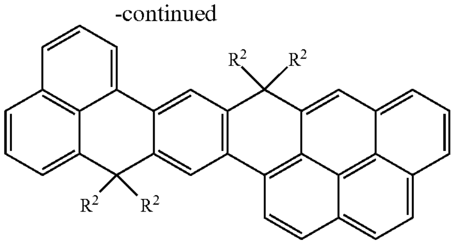

To this end, a boronic acid derivative of the aromatic group $Ar^1$, in this case pyreneboronic acid, is coupled to a bromochlorobis(carboxylate) derivative of the aromatic group $Ar^2$, in this case diethyl 2-bromo-5-chloro-terephthalate, with palladium catalysis, followed by coupling of a boronic acid derivative of the aromatic group $Ar^3$, in this case 1-naphthylboronic acid. These selective coupling steps succeed due to different reactivity of chlorine and bromine. The carboxylate groups are converted into the corresponding alcohol by the addition reaction of an alkyl- or arylmetal compound, for example an alkyl- or aryllithium compound or an alkyl- or aryl-Grignard compound. This alcohol can be cyclised under acidic conditions, where the precise reaction conditions determine whether a five-membered ring, a six-membered ring or a mixture of five-membered ring and six-membered ring is formed. If a mixture of five-membered ring and six-membered ring is formed, this can be separated, for example by recrystallisation or chromatographic methods. This reaction is possible entirely analogously with other arylboronic acid derivatives and other chlorobromo-dicarboxylic acid derivatives. It is likewise possible to employ aryl groups that are already substituted. Furthermore, the use of a 3-bromo-6-chlorophthalic acid ester enables the corresponding cis-linked derivatives to be synthesised. It is likewise possible to use other C—C linking reactions instead of a Suzuki coupling.

The present invention therefore furthermore relates to a process for the preparation of the compounds according to the invention, comprising the following reaction steps:

a) coupling of suitably substituted $Ar^1$, $Ar^2$ and $Ar^3$, where suitable substituents can be, for example, carboxylate groups; and b) cyclisation of the substituents for introduction of the bridges X.

Preference is given to a process for the preparation of the compounds of the formula (1), comprising the following reaction steps:

a) coupling of a boronic acid or a boronic acid derivative of $Ar^1$ to a bromochlorobis(carboxylate) derivative of $Ar^2$;

b) coupling of the reaction product from a) to a boronic acid or a boronic acid derivative of $Ar^3$;

c) conversion of the carboxylate groups into alcohol groups; and d) cyclisation under acidic conditions.

The compounds according to the invention described above, in particular compounds which are substituted by reactive leaving groups, such as bromine, iodine, or boronic acid or boronic acid ester, can also be used as monomers for the production of corresponding conjugated, partially conjugated or non-conjugated polymers or oligomers or as the core of dendrimers. The polymerisation here is preferably carried out via the halogen functionality or the boronic acid functionality.

The invention furthermore relates to polymers, oligomers or dendrimers comprising one or more compounds according to the invention, where one or more radicals $R^1$ or $R^2$ represent bonds from a compound to the polymer or dendrimer. These polymers, oligomers or dendrimers may be conjugated, partially conjugated or non-conjugated.

The same preferences as described above apply to the polymer recurring units according to the invention.

These compounds are homopolymerised or copolymerised with further monomers. Suitable and preferred monomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or the unpublished application DE 102005037734.3) or also a plurality of these units. These polymers usually also contain further units, for example emitting (fluorescent or phosphorescent) units, such as, for example, vinyltriarylamines (for example in accordance with the unpublished application DE 102005060473.0) or phosphorescent metal complexes (for example in accordance with WO 06/003000), and/or charge-transport units, in particular those based on tri-arylamines The compounds of the formula (1) according to the invention and the corresponding polymers, oligomers or dendrimers are suitable for use in electronic devices, in particular in organic electroluminescent devices (OLEDs, PLEDs). Depending on the structure, the compounds are employed in different functions and layers. The precise use of the compounds depends, in particular, on the choice of the aryl groups $Ar^1$, $Ar^2$ and $Ar^3$ and on the groups X.

The invention therefore furthermore relates to the use of the compounds of the formula (1) according to the invention or the corresponding polymers, oligomers or dendrimers in electronic devices, in particular in organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electro-chemical cells (LECs), organic photoreceptors or organic laser diodes (O-Laser).

The invention furthermore relates to electronic devices, in particular the electronic devices mentioned above, comprising at least one compound of the formula (1) or a corresponding oligomer, polymer or dendrimer, in particular organic electroluminescent devices comprising anode, cathode and at least one emitting layer, characterised in that at least one organic layer, which may be an emitting layer or another layer, comprises at least one compound of the formula (1).

The preferred embodiments mentioned above apply to the use in the electronic device.

Apart from cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. However, it should be pointed out that each of these layers does not necessarily have to be present, and the choice of the layers always depends on the compounds used and in particular also on whether it is a fluorescent or phosphorescent electroluminescent device.

The organic electroluminescent device may also comprise a plurality of emitting layers, where at least one organic layer comprises at least one compound of the formula (1) or a corresponding oligomer, polymer or dendrimer. These emission layers particularly preferably have in total a plurality of emission maxima between 380 nm and 750 nm; resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formula (1) or a corresponding oligomer, polymer or dendrimer and where the three layers exhibit blue, green and orange or red emission (for the basic structure, see, for example, WO 05/011013) and systems which have more than three emitting layers. Emitters which have broad-band emission bands and thus exhibit white emission are likewise suitable for white emission.

It is particularly preferred for the compounds of the formula (1) to be employed in an emitting layer. In this case, they can be employed either as emitting material (emitting dopant) or as host material for an emitting material. The compounds of the formula (1) are particularly preferably suitable as emitting material.

If the compound of the formula (1) is employed as emitting material in an emitting layer, it is preferably employed in combination with a host material. A host material is taken to mean the component in a system comprising host and dopant that is present in the higher proportion in the system. In the case of a system comprising one host and a plurality of dopants, the host is taken to mean the component whose proportion in the mixture is the highest.

The proportion of the compound of the formula (1) in the mixture of the emitting layer is between 0.1 and 50.0% by vol., preferably between 0.5 and 20.0% by vol., particularly preferably between 1.0 and 10.0% by vol. Correspondingly, the proportion of the host material is between 50.0 and 99.9% by vol., preferably between 80.0 and 99.5% by vol., particularly preferably between 90.0 and 99.0% by vol.

Suitable host materials for this purpose are materials from various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with the unpublished application DE 102007024850.6). Particularly preferred host materials are selected from the classes of the oligoarylenes containing naphthalene, anthracene, benzanthracene and/or pyrene, or atropisomers of these compounds, the ketones, the phosphine oxides and the sulfoxides. Very particularly preferred host materials are selected from the classes of the oligoarylenes containing anthracene, benzanthracene and/or pyrene, or atropisomers of these compounds. For the purposes of this invention, an oligoarylene is intended to be taken to mean a compound in which at least three aryl or arylene groups are bonded to one another.

Preferred host materials are, in particular, selected from compounds of the formula (138)

$$Ar^4—(Ar^5)_p—Ar^6 \qquad \text{formula (138)}$$

where $Ar^4$, $Ar^5$, $Ar^6$ are on each occurrence, identically or differently, an aryl or heteroaryl group having 5 to 30 aromatic ring atoms, which may be substituted by one or more radicals $R^1$, and $R^1$ and p have the same meaning as described above; the sum of the π electrons in $Ar^4$, $Ar^5$ and $Ar^6$ is at least 30 if p=1 and is at least 36 if p=2 and is at least 42 if p=$^3$.

The group $Ar^5$ in the host materials of the formula (138) particularly preferably stands for anthracene, which may be substituted by one or more radicals $R^1$, and the groups $Ar^4$ and $Ar^6$ are bonded in the 9- and 10-position. Very particularly preferably, at least one of the groups $Ar^4$ and/or $Ar^6$ is a condensed aryl group selected from 1- and 2-naphthyl, 2-, 3- and 9-phenanthrenyl and 2-, 3-, 4-, 5-, 6- and 7-benzanthracenyl, each of which may be substituted by one or more radicals $R^1$.

It is furthermore preferred for the compound of the formula (1) to be employed as host material, in particular for a fluorescent dopant.

Suitable fluorescent emitters are selected, example, from the class of the monostyrylamines, distyrylamines, tristyrylamines, tetrastyrylamines, styrylphosphines, styryl ethers and arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. Preferred examples thereof are aromatic anthracenamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position or in the 2-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoindenofluorenamines or benzoindenofluorened amines, for example in accordance with WO 08/006449, and dibenzoindenofluorenamines or dibenzoindenofluorenediamines, for example in accordance with WO 07/140847. Examples of dopants from the class of the styrylamines are substituted or unsubstituted tristilbenamines or the dopants described in WO 06/000388, WO 06/058737, WO 06/000389, WO 07/065549 and WO 07/115610.

Depending on the substitution pattern, the compounds of the formula (1) can also be employed in other layers.

A possible further use of compounds of the formula (1) is the use as hole-transport or hole-injection material in a hole-transport or hole-injection layer. This use is particularly suitable if one or more bridges X stand for S or $NR^2$.

A further possible use of compounds of the formula (1) is the use as electron-transport material in an electron-transport layer. Particularly suitable for this purpose are compounds of the formula (1) which are substituted by at least one electron-deficient heteroaromatic group. Electron-deficient heteroaromatic groups are 6-membered heteroaromatic groups having at least one nitrogen atom and corresponding condensed systems, for example pyridine, pyrazine, pyrimidine, pyridazine, triazine, quinoline, quinoxaline or phenanthroline, or 5-membered heteroaromatic groups having at least one nitrogen atom and a further heteroatom selected from N, O and S, and corresponding condensed systems, for example pyrazole, imidazole, oxazole, oxadiazole or benzimidazole. A suitable electron-transport material is furthermore compounds in which $Ar^1$, $Ar^2$ and/or $Ar^3$ stand for an electron-deficient heterocycle. If the compounds of the formula (1) are used as electron-transport material, the bridge X preferably stands for $C(R^2)_2$. In addition, the compounds are also suitable as electron-transport materials if at least one bridge X, preferably both bridges X, stand for C═O, P(═O)$R^2$, SO or $SO_2$.

Preference is furthermore given to an organic electroluminescent device, characterised in that one or more layers are coated by a sublimation process. In this, the materials are vapour-deposited in vacuum sublimation units at an initial pressure below $10^{-5}$ mbar, preferably below $10^{-6}$ mbar. However, it is also possible for the initial pressure to be even lower, for example below $10^{-7}$ mbar.

Preference is likewise given to an organic electroluminescent device, characterised in that one or more layers are coated by the OVPD (organic vapour phase deposition) process or with the aid of carrier-gas sublimation. Here, the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light-induced thermal imaging, thermal transfer printing) or ink-jet printing. Soluble compounds of the formula (1) are necessary for this purpose. High solubility can be achieved by suitable substitution of the compounds. A coating method from solution is also particularly suitable for oligomers, polymers or dendrimers.

For application from solution, solutions of the compounds according to the invention in one or more solvents are necessary. The invention therefore furthermore relates to solutions of the compounds according to the invention or corresponding oligomers, polymers or dendrimers in one or more solvents. The solution here may also comprise further constituents, for example a host material for the compound according to the invention.

On use in organic electroluminescent devices, the compounds according to the invention have the following surprising advantages over the prior art:

1. The compounds according to the invention exhibit dark-blue emission on use as emitting materials in organic electroluminescent devices (CIE y in the range from 0.10 to 0.13) and are thus eminently suitable for the production of dark-blue-emitting electroluminescent devices.
2. A suitable choice of the groups $Ar^1$, $Ar^2$ and $Ar^3$ enables the colour location of the emission from the compound to be set simply using the compounds according to the invention. Thus, both deep-blue- and also pale-blue-emitting compounds are accessible, where the colour location can in each case be optimised for the desired use.
3. The electroluminescent devices furthermore exhibit very good efficiencies (EQE>6%).
4. Furthermore, electroluminescent devices comprising the compounds according to the invention exhibit a significant improvement with respect to the lifetime.
5. In particular on use in the electron-injection and -transport layer of doped electron-transport materials which result in an excess of electrons in the device, the compounds according to the invention, if employed as emitters, exhibit significant improvements with respect to efficiency and lifetime compared with emitters in accordance with the prior art which contain diarylamino groups. This is an essential advantage since the very combination of LiQ with benzimidazole derivatives is frequently used as electron-transport material.

The invention is described in greater detail by the following examples, without wishing to restrict it thereby. The person are skilled in the art will be able, without being inventive, to carry out the invention throughout the range disclosed and thus produce further materials and organic electroluminescent devices according to the invention.

EXAMPLES

The following syntheses were carried out under a protective-gas atmosphere, unless indicated otherwise. The starting materials were purchased from ALDRICH or ABCR.

Example 1: Synthesis of 1,1-dimethylbenzindeno-1,1-dimethylindeno-[a]pyrene a) Diethyl 2-chloro-5-pyren-1-ylterephthalate

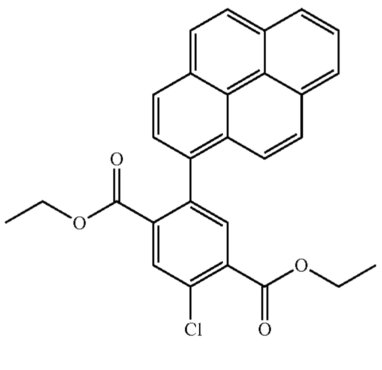 [SMILES: CCOC(=O)c1cc(-c2ccc3ccc4cccc5ccc2c3c45)c(C(=O)OCC)cc1Cl]

28.9 g (103 mmol) of bromopyrene are dissolved in 275 ml of dry THF, the solution is cooled to −75° C., and 52 ml (104 mmol) of a 2 M solution of n-butyllithium are added dropwise at this temperature. The yellow suspension is stirred at −75° C. for 1 h, and 17.5 ml (155 mmol) of trimethyl borate are then added dropwise. After the mixture has been warmed to RT, 34.5 g (103 mmol) of diethyl chlorobromoterephthalate, 22 g (206 mmol) of $Na_2CO_3$, 1.2 g (1.03 mmol) of tetrakis(triphenylphosphine)palladium(0), 140 ml of $H_2O$, 280 nil of toluene and 140 ml of EtOH are added, and the mixture is heated at the boil for 2 h. After the organic phase has been separated off, washed twice with water and dried over $Na_2SO_4$, the solvent is removed in vacuo, and the oil which remains is brought to crystallisation in heptane. Recrystallisation twice gives the product in the form of a colourless solid (33 g, 70%) and a purity of >98%, which is employed in this form in the subsequent reaction.

b) Diethyl 2-naphthalen-1-yl-5-pyren-1-ylterephthalate

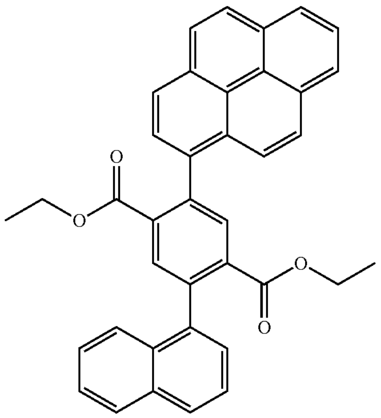 [SMILES: CCOC(=O)c1cc(-c2ccc3ccc4cccc5ccc2c3c45)c(C(=O)OCC)cc1-c1cccc2ccccc12]

43.5 g (90 mmol) of diethyl 2-chloro-5-pyren-1-ylterephthalate, 21.5 g (120 mmol) of 1-naphthylboronic acid and 58.1 g of $Cs_2CO_3$ are initially introduced in 230 nil of dry dioxane, and the mixture is saturated with $N_2$ for 30 min. 2.7 ml of a 1.0 M solution of tri-tert-butylphosphine in toluene, followed by 300 mg (1.3 mmol) of $Pd(OAc)_2$, are then added. The mixture is heated at the boil for 4 h and extended with water and EtOH, and the precipitate is filtered off with suction, washed with water and EtOH and dried. The solid is recrystallised three times from dioxane and then has a purity of >99% according to $^1H$-NMR. The yield is 44.2 g (90%) of colourless solid.

The following compounds (Examples 2b to 10b) are prepared analogously to the process described above.

| Ex. | Structure | Yield (%) |
|---|---|---|
| 2b | 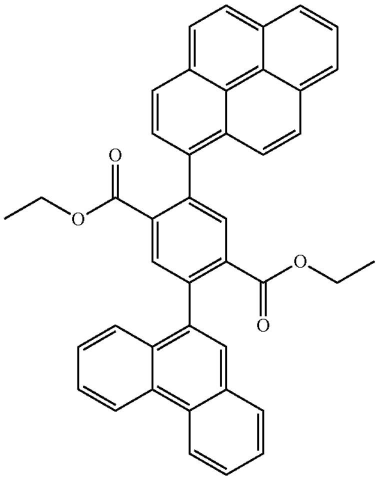 [SMILES: CCOC(=O)c1cc(-c2ccc3ccc4cccc5ccc2c3c45)c(C(=O)OCC)cc1-c1cc2ccccc2c2ccccc12] | 95 |
| 3b | 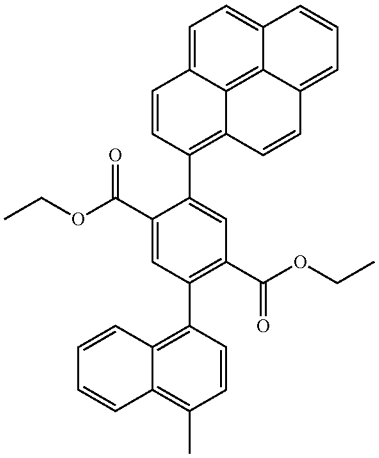 [SMILES: CCOC(=O)c1cc(-c2ccc3ccc4cccc5ccc2c3c45)c(C(=O)OCC)cc1-c1ccc(C)c2ccccc12] | 50 |
| 4b | 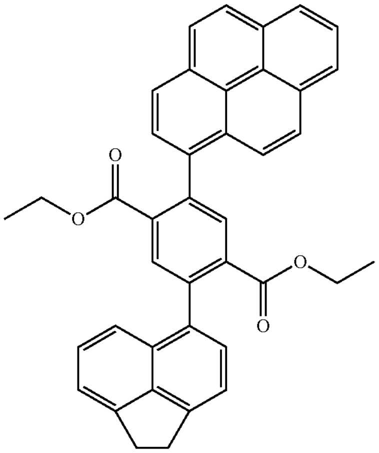 [SMILES: CCOC(=O)c1cc(-c2ccc3ccc4cccc5ccc2c3c45)c(C(=O)OCC)cc1-c1ccc2c3c(cccc13)CC2] | 53 |
-continued
| Ex. | Structure | Yield (%) |
|---|---|---|
| 5b | 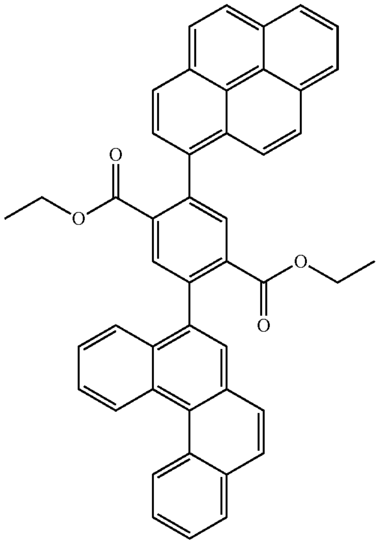 [SMILES: CCOC(=O)c1cc(-c2ccc3ccc4cccc5ccc2c3c45)c(C(=O)OCC)cc1-c1cc2ccc3ccccc3c2c2ccccc12] | 67 |
| 6b | 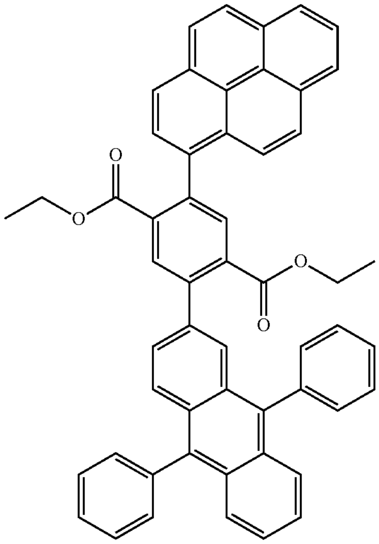 [SMILES: CCOC(=O)c1cc(-c2ccc3ccc4cccc5ccc2c3c45)c(C(=O)OCC)cc1-c1ccc2c(-c3ccccc3)c3ccccc3c(-c3ccccc3)c2c1] | 12 |
| 7b | 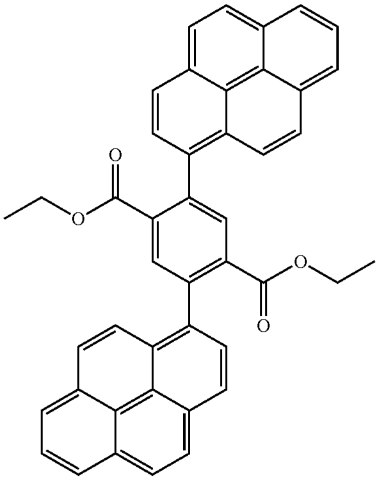 [SMILES: CCOC(=O)c1cc(-c2ccc3ccc4cccc5ccc2c3c45)c(C(=O)OCC)cc1-c1ccc2ccc3cccc4ccc1c2c34] | 36 |

-continued

| Ex. | Structure | Yield (%) |
|---|---|---|
| 8b | 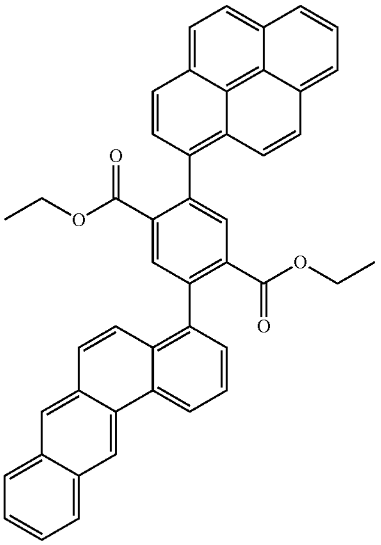 [SMILES: CCOC(=O)c1cc(-c2ccc3ccc4cccc5ccc2c3c45)c(C(=O)OCC)cc1-c1cccc2c1ccc1cc3ccccc3cc12] | 50 |
| 9b | 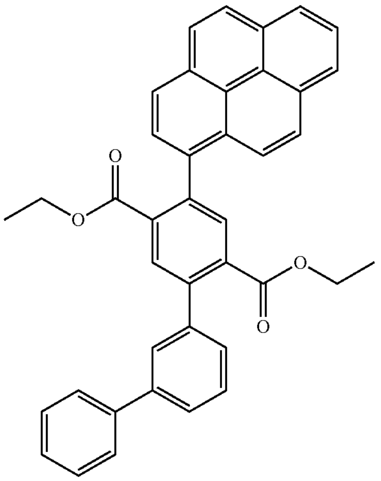 [SMILES: CCOC(=O)c1cc(-c2ccc3ccc4cccc5ccc2c3c45)c(C(=O)OCC)cc1-c1cccc(-c2ccccc2)c1] | 62 |
| 10b | 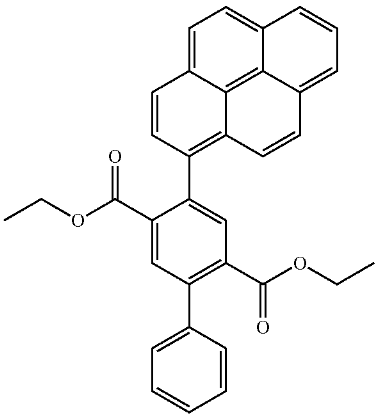 [SMILES: CCOC(=O)c1cc(-c2ccc3ccc4cccc5ccc2c3c45)c(C(=O)OCC)cc1-c1ccccc1] | 75 |

c) 2-[4-(1-Hydroxy-1-methylethyl)-2-naphthalen-1-yl-5-pyren-1-ylphenyl]propan-2-ol

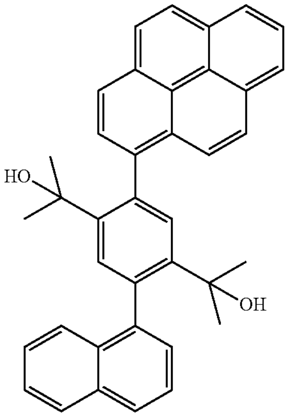 [SMILES: CC(C)(O)c1cc(-c2ccc3ccc4cccc5ccc2c3c45)c(C(C)(C)O)cc1-c1cccc2ccccc12]

30 g (55 mol) of diethyl 2-naphthalen-1-yl-5-pyren-1-ylterephthalate are dissolved in 270 ml of dry THF, 110 ml (330 mmol) of a 3 M methylmagnesium chloride solution in THF are added dropwise at 5° C., and the mixture is stirred at RT for 12 h. After the reaction has been interrupted by addition of 180 ml of 25% acetic acid, the mixture is worked up by extraction with ethyl acetate/water, dried over $Na_2SO_4$ and evaporated in a rotary evaporator. Recrystallisation from EtOH/toluene leaves 26.3 g (92%) of colourless solid, which has a purity of >98% according to $^1$H-NMR.

The following compounds (Examples 2c to 9c) are prepared analogously to the process described above. In Example 10c, phenyllithium is employed as reagent instead of methylmagnesium chloride.

| Ex. | Structure | Yield (%) |
|---|---|---|
| 2c | 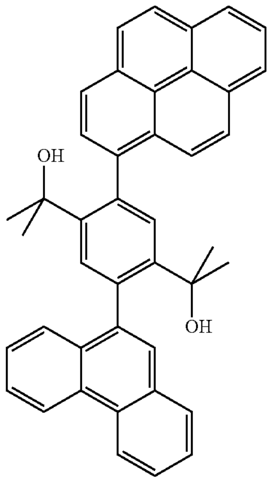 [SMILES: CC(C)(O)c1cc(-c2ccc3ccc4cccc5ccc2c3c45)c(C(C)(C)O)cc1-c1cc2ccccc2c2ccccc12] | 92 |

-continued
| Ex. | Structure | Yield (%) |
| --- | --- | --- |
| 3c | 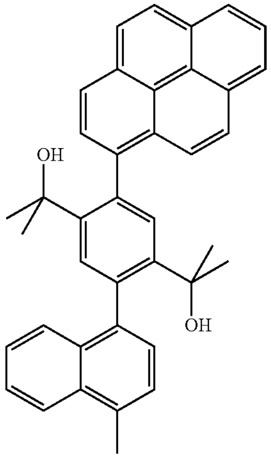 [SMILES: Cc1ccc(-c2cc(C(C)(C)O)c(-c3ccc4ccc5cccc6ccc3c4c56)cc2C(C)(C)O)c2ccccc12] | 78 |
| 4c | 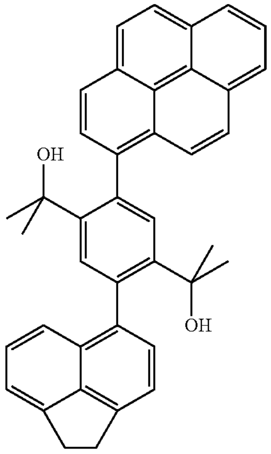 [SMILES: CC(C)(O)c1cc(-c2ccc3ccc4cccc5ccc2c3c45)c(C(C)(C)O)cc1-c1ccc2c3c(cccc13)CC2] | 94 |
| 5c | 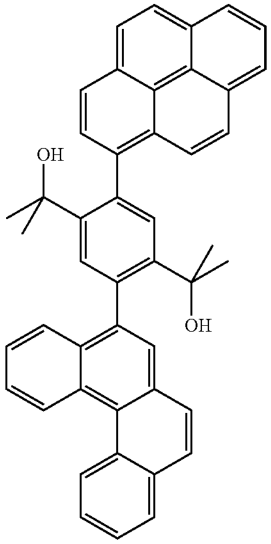 [SMILES: CC(C)(O)c1cc(-c2ccc3ccc4cccc5ccc2c3c45)c(C(C)(C)O)cc1-c1cc2ccc3ccccc3c2c2ccccc12] | 80 |
-continued
| Ex. | Structure | Yield (%) |
| --- | --- | --- |
| 6c | 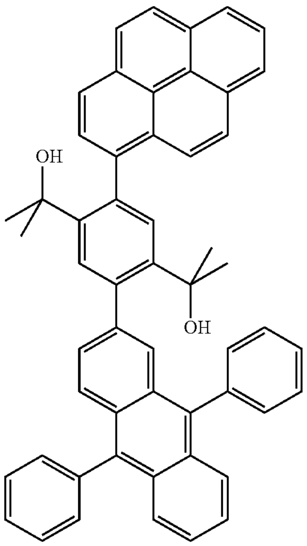 [SMILES: CC(C)(O)c1cc(-c2ccc3ccc4cccc5ccc2c3c45)c(C(C)(C)O)cc1-c1ccc2c(-c3ccccc3)c3ccccc3c(-c3ccccc3)c2c1] | 73 |
| 7c | 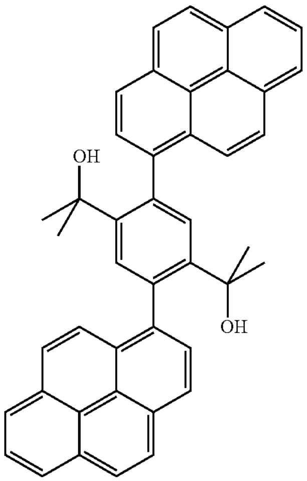 [SMILES: CC(C)(O)c1cc(-c2ccc3ccc4cccc5ccc2c3c45)c(C(C)(C)O)cc1-c1ccc2ccc3cccc4ccc1c2c34] | 90 |

-continued

| Ex. | Structure | Yield (%) |
| --- | --- | --- |
| 8c | 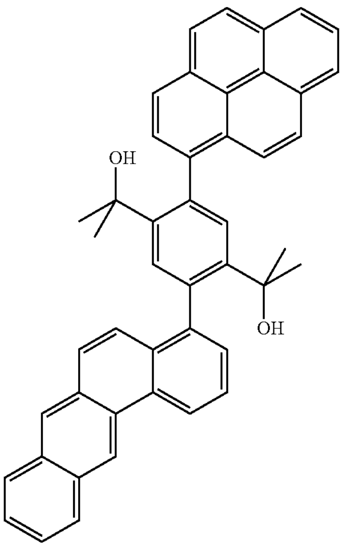 [SMILES: CC(C)(O)c1cc(-c2ccc3ccc4cccc5ccc2c3c45)c(C(C)(C)O)cc1-c1cccc2c1ccc1cc3ccccc3cc12] | quant. |
| 9c | 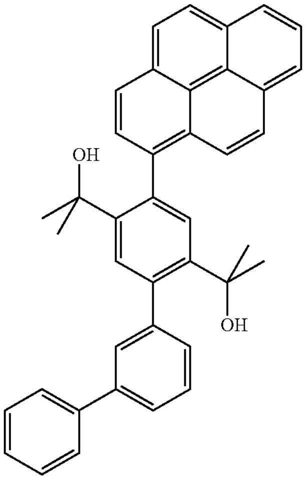 [SMILES: CC(C)(O)c1cc(-c2ccc3ccc4cccc5ccc2c3c45)c(C(C)(C)O)cc1-c1cccc(-c2ccccc2)c1] | quant. |

-continued

| Ex. | Structure | Yield (%) |
| --- | --- | --- |
| 10c | 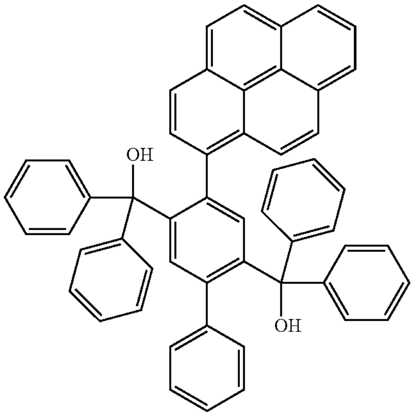 [SMILES: OC(c1ccccc1)(c1ccccc1)c1cc(-c2ccc3ccc4cccc5ccc2c3c45)c(C(O)(c2ccccc2)c2ccccc2)cc1-c1ccccc1] | quant. |

d) 1,1-Dimethylbenzindeno-1,1-dimethylindeno[a]pyrene

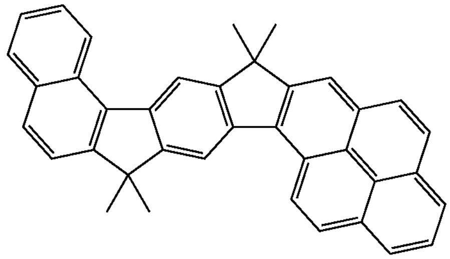 [SMILES: CC1(C)c2cc3c(cc2-c2c1ccc1ccccc21)C(C)(C)c1cc2ccc4cccc5ccc(c1-3)c2c45]

26.3 g (50.5 mmol) of 2-[4-(1-hydroxy-1-methylethyl)-2-naphthalen-1-yl-5-pyren-1-ylphenyl]propan-2-ol are dissolved in 750 ml of dichloromethane, 45 ml of methanesulfonic acid in 70 g of polyphosphoric acid are added dropwise at −20° C., and the mixture is stirred at this temperature for 1 h. When the reaction is complete, 400 ml of EtOH are added dropwise, the mixture is heated at the boil for 1 h, and the yellow solid is filtered off. Recrystallisation four times from NMP and sublimation twice in vacuo ($p=1\times10^{-5}$ mbar, T=340° C.) gives a yellow powder having a purity>99.9% (16 g, 65%).

The following compounds (Examples 2d to 10d) are prepared analogously to the process described above.

| Ex. | Structure | Yield (%) |
| --- | --- | --- |
| 2d | 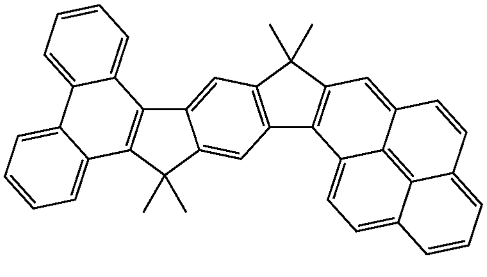 [SMILES: CC1(C)c2cc3c(cc2-c2c1cc1ccc4cccc5ccc2c1c45)C(C)(C)c1c-3c2ccccc2c2ccccc12] | 27 |

-continued
| Ex. | Structure | Yield (%) |
|---|---|---|
| 3d | 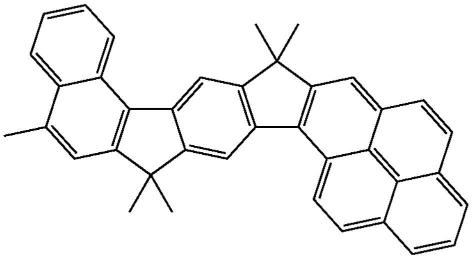 [SMILES: Cc1cc2c(c3ccccc13)-c1cc3c(cc1C2(C)C)-c1c(cc2ccc4cccc5ccc1c2c45)C3(C)C] | 41 |
| 4d | 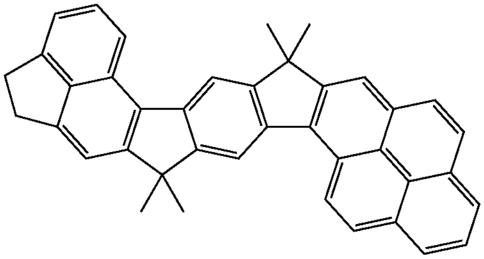 [SMILES: CC1(C)c2cc3c(cc2-c2c1cc1c4c(cccc24)CC1)C(C)(C)c1cc2ccc4cccc5ccc(c1-3)c2c45] | 50 |
| 5d | 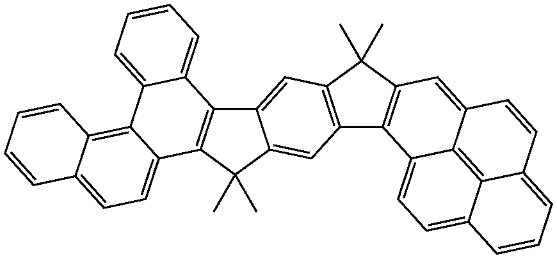 [SMILES: CC1(C)c2cc3c(cc2-c2c1cc1ccc4cccc5ccc2c1c45)C(C)(C)c1c-3c2ccccc2c2c1ccc1ccccc12] | 15 |
| 6d | 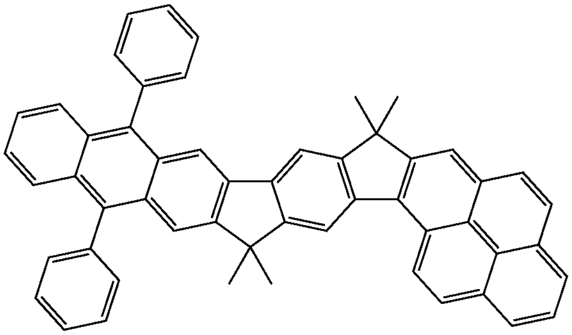 [SMILES: CC1(C)c2cc3c(cc2-c2cc4c(-c5ccccc5)c5ccccc5c(-c5ccccc5)c4cc21)C(C)(C)c1cc2ccc4cccc5ccc(c1-3)c2c45] | 32 |
| 7d | 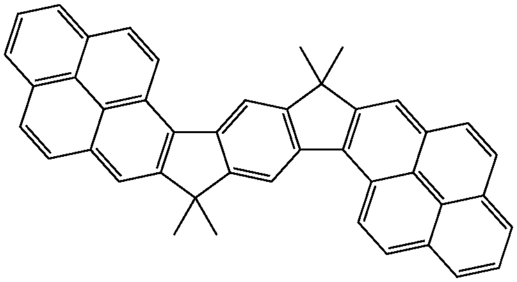 [SMILES: CC1(C)c2cc3c(cc2-c2c1cc1ccc4cccc5ccc2c1c45)C(C)(C)c1cc2ccc4cccc5ccc(c1-3)c2c45] | 10 |

-continued

| Ex. | Structure | Yield (%) |
|---|---|---|
| 8d | 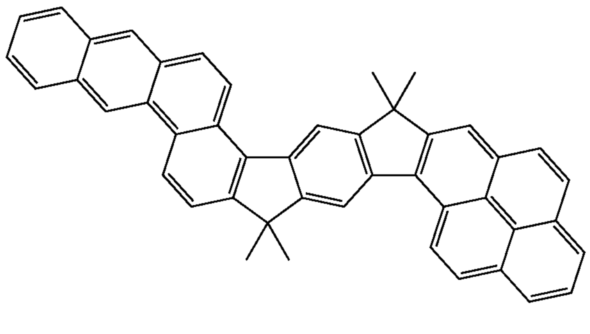 [SMILES: CC1(C)c2cc3c(cc2-c2c1ccc1c2ccc2cc4ccccc4cc21)C(C)(C)c1cc2ccc4cccc5ccc(c1-3)c2c45] | 53 |
| 9d | 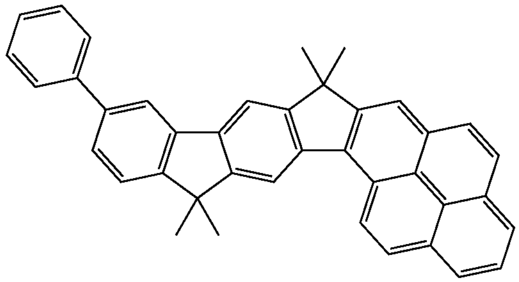 [SMILES: CC1(C)c2ccc(-c3ccccc3)cc2-c2cc3c(cc21)-c1c(cc2ccc4cccc5ccc1c2c45)C3(C)C] | 37 |
| 10d | 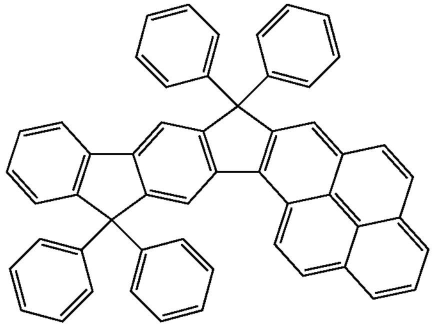 [SMILES: c1ccc(C2(c3ccccc3)c3ccccc3-c3cc4c(cc32)-c2c(cc3ccc5cccc6ccc2c3c56)C4(c2ccccc2)c2ccccc2)cc1] | 37 |

Example 11: Synthesis of 1,1-dimethylbenzindeno-1,1-dimethylindeno[b]fluoranthene a) Diethyl 2-chloro-5-naphthalen-1-ylterephthalate

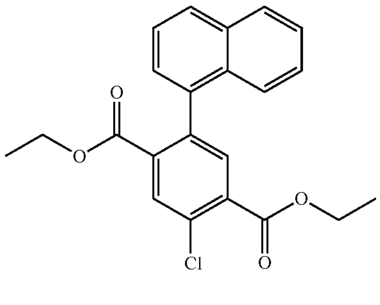 [SMILES: CCOC(=O)c1cc(-c2cccc3ccccc23)c(C(=O)OCC)cc1Cl]

51 g (298 mmol) of 1-naphthylboronic acid, 100 g (298 mmol) of diethyl chlorobromoterephthalate and 144 g (626 mmol) of potassium phosphate monohydrate are initially introduced in a mixture of 600 ml of dist. water, 400 ml of toluene and 200 ml of dioxane and saturated with $N_2$ for 30 min. 5.4 g (18 mmol) of tri(o-tolyl)phosphine and 669 mg (3 mmol) of palladium(II) acetate are subsequently added, and the mixture is heated at the boil for 3 h. After dilution with toluene, the organic phase is separated off, washed twice with water, dried over $Na_2SO_4$ and evaporated in vacuo. The oil which remains is distilled in a thin-film evaporator ($p=5\times10^{-3}$ mbar, T=130° C.) and isolated in the form of a yellow oil (74 g, 65%), which, according to $^1$H-NMR, has a purity of >95%.

b) Diethyl 2-fluoranthen-3-yl-5-naphthalen-1-ylterephthalate

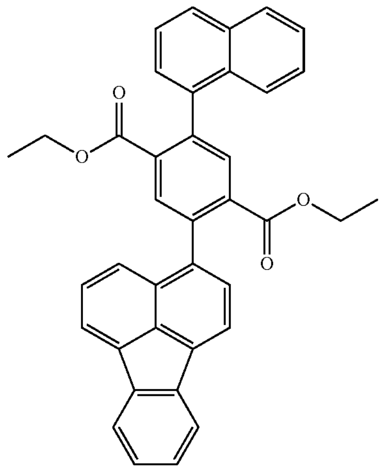 [SMILES: CCOC(=O)c1cc(-c2ccc3c4c(cccc24)-c2ccccc2-3)c(C(=O)OCC)cc1-c1cccc2ccccc12]

15.4 g (40 mmol) of diethyl 2-chloro-5-naphthalen-1-ylterephthalate, 14.0 g (56 mmol) of fluoranthene-3-boronic acid and 17.7 g of $Cs_2CO_3$ are initially introduced in 70 ml of dry dioxane and saturated with $N_2$ for 30 min. 0.8 ml of a 1.0 M solution of tri-tert-butylphosphine in toluene, followed by 91 mg (0.4 mmol) of $Pd(OAc)_2$ are then added. The mixture is heated at the boil for 4 h, extended with water and EtOH, the precipitate is filtered off with suction, washed with heptane and dried. The solid is recrystallised from toluene and then has, according to $^1$H-NMR, a purity of >95%. The yield is 8.5 g (38%) of colourless solid.

c) 2-[4-(1-Hydroxy-1-methylethyl)-2-fluoranthen-3-yl-5-naphthalin-1-ylphenyl]propan-2-ol

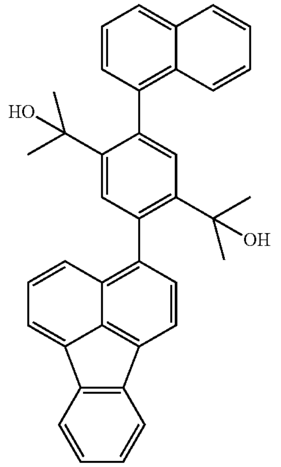 [SMILES: CC(C)(O)c1cc(-c2ccc3c4c(cccc24)-c2ccccc2-3)c(C(C)(C)O)cc1-c1cccc2ccccc12]

8.5 g (15 mol) of diethyl 2-fluoranthen-3-yl-5-naphthalin-1-ylterephthalate are dissolved in 75 ml of dry THF, 31 ml (93 mmol) of a 3 M methylmagnesium chloride solution in THF are added at 5° C., and the mixture is stirred at RT for 12 h. After interruption of the reaction by addition of 30 ml of 25% acetic acid, the mixture is worked up by extraction with ethyl acetate/water, dried over $Na_2SO_4$ and evaporated in a rotary evaporator, giving 8.0 g (99%) of the crude product, which is employed in the next step without further purification.

d) 1,1-Dimethylbenzindeno-1,1-dimethylindeno[b]fluoranthene

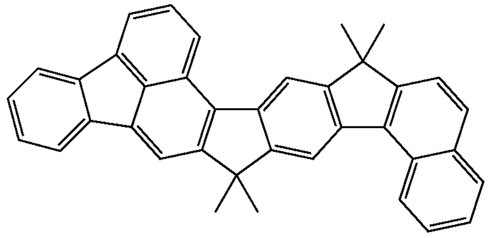 [SMILES: CC1(C)c2cc3c(cc2-c2c1ccc1ccccc21)C(C)(C)c1cc2c4c(cccc4c1-3)-c1ccccc1-2]

8.0 g (15.4 mmol) of 2-[4-(1-hydroxy-1-methylethyl)-2-fluoranthen-3-yl-5-naphthalen-1-ylphenyl]propan-2-ol are dissolved in 250 ml of dichloromethane, 15 ml of methanesulfonic acid in 22 g of polyphosphoric acid are added dropwise at −20° C., and the mixture is stirred at this temperature for 1 h. When the reaction is complete, 130 ml of EtOH are added dropwise, the mixture is heated at the boil for 1 h, and the yellow solid is filtered off. Recrystallisation twice from toluene and sublimation twice in vacuo ($p=4\times10^{-6}$ mbar, T=300° C.) gives a yellow powder having a purity of >99.9% (1.9 g, 25%).

Example 12: Synthesis of 1,1-diphenylbenzindeno-1,1-diphenyl-indeno[a]pyrene

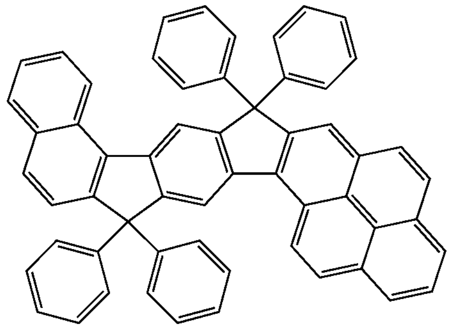 [SMILES: c1ccc(C2(c3ccccc3)c3cc4c(cc3-c3c2ccc2ccccc32)C(c2ccccc2)(c2ccccc2)c2cc3ccc5cccc6ccc(c2-4)c3c56)cc1]

The synthesis is carried out analogously to Example 1, with phenylmagnesium chloride solution being used instead of methylmagnesium chloride solution in step c).

Example 13: Production of OLEDs

OLEDs are produced by a process which is described in general in WO 04/058911 and which is adapted in individual cases to the particular circumstances (for example layer-thickness variation in order to achieve optimum efficiency or colour).

The results for various OLEDs are presented in Examples 14 to 31 below. Glass plates which have been coated with structured ITO (indium tin oxide) form the substrates of the OLEDs. The OLEDs consist of the following layer sequence: substrate/hole-injection layer (HIM)/hole-transport layer (HTM1) 60 nm/hole-transport layer (HTM2) 20 nm/emission layer (EML) 30 nm/electron-transport layer (ETM) 20 nm and finally a cathode. The materials are thermally vapour-deposited in a vacuum chamber. The emission layer here always consists of a matrix material (host) and a dopant, which is admixed with the host by co-evaporation. The cathode is formed by a 1 nm thin LiF layer and a 100 nm Al layer deposited on top. Table 4 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current-voltage-luminance characteristic lines (IUL characteristic lines), and the lifetime are determined. The lifetime is defined as the time after which the initial luminance of 6000 cd/$m^2$ (for blue-emitting OLEDs) or 25,000 cd/$m^2$ (for green-emitting OLEDs) has dropped to half.

Tables 5 and 6 show the results for some OLEDs (Examples 14 to 31). The host materials and emitter materials according to the invention are the compounds of Examples 1d, 2d, 5d and 12. The comparative examples used are host H1 and emitters D1, D2 or D3 in accordance with the prior art.

As is clearly evident from the results in Tables 5 and 6, organic electroluminescent devices comprising the compounds according to the invention have a significantly longer lifetime for use of the compound according to the invention as matrix material and improved colour coordinates and a significantly longer lifetime for use as dopants compared with materials in accordance with the prior art.

TABLE 4

HTM1

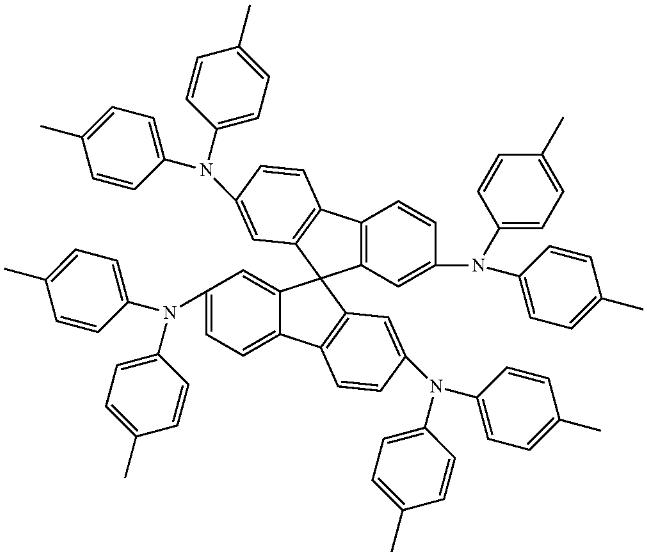

HTM 2

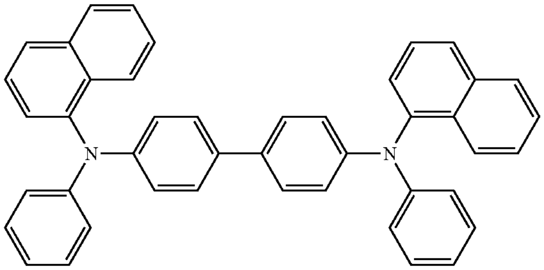 [SMILES: c1ccc(N(c2ccc(-c3ccc(N(c4ccccc4)c4cccc5ccccc45)cc3)cc2)c2cccc3ccccc23)cc1]

HIM

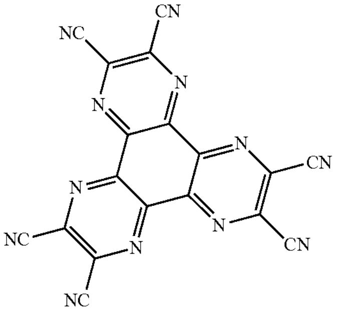 [SMILES: N#Cc1nc2c3nc(C#N)c(C#N)nc3c3nc(C#N)c(C#N)nc3c2nc1C#N]

TABLE 4-continued
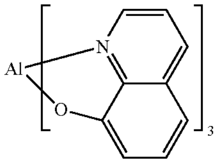
ETM1
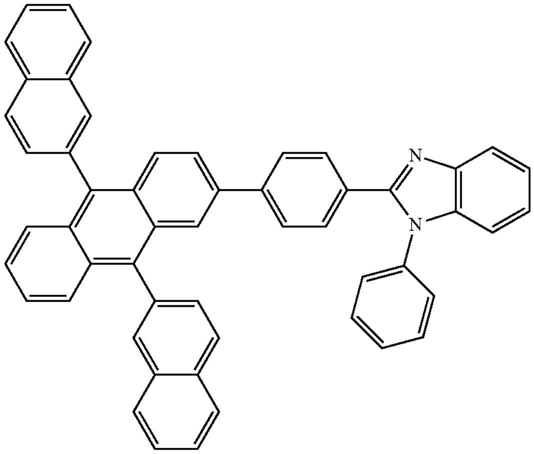 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM 2
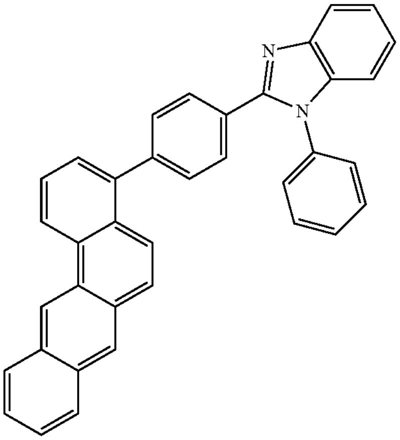 [SMILES: c1ccc(-n2c(-c3ccc(-c4cccc5c4ccc4cc6ccccc6cc45)cc3)nc3ccccc32)cc1]
ETM3
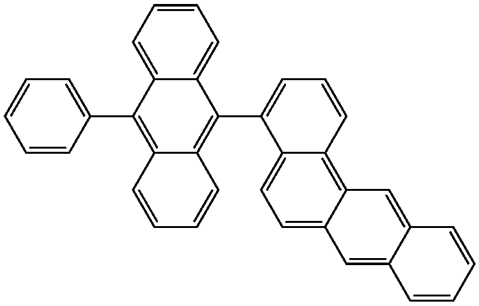 [SMILES: c1ccc(-c2c3ccccc3c(-c3cccc4c3ccc3cc5ccccc5cc34)c3ccccc23)cc1]
H2
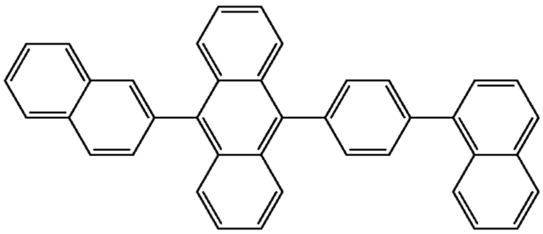 [SMILES: c1ccc2cc(-c3c4ccccc4c(-c4ccc(-c5cccc6ccccc56)cc4)c4ccccc34)ccc2c1]
H1

TABLE 4-continued
D1
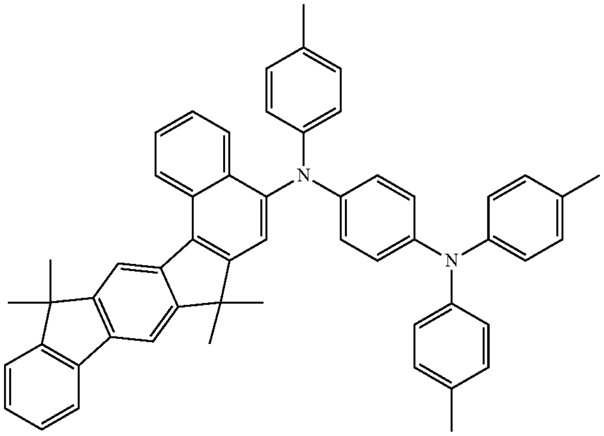 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
D2
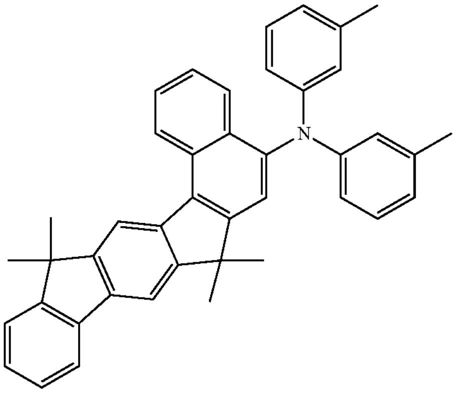 [SMILES: Cc1cccc(N(c2cccc(C)c2)c2cc3c(c4ccccc24)-c2cc4c(cc2C3(C)C)-c2ccccc2C4(C)C)c1]
D3
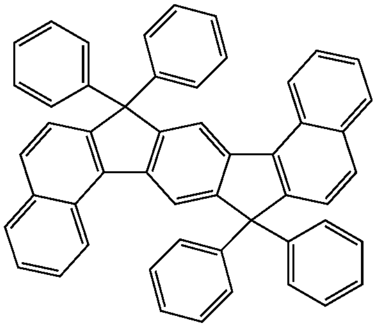 [SMILES: c1ccc(C2(c3ccccc3)c3cc4c(cc3-c3c2ccc2ccccc32)C(c2ccccc2)(c2ccccc2)c2ccc3ccccc3c2-4)cc1]
Bsp. 1d
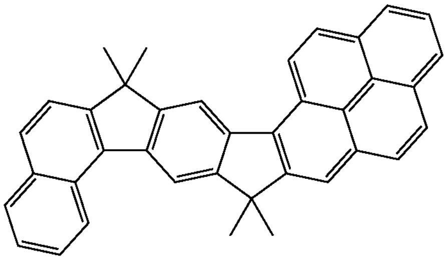 [SMILES: CC1(C)c2cc3c(cc2-c2c1ccc1ccccc21)C(C)(C)c1cc2ccc4cccc5ccc(c1-3)c2c45]

TABLE 4-continued

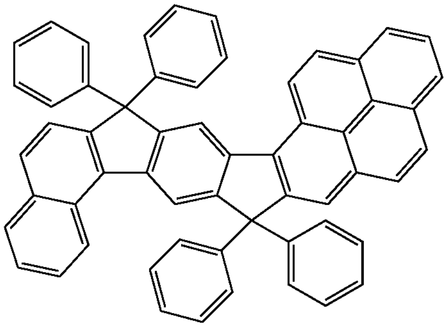 [SMILES: c1ccc(C2(c3ccccc3)c3cc4c(cc3-c3c2ccc2ccccc32)C(c2ccccc2)(c2ccccc2)c2cc3ccc5cccc6ccc(c2-4)c3c56)cc1]

Ex. 12

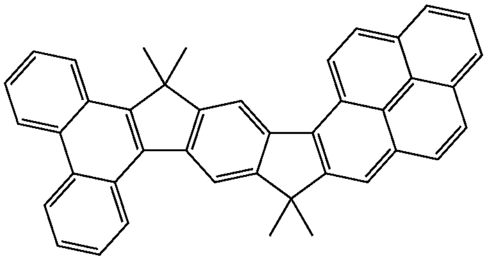 [SMILES: CC1(C)c2cc3c(cc2-c2c1cc1ccc4cccc5ccc2c1c45)C(C)(C)c1c-3c2ccccc2c2ccccc12]

Ex. 2d

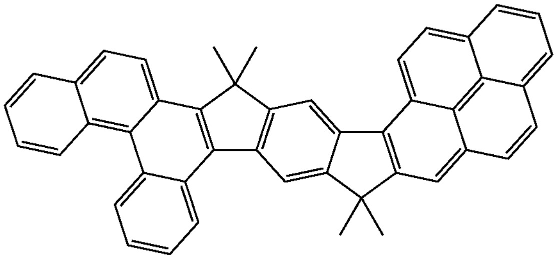 [SMILES: CC1(C)c2cc3c(cc2-c2c1cc1ccc4cccc5ccc2c1c45)C(C)(C)c1c-3c2ccccc2c2c1ccc1ccccc12]

Ex. 5d

TABLE 5

| Ex. | EML | ETM | Colour | Eff. (cd/A) at 1000 cd/m$^2$ | Voltage (V) at 1000 cd/m$^2$ | CIE | Life-time at 25000 cd/m$^2$ (h) |
|---|---|---|---|---|---|---|---|
| 14 (comp.) | H1 + 9% of D1 | ETM2 | green | 16.3 | 5.2 | x = 0.29/ y = 0.60 | 300 |
| 15 | Ex. 12 + 9% of D1 | ETM2 | green | 18.1 | 4.3 | x = 0.29/ y = 0.61 | 320 |

TABLE 6

| Example | EML | ETM | Colour | Max. efficiency (cd/A) | Voltage (V) at 1000 cd/m$^2$ | CIE | Lifetime at 6000 cd/m$^2$ (h) |
|---|---|---|---|---|---|---|---|
| 16 (comp.) | H1 + 5% of D2 | ETM1 | blue | 4.1 | 5.3 | x = 0.14/ y = 0.16 | 160 |

TABLE 6-continued

| Example | EML | ETM | Colour | Max. efficiency (cd/A) | Voltage (V) at 1000 cd/m$^2$ | CIE | Lifetime at 6000 cd/m$^2$ (h) |
|---|---|---|---|---|---|---|---|
| 17 (comp.) | H2 + 5% of D2 | ETM1 | blue | 4.3 | 5.2 | x = 0.14/ y = 0.15 | 180 |
| 18 (comp.) | H2 + 5% of D3 | ETM1 | blue | 1.5 | 5.1 | x = 0.16/ y = 0.10 | 30 |
| 19 (comp.) | H1 + 5% of D2 | H2 (50%) + ETM3 (50%) | blue | 4.9 | 5.0 | x = 0.14/ y = 0.16 | 90 |
| 20 (comp.) | H2 + 5% of D2 | H2 (50%) + ETM3 (50%) | blue | 5.3 | 4.9 | x = 0.14/ y = 0.15 | 120 |
| 21 (comp.) | H2 + 5% of D3 | H2 (50%) + ETM3 (50%) | blue | 1.9 | 5.0 | x = 0.16/ y = 0.09 | 65 |
| 22 | H2 + 5% of Ex. 1d | ETM1 | blue | 3.5 | 5.9 | x = 0.15/ y = 0.14 | 230 |

TABLE 6-continued

| Example | EML | ETM | Colour | Max. efficiency (cd/A) | Voltage (V) at 1000 cd/m² | CIE | Lifetime at 6000 cd/m² (h) |
|---|---|---|---|---|---|---|---|
| 23 | H2 + 3% of Ex. 1d | ETM2 | blue | 3.0 | 5.8 | x = 0.15/ y = 0.11 | 210 |
| 24 | H2 + 5% of Ex. 1d | H2 (50%) + ETM3 (50%) | blue | 6.4 | 4.6 | x = 0.15/ y = 0.13 | 240 |
| 25 | H2 + 1% of Ex. 1d | H2 (50%) + ETM3 (50%) | blue | 5.5 | 4.4 | x = 0.14/ y = 0.11 | 260 |
| 26 | H2 + 1% of Ex. 2d | H2 (50%) + ETM3 (50%) | blue | 4.7 | 4.8 | x = 0.15/ y = 0.10 | 260 |
| 27 | H2 + 5% of Ex. 2d | H2 (50%) + ETM3 (50%) | blue | 5.0 | 4.7 | x = 0.15/ y = 0.11 | 270 |
| 28 | H2 + 5% of Ex. 2d | ETM2 | blue | 4.6 | 5,4 | x = 0.15/ y = 0.11 | 290 |
| 29 | H2+ 1% of Ex. 5d | H2 (50%) + ETM3 (50%) | blue | 7.4 | 4.7 | x = 0.14/ y = 0.15 | 300 |
| 30 | H2 + 5% of Ex. 5d | H2 (50%) + ETM3 (50%) | blue | 7.8 | 4.5 | x = 0.14/ y = 0.16 | 310 |
| 31 | H2 + 5% of Ex. 5d | ETM2 | blue | 6.8 | 5.3 | x = 0.14/ y = 0.16 | 330 |

The invention claimed is:

1. An electroluminescent element comprising a compound of formula (111) to (128), (138) or (139)

formula (111)

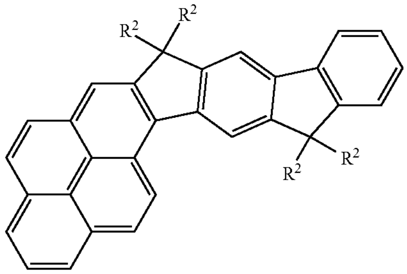

-continued formula (112)

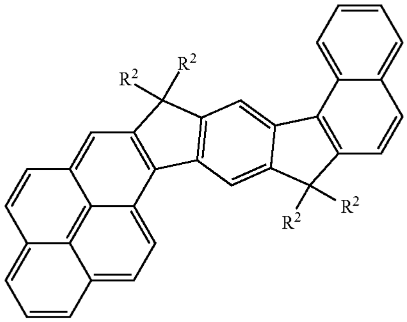

formula (113)

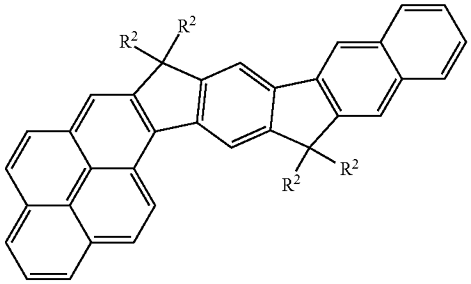

formula (114)

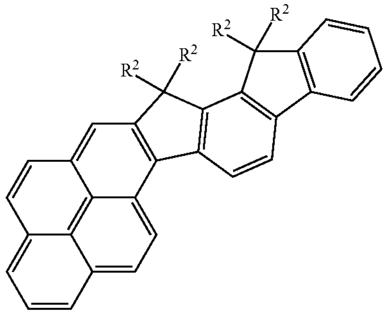

formula (115)

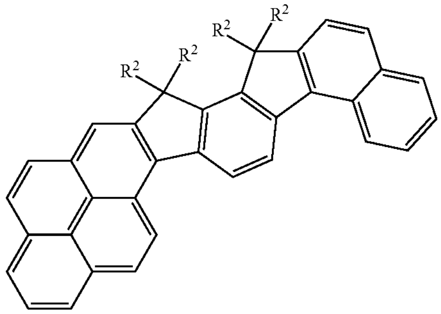

-continued
formula (116)
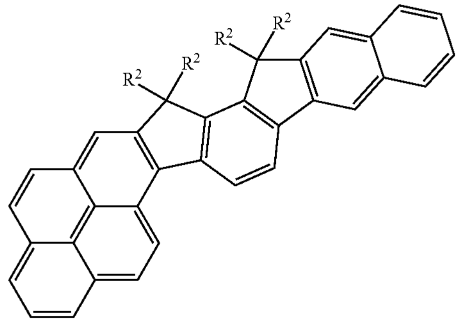
formula (117)
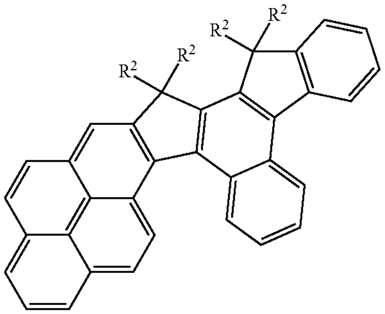
formula (118)
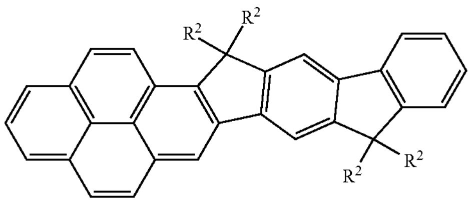
formula (119)
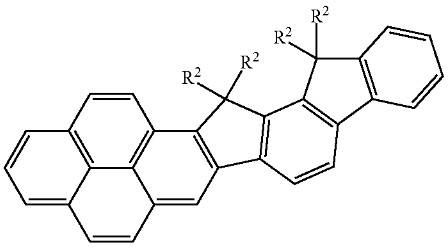
formula (120)
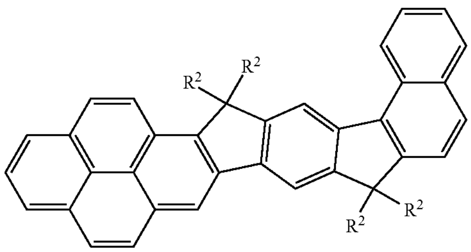
-continued
formula (121)
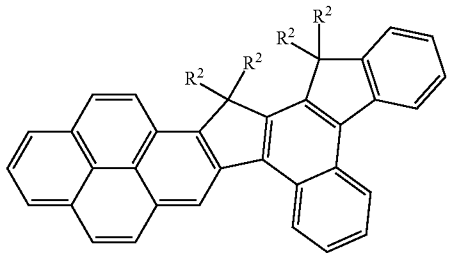
formula (122)
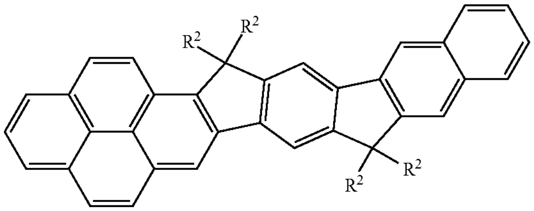
formula (123)
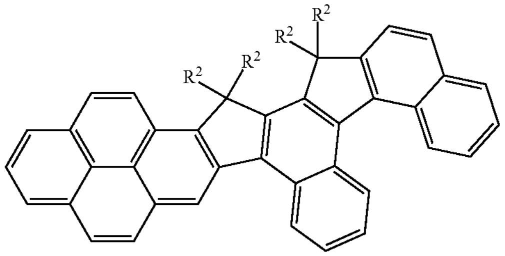
formula (124)
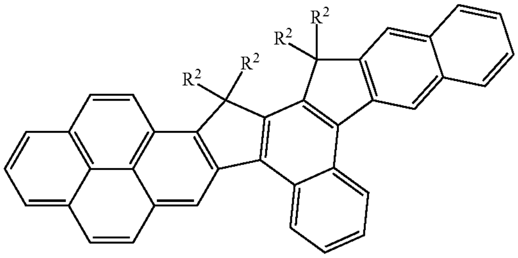
formula (125)
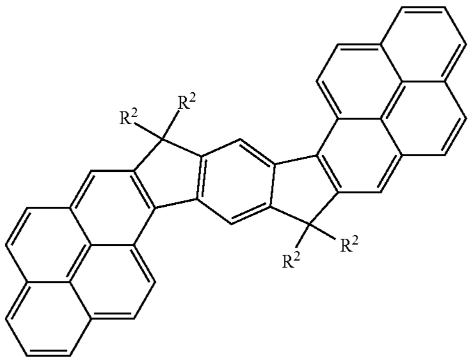

-continued formula (126)

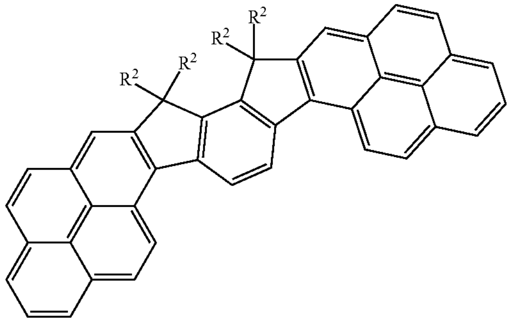

formula (127)

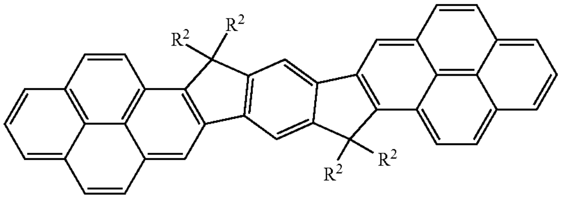

formula (128)

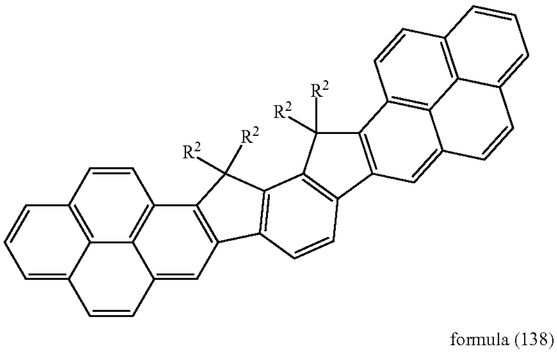

formula (138)

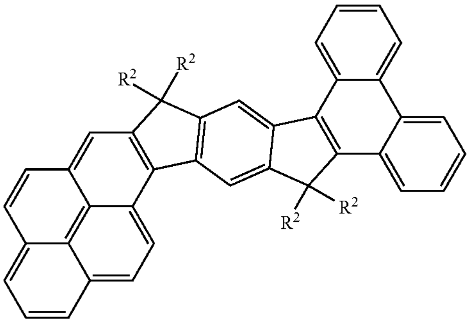

formula (139)

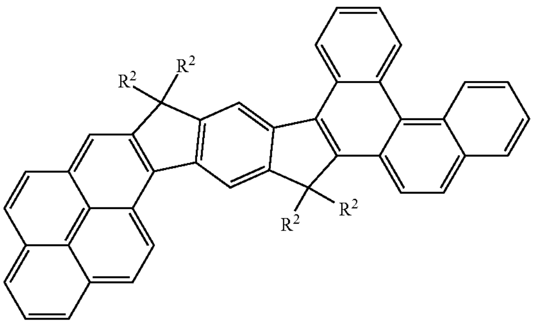

formula (1)

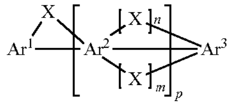

wherein where the aromatic systems may each also be substituted by one or more radicals $R^1$;

$R^1$ and $R^2$ are on each occurrence, identically or differently, H, D, F, Cl, Br, I, $C(=O)Ar^4$, $P(=O)(Ar^4)_2$, $S(=O)Ar^4$, $S(=O)_2Ar^4$, $CR^2=CR^2Ar^4$, CHO, $CR^3=C(R^3)_2$, CN, $NO_2$, $Si(R^3)_3$, $B(OR^3)_2$, $B(R^3)_2$, $B(N(R^3)_2)_2$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which are optionally substituted by one or more radicals $R^3$, where in each case one or more non-adjacent $CH_2$ groups are optionally replaced by $R^3C=CR^3$, C≡C, $Si(R^3)_2$, $Ge(R^3)_2$, $Sn(R^3)_2$, C=O, C=S, C=Se, $C=NR^3$, $P(=O)R^3$, SO, $SO_2$, O, S or $CONR^3$ and where one or more H atoms are optionally replaced by F, Cl, Br, I, CN or $NO_2$, or an aromatic or heteroaromatic ring system having 5 to 60 aromatic ring atoms, which in each case are optionally substituted by one or more radicals $R^3$, or a combination of these systems; and wherein two or more substituents $R^1$ or $R^2$ optionally define a mono- or polycyclic, aliphatic or aromatic ring system with one another;

$Ar^4$ is on each occurrence, identically or differently, an aromatic or heteroaromatic ring system having 5-30 aromatic ring atoms, which are optionally substituted by one or more non-aromatic radicals $R^1$; and wherein two radicals Ar on the same nitrogen or phosphorus atom are optionally linked to one another here by a single bond or a bridge X;

$R^3$ is on each occurrence, identically or differently, H or an aliphatic or aromatic hydrocarbon radical having 1 to 20 C atoms;

as a blue emitting compound in the emitting layer, where the compound of formula is present in the emitting layer in combination with a host material selected from the group consisting of oligoarylenes, oligoarylenes containing condensed aromatic groups, anthracenes, oligoarylenevinylenes, polypodal metal complexes, hole-conducting compounds, electron-conducting compounds, ketones, phosphine oxides, sulfoxides, boronic acid derivatives, benzanthracenes, and where the compound of formula is present in the emitting layer in a proportion of 0.5 to 20% by vol.

2. The electroluminescent element according to claim 1 wherein $R^1$ is selected on each occurrence, identically or differently, from H, D, F, $Si(R^3)_3$, straight-chain alkyl or alkoxy groups having 1 to 10 C atoms or branched or cyclic alkyl or alkoxy groups having 3 to 10 C atoms, each of which are optionally substituted by one or more radicals $R^3$, where in each case one or more non-adjacent $CH_2$ groups may be replaced by $R^3C=CR^3$ or O and where one or more H atoms are optionally replaced by F, or aromatic or heteroaromatic ring systems having 5 to 40 aromatic ring atoms, or a combination of these systems; and wherein two or more substituents $R^1$ optionally define a mono- or polycyclic, aliphatic or aromatic ring system with one another.

3. The electroluminescent element according to claim 1, wherein $R^2$ is selected on each occurrence, identically or differently, from H, straight-chain alkyl groups having 1 to 10 C atoms or branched or cyclic alkyl groups having 3 to 10 C atoms, where in each case one or more non-adjacent $CH_2$ groups are optionally replaced by —$R^2C$=$CR^2$— or —O— and where one or more H atoms are optionally replaced by F, or a monovalent aryl or heteroaryl group having 5 to 16 aromatic ring atoms, which may be substituted by one or more non-aromatic radicals $R^2$; and wherein two radicals $R^2$ which are bonded in the same group X optionally form a ring system with one another.

4. The electroluminescent element according to claim 1, wherein the host material is selected from anthracenes.

* * * * *